(12) United States Patent
Cook et al.

(10) Patent No.: US 6,329,523 B1
(45) Date of Patent: *Dec. 11, 2001

(54) COMPOUNDS HAVING A PLURALITY OF NITROGENOUS SUBSTITUTENTS

(75) Inventors: Phillip Dan Cook, Lake San Marcos; Haoyun An, Encinitas, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/230,773
(22) PCT Filed: Aug. 1, 1997
(86) PCT No.: PCT/US97/13530
§ 371 Date: Mar. 10, 1999
§ 102(e) Date: Mar. 10, 1999
(87) PCT Pub. No.: WO98/05961
PCT Pub. Date: Feb. 12, 1998

Related U.S. Application Data

(63) Continuation-in-part of application No. 08/691,206, filed on Aug. 1, 1996, now Pat. No. 6,077,954.

(51) Int. Cl.[7] .................... C07D 241/42; C07D 213/36; C07D 249/08
(52) U.S. Cl. .................... 544/353; 544/162; 544/180; 544/182; 544/215; 544/301; 544/333; 544/335; 544/336; 544/354; 544/358; 544/405; 544/360; 548/264.4; 548/267.2; 548/267.8; 548/950; 548/967; 546/271.4; 546/272.4; 546/278.1; 546/329; 546/334; 546/335; 546/336; 546/337; 549/74; 549/75; 549/426; 549/492; 564/367; 564/368; 564/369; 564/371; 564/453; 564/454; 564/455
(58) Field of Search ................ 514/253.01, 357; 546/337, 329, 335, 336; 544/360, 162, 215, 333, 335, 353; 564/367, 368, 369, 371, 453, 454, 455; 549/426, 492

(56) References Cited

U.S. PATENT DOCUMENTS

| | | | |
|---|---|---|---|
| 3,687,808 | 8/1972 | Merigan, Jr. et al. | 195/28 |
| 5,288,514 | 2/1994 | Ellman | 427/2 |
| 5,324,483 | 6/1994 | Cody et al. | 422/131 |
| 5,380,899 | 1/1995 | Noda et al. | 544/242 |
| 5,567,411 | 10/1996 | Keana et al. | 424/9.1 |
| 6,077,954 | * 6/2000 | Cook et al. | 544/353 |

FOREIGN PATENT DOCUMENTS

| | | |
|---|---|---|
| 3-52861 | 3/1991 | (JP) . |
| WO 91/19735 | 12/1991 | (WO) . |
| WO 92/20822 | 11/1992 | (WO) . |
| WO 93/04204 | 3/1993 | (WO) . |
| WO 94/08051 | 4/1994 | (WO) . |
| WO 94/22454 | 10/1994 | (WO) . |
| WO 94/24314 | 10/1994 | (WO) . |
| WO 94/26775 | 11/1994 | (WO) . |
| WO 94/27719 | 12/1994 | (WO) . |
| WO 94/28028 | 12/1994 | (WO) . |
| WO 94/28424 | 12/1994 | (WO) . |

OTHER PUBLICATIONS

Aldrich catalogue, Alrich Chemical, Milwaukee, Wis. p. 1463, 1994.*

Achari et al., "Facing up to Membranes: Structure/Function Relationships in Phospholipases", *Cold Spring Harbor Symp. Quant. Biol.*, 1987, 52, 441–452.

Alul et al., "Oxalyl–CPG: a labile support for synthesis of sensitive oligonucleotide derivatives", *Nucl. Acids. Res.*, 1991, 19(7), 1527–1532.

(List continued on next page.)

*Primary Examiner*—Richard L. Raymond
(74) *Attorney, Agent, or Firm*—Woodcock Washburn Kurtz Mackiewicz & Norris LLP

(57) ABSTRACT

Novel compounds having the formula:

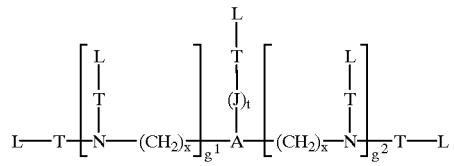

wherein the constituent variables are defined herein. The compounds are constructed to include a central aromatic, aliphatic, or heterocyclic ring system. Attached to the central ring system are two linear groups having nitrogenous moieties that are derivatized with chemical functional groups. The ring system can include further nitrogenous moieties, either as ring atoms or on pendant groups attached to the ring, that may also be derivatized with chemical functional groups. The totality of the chemical functional groups imparts certain conformational and other properties to the these compounds. In accordance with certain embodiments of the invention, libraries of such compounds are prepared utilizing permutations and combinations of the chemical functional groups and the nitrogenous moieties to build complexity into the libraries.

17 Claims, 10 Drawing Sheets

OTHER PUBLICATIONS

Arimoto, M., et al., Semisynthetic β–Lactam Antibiotics III. Synthesis and Antibacterial Activity of 7β–[2–(2–Aminothiazol–4YL)–2–(Substituted Carbamoyl-methoxyimino)Acetamido]Cephalosporins, *J. Antibiot.*, 1986, 39, 1243–1256.

Beaucage et al., "Advances in the Synthesis of Oligonucleotides by the Phosphoramidite Approach", *Tetra.*, 1992, 48(12), 2223–2311.

Bernatowicz, M. S., "Urethane Protected Derivatives of 1–Guanylpyrazole for the Mild and Efficient Preparation of Guanidines", *Tetrahedron Lett.*, 1993, 34, 3389–3392.

Bomalaski et al., "Human Extracellular Recombinant Phospholipase $A_2$ Induces an Inflammatory Response in Rabbit Joints", *J. Immunol.*, 1991, 146(11), 3904–3910.

Bradshaw et al., "Proton–Ionizable Crown Compounds. 4. New Macrocyclic Polyether Ligands Containing a Triazole Subcyclic Unit", *J. Heterocyclic Chem.*, 1986, 23, 361–368.

Buhleier, et al., CA, 1978, 88:152589.

Burack et al., "Role of Lateral Phase Separation in the Modulation of Phospholipase $A_2$ Activity", *Biochem.*, 1993, 32, 583–589.

Campbell et al., "Inhibition of Phospholipase A2; a Molecular Recognition Study", *J. Chem. Soc., Chem. Commun.*, 1988, 1560–1562.

Carell et al., "A Novel Procedure for the Synthesis of Libraries Containing Small Organic Molecules", *Angew. Chem. Int. Ed. Engl.*, 1994, 33(20), 2059–2061.

Carell et al., "A Solution–Phase Screening Procedure for the Isolation of Active Compounds from a Library of Molecules", *Angew. Chem. Int. Ed. Engl.*, 1994, 33(20), 2061–2064.

Carpino, L. A., et al., "Polystyrene–Based Deblocking–Scavenging Agents for the 9–Fluorenylmethyloxycarbonyl Amino–Protecting Group", *J. Org. Chem.*, 1983, 48, 661–665.

Cho et al., "The Chemical Basis for Interfacial Activation of Monomeric Phospholipases $A_2$", *J. Biol. Chem.*, 1988, 263(23), 11237–11241.

Combs, et al., "Protein Structure–Based Combinatoril Chemistry: Discovery of Non–Peptide Binding Elements to Sre SH3 Domain", *J. Am. Chem. Soc.*, 1996, 118, 287–288.

Dennis, E. A., *The Enzymes*, Boyer, P.D., ed., Academic Press, New York, 1983, vol. 16, Ch. 9, 307–353.

Davidson et al., "Inhibition of Phospholipase $A_2$ by "Lipocortins" and Calpactins", *J. Biol. Chem.*, 1987, 262(4), 1698–1705.

Davidson et al., "1–Stearyl,2–Stearoylaminodeoxy Phosphatidylcholine, A Potent Reversible Inhibitor of Phospholipase $A_2$", *Biochem. Biophys. Res. Commun.*, 1986, 137(2), 587–592.

Demonchaux, P., et al., "Search for the pharmacophore of the K+ channel blocker, apamin", *Eur. J. Med. Chem.*, 1991, 26, 915–920.

DeWitt et al., ""Diversomers": An approach to nonpeptide, nonoligomeric chemical diversity", *Proc. Natl. Acad. Sci. USA*, 1993, 90, 6909–6913.

Ecker et al., "Rational screening of oligonucleotide combinatorial libraries of drug discovery", *Nucl. Acids Res.*, 1993, 21(8), 1853–1856.

Englisch et al., "Chemically Modified Oligonuceotides as Probes and Inhibitors", *Angew. Chem. Int. Ed. Engl.*, 1991, 30, 613–629.

Franson et al., "Phospholipid metabolism by phagocytic cells. Phospholipases $A_2$ associated with rabbit polymorphonuclear leukocyte granules", *J. Lipid Res.*, 1974, 15, 380–388.

Geysen et al., "Strategies for epitope analysis using peptide synthesis", *J. Immunol. Methods*, 1987, 102, 259–274.

Glaser et al., "Phospholipase $A_2$ enzymes: regulation and inhibition", *TiPS*, 1993, 14, 92–98.

Grainger et al., "An enzyme caught in action: direct imaging of hydrolytic function and domain formation of phospholipase $A_2$ in phosphatidylcholine monolayers", *FEBS Lett.*, 1989, 252(1,2), 73–82.

Green and Wuts, *Protective Groups in Organic Synthesis*, John Wiley & Sons, New York, 2d edition, 1991.

Groves, et al., CA, 1984, 100:57365.

Houghten et al., "Generation and use of synthetic peptide combinatorial libraries for basic research and drug discovery", *Nature*, 1991, 354, 84–86.

Kroschwitz, J. I. (ed.), *Concise Encyclopedia of Polymer Science and Engineering*, John Wiley & Sons, 1990, 858–859.

Lombardo et al., "Cobra Venom Phospholipae $A_2$ Inhibition by Manoalide", *J. Biol. Chem.*, 1985, 260(12), 7234–7240.

Märki et al., "Differential inhibition of human secretory and cytosolic phospholipase $A_2$", *Agents Action*, 1993, 38, 202–211.

Mellor, D. P., "The Chelation of Heavy Metals", *Chemistry of Chelation and Chelating Agents in International Encyclopedia of Pharmacology and Therapeutics*, Levine, W.G., (ed.), Pergamon Press, Elmford, NY, Section 70, 1979.

Miyake et al., "The Novel Natural Product YM–26567–1 [(+)–trans–4–(3–dodecanoyl–2,4, 6–trihydroxyphenyl)–7–hydroxy–2–(4–hydroxyphenyl) chroman]: A Competitive Inhibitor of Group II Phospholipase $A_2$", *J. Pharm. Exp. Therap.*, 1992, 263(3), 1302–1307.

Noel et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.*, 1990, 112, 3704–3706.

Ohlmeyer et al., "Complex synthetic chemical libraries indexed with molecular tags", *Proc. Natl. Acad. Sci. USA*, 1993, 90, 10922–10926.

Oinuma et al., "Synthesis and Biological Evaluation of Substituted Benzenesulfonamides as Novel Potent Membrane–Bound Phospholipase $A_2$ Inhibitors", *J. Med. Chem.*, 1991, 34, 2260–2267.

Owens et al., "The Rapid Identification of HIV Protease Inhibitors Through the Synthesis and Screening of Defined Peptide Mixtures", *Biochem. Biophys. Res. Commun.*, 1991, 181(1),402–408.

Pon, R.T., "Solid–Phase Supports for Oligonucleotide Synthesis", *Methods in Molecular Biology: Protocols for Oligonucleotides and Analogs—Synthesis and Properties*, Agrawal, S.(ed.), Humana Press, Totowa, NJ, 1993, vol. 20, Ch. 19, 465–496.

Pruzanski et al., "Enzymatic Activity and Immunoreactivity of Extracellular Phospholipase $A_2$ in Inflammatory Synovial Fluids", *Inflamm.*, 1992, 16(5), 451–457.

Saari et al., "Cyclization–Activated Prodrugs. Basic Carbamates of 4–Hydroxyanisole", *J. Med. Chem.*, 1990, 33, 97–101.

Sampson et al., "Identification and Characterization of a New Gene of *Escherichia coli* K–12 Involved in Outer Membrane Permeability", *Genetics*, 1989, 122, 491–501.

Scott et al., "Interfacial Catalysis: The Mechanism of Phospholipase A2", *Science*, 1990, 250, 1541–1546.

Simon et al., "Peptoids: A modular approach to drug discovery", *Proc. Natl. Acad. Sci. USA*, 1992, 89, 9367–9371.

Tanaka et al., "A Novel Type of Phospholipase $A_2$ Inhibitor, Thielocin A1β, and Mechanism of Action", *J. Antibiotics*, 1992, 45(7), 1071–1078.

Vishwanath et al., "Edema–Inducing Activity of Phospholipase A2 Purified From Human Synovial Fluid and Inhibition by Aristolochic Acid", *Inflamm.*, 1988, 12(6), 549–561.

Washburn et al., "Suicide–inhibitory Bifunctionally Linked Substrates (SIBLINKS) as Phospholipase $A_2$ Inhibitors", *J. Biol. Chem.*, 1991, 266(8), 5042–5048.

Wery et al., "Structure of recombinant human rheumatoid arthritic synovial fluid phospholipase $A_2$ at 2.2 Å resolution", *Nature*, 1991, 352, 79–82.

Wright et al., "Large Scale Synthesis of Oligonucleotides via Phosphoramidite Nucleosides and a High–loaded Polystyrene Support", *Tetra. Lett.*, 1993, 34(21), 3373–3376.

Wyatt et al., "Combinatorially selected guanosine–quartet structure is a potent inhibitor of human immunodeficiency virus envelope–mediated cell fusion", *Proc. Natl. Acad. Sci. USA*, 1994, 91, 1356–1360.

Yamamoto et al., "One–step Synthesis of 5'–Azido–nucleosides", *J. Chem. Soc. Perkin 1*, 1980, 306–310.

Yang et al., "Studies on the status of lysine residues in phospholipase $A_2$ from Naja naja atra (Taiwan cobra) snake venom", *Biochem. J.*, 1989, 262, 855–860.

Yuan et al., "Synthesis and Evaluation of Phospholipid Analogues as Inhibitors of Cobra Venom Phospholipase $A_2$", *J. Am. Chem. Soc.*, 1987, 109, 8071–8081.

Zuckermann, et al., "Efficient Method for the Preparation of Peptoids [Oligo(N–substituted glycines)] by Submonomer Solid–Phase Synthesis", *J. Am. Chem. Soc.*, 1992, 114, 10646–10647.

* cited by examiner

Letters used in figures 2 through 10

| #  | R   | Ra    | Rb    | Rc   | Rd   |
|----|-----|-------|-------|------|------|
| 8  | $L_1$ | $L_{14}$ | $L_{14}$ | H    | $L_{14}$ |
| 9  | $L_3$ | $L_3$  | $L_3$  | $L_3$  | H    |
| 10 | $L_1$ | $L_4$  | $L_4$  | $L_4$  | H    |
| 11 | $L_1$ | H, $L_4$ | H, $L_4$ | $L_4$  | H    |
| 12 | $L_2$ | $L_4$  | $L_4$  | $L_4$  | H    |
| 13 | $L_2$ | $L_4$  | $L_4$  | $L_4$  | $L_5$  |

| # | R | Ra | Rb | Rc | Rd |
|---|---|---|---|---|---|
| 18 | $L_1$ | $L_{3,4,6-9}$ | $L_{3,4,6-9}$ | $L_{3,4,6-9}$ | H |
| 19 | $L_2$ | $L_{3,4,6-9}$ | $L_{3,4,6-9}$ | $L_{3,4,6-9}$ | H |
| 20 | H | $L_{3,4,6-9}$ | $L_{3,4,6-9}$ | $L_{3,4,6-9}$ | H |
| 21 | $L_3$ | $L_{3,4,6-9}$ | $L_{3,4,6-9}$ | $L_{3,4,6-9}$ | H |
| 22 | $L_6$ | $L_{3,4,6-9}$ | $L_{3,4,6-9}$ | $L_{3,4,6-9}$ | H |
| 23 | $L_7$ | $L_{3,4,6-9}$ | $L_{3,4,6-9}$ | $L_{3,4,6-9}$ | H |
| 24 | $L_8$ | $L_{3,4,6-9}$ | $L_{3,4,6-9}$ | $L_{3,4,6-9}$ | H |
| 25 | $L_4$ | $L_{3,4,6-9}$ | $L_{3,4,6-9}$ | $L_{3,4,6-9}$ | H |
| 26 | $L_9$ | $L_{3,4,6-9}$ | $L_{3,4,6-9}$ | $L_{3,4,6-9}$ | H |
| 27 | $L_{10}$ | $L_{3,4,6-9}$ | $L_{3,4,6-9}$ | $L_{3,4,6-9}$ | H |
| 28 | $L_{11}$ | $L_{3,4,6-9}$ | $L_{3,4,6-9}$ | $L_{3,4,6-9}$ | H |
| 29 | $L_{12}$ | $L_{3,4,6-9}$ | $L_{3,4,6-9}$ | $L_{3,4,6-9}$ | H |
| 30 | $L_{13}$ | $L_{3,4,6-9}$ | $L_{3,4,6-9}$ | $L_{3,4,6-9}$ | H |

49

50

$L_n$ = one letter
or a mixture of
letters in a library

51

52

53

54

55

$L_n$ = one letter
or a mixture of
letters in a library

COMPOUNDS HAVING A PLURALITY OF NITROGENOUS SUBSTITUTENTS

CROSS REFERENCE TO RELATED APPLICATIONS

This application is the National Stage of International Application No. PCT/US97/13530, filed Aug. 1, 1997, which is a continuation-in-part of U.S. application Ser. No. 08/691,206, filed Aug. 1, 1996, now U.S. Pat. No. 6,077,954.

FIELD OF THE INVENTION

The present invention relates to nitrogenous compounds and combinations thereof, that have a central aromatic, alicyclic, or heterocyclic ring system that is substituted with at least two linear groups, and which contain a plurality of nitrogenous moieties. The nitrogenous moieties are functionalized to bear chemical functional groups, which introduce points of diversity into the compounds. The constituent compounds have diverse chemical functional groups, giving each compound of the mixtures at least one property that renders it diverse as compared to the other compounds. The combinatorial libraries are deconvoluted to compounds having unique desirable properties.

Such libraries are useful inter alia for antibacterial pharmaceutical use. They are also useful for identifying metal chelating species for "heavy metal" therapy and the like, as well as for industrial application. Imaging agents can also be provided through the present invention.

BACKGROUND OF THE INVENTION

Traditional processes of drug discovery involve the screening of biological mixtures such as complex fermentation broths and plant extracts for a desired biological activity, or the chemical synthesis of large numbers of new compounds for evaluation as potential drugs. The advantage of screening mixtures from biological sources is that a large number of compounds are screened simultaneously, in some cases leading to the discovery of novel and complex natural products with activities that could not have been predicted otherwise. The disadvantages of this technique are that many different samples must be screened, and numerous purifications must be carried out to identify the active component, which is often present only in trace amounts. An advantage of laboratory synthesis of potential drug candidates is that unambiguous products are produced, but the preparation of each new structure requires significant expenditure of resources. Additionally, the de novo design of active compounds based on the high resolution structures of enzymes has generally not been successful.

It is now widely appreciated that combinatorial libraries are useful per se and that such libraries, and compounds of which they are comprised, have great commercial importance. Indeed, a new industry has arisen to exploit the many commercial aspects of combinatorial libraries.

In order to maximize the advantages of each classical approach, new strategies for combinatorial deconvolution have been developed independently by several groups. Selection techniques have been used with libraries of peptides (Geysen, H. M., Rodda, S. J., Mason, T. J., Tribbick, G. and Schoofs, P. G., *J. Immun. Meth.* 1987, 102, 259–274; Houghten, R. A., Pinilla, C., Blondelle, S. E., Appel, J. R., Dooley, C. T. and Cuervo, J. H., *Nature,* 1991, 354, 84–86; Owens, R. A., Gesellchen, P. D., Houchins, B. J. and DiMarchi, R. D., *Biochem. Biophys. Res. Commun.,* 1991, 181, 402–408; Doyle, M. V., PCT WO 94/28424; Brennan, T. M., PCT WO 94/27719); nucleic acids (Wyatt, J. R., et al., *Proc. Natl. Acad. Sci. USA,* 1994, 91, 1356–1360; Ecker, D. J., Vickers, T. A., Hanecak, R., Driver, V. and Anderson, K., *Nucleic Acids Res.,* 1993, 21, 1853–1856); nonpeptides and small molecules (Simon, R. J., et al., *Proc. Natl. Acad. Sci. USA,* 1992, 89, 9367–9371; Zuckermann, R. N., et al., *J. Amer. Chem. Soc.,* 1992, 114, 10646–10647; Bartlett, Santi, Simon, PCT WO91/19735; Ohlmeyer, M. H., et al., *Proc. Natl. Acad. Sci. USA*, 1993, 90, 10922–10926; DeWitt, S. H., Kiely, J. S., Stankovic, C. J., Schroeder, M. C. Reynolds Cody, D. M. and Pavia, M. R., *Proc. Natl. Acad. Sci. USA,* 1993, 90, 6909–6913; Cody et al., U.S. Pat. No. 5,324,483; Houghten et al., PCT WO 94/26775; Ellman, U.S. Pat. No. 5,288,514; Still et al., PCT WO 94/08051; Kauffman et al., PCT WO 94/24314; Carell, T., Wintner, D. A., Bashir-Hashemi, A. and Rebek, J., *Angew. Chem. Int. Ed. Engel.,* 1994, 33, 2059–2061; Carell, T., Wintner, D. A. and Rebek, J., *Angew. Chem. Int. Ed. Engel.,* 1994, 33, 2061–2064; Lebl, et al., PCT WO 94/28028). We have developed certain nitrogen coupled chemistries that we have utilized to prepare a class of compounds we refer to as "oligonucleotides." These compounds have been described in previous patent applications, all of which are incorporated herein by reference, including published PCT applications WO 92/20822 (PCT US92/04294) and WO 94/22454 (PCT US94/03313). These chemistries include compounds having amine linkages, hydroxylamine linkages, hydrazino linkages and other nitrogen based linkages.

A review of the above references reveals that the most advanced of these techniques are those for selection of peptides and nucleic acids. Several groups have reported the selection of heterocycles such as benzodiazepines. However, with the exception of Rebek et al., scant attention has been given to combinatorial discovery of other types of molecules.

The majority of the techniques reported to date involve iterative synthesis and screening of increasingly simplified subsets of oligomers. Monomers or sub-monomers that have been utilized include amino acids, amino acid-like molecules, i.e. carbamate precursors, and nucleotides, both of which are bifunctional. Utilizing these techniques, libraries have been assayed for activity in either cell-based assays, or for binding and/or inhibition of purified protein targets.

A technique, called SURFT™ (Synthetic Unrandomization of Randomized Fragments), involves the synthesis of subsets of oligomers containing a known residue at one fixed position and equimolar mixtures of residues at all other positions. For a library of oligomers four residues long containing three monomers (A, B, C), three subsets would be synthesized (NNAN, NNBN, NNCN, where N represents substantially equal incorporation of each of the three monomers). Each subset is then screened in a functional assay and the best subset is identified (e.g. NNAN). A second set of libraries is synthesized and screened, each containing the fixed residue from the previous round, and a second fixed residue (e.g. ANAN, BNAN, CNAN). Through successive rounds of screening and synthesis, a unique sequence with activity in the functional assay can be identified. The SURF™ technique is described in Ecker, D. J., Vickers, T. A., Hanecak, R., Driver, V. & Anderson, K., *Nucleic Acids Res.,* 1993, 21, 1853–1856. The SURF™ method is further described in PCT patent application WO 93/04204, the entire disclosure of which is herein incorporated by reference.

The combinatorial chemical approach that has been most utilized to date, utilizes an oligomerization from a solid support using monomeric units and a defined connecting chemistry, i.e. a solid support monomer approach. This approach has been utilized in the synthesis of libraries of peptides, peptoids, carbamates and vinylogous peptides connected by amide or carbamate linkages or nucleic acids connected by phosphate linkages as exemplified by the citations listed above. A mixture of oligomers (pool or library) is obtained from the addition of a mixture of activated monomers during the coupling step or from the coupling of individual monomers with a portion of the support (bead splitting) followed by remixing of the support and subsequent splitting for the next coupling. In this monomeric approach, each monomeric unit would carry a tethered letter, i.e., a functional group for interaction with the target. Further coupling chemistry that allows for the insertion of a tethered letter at a chemically activated intermediate stage is referred to as the sub-monomer approach.

The diversity of the oligomeric pool is represented by the inherent physical properties of each monomer, the number of different monomers mixed at each coupling, the physical properties of the chemical bonds arising from the coupling chemistry (the backbone), the number of couplings (length of oligomer), and the interactions of the backbone and monomer chemistries. Taken together, these interactions provide a unique conformation for each individual molecule.

There remains a need in the art for molecules which have fixed preorganized geometry that matches those of targets such as proteins and enzymes, nucleic acids, lipids and other targets. The backbones of such molecules should be rigid with some flexibility, and such molecules should be easy to construct in solution or via automated synthesis on a solid support.

OBJECTS OF THE INVENTION

It is an object of the invention to provide compounds for diagnostic, research, and therapeutic use.

It is a further object of the invention to provide compounds that have a plurality of nitrogenous sites for introducing chemical functional groups which provide "diversity" to the compounds of the invention.

It is yet another object of the invention to provide methods for preparing libraries of diversified compounds.

It is a still further object of the invention to provide libraries of combinatorialized compounds.

These and other objects will become apparent to persons of ordinary skill in the art from a review of the present specification and the appended claims.

SUMMARY OF THE INVENTION

The present invention provides novel compounds having a central ring or ring system to which is covalently attached at least 2 substituent groups containing nitrogenous sites which bear chemical functional groups.

In certain embodiments, compounds of the invention have the formula:

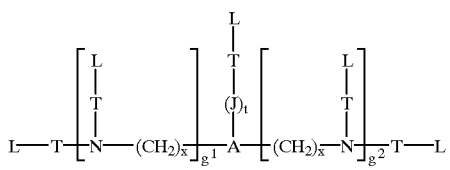

wherein:
$g^1$ is 1 to about 4;
$g^2$ is 2 to about 4;
A is an aromatic, heterocyclic, or alicyclic ring system;
each x is, independently, 1 to about 8;
J is N, O, S, or a heterocyclic ring system having at least one nitrogen;
t is 0 or 1;
each T is, independently, a single bond, a methylene group or a group having the formula:

each $R^1$, $R^2$ and $R^3$ is, independently, H, alkyl or haloalkyl having 1 to about 10 carbon atoms, alkenyl having 2 to about 10 carbon atoms, alkynyl having 2 to about 10 carbon atoms, or aryl having 6 to about 14 carbon atoms;
each $R^5$ and E is, independently, a single bond, CH=CH, C≡C, O, S, $NR^3$, SO, $C_6$–$C_{14}$ aryl, substituted $C_6$–$C_{14}$ aryl, heteroaryl, substituted heteroaryl, a nitrogen, oxygen, or sulfur containing heterocycle; a substituted nitrogen, oxygen, or sulfur containing heterocycle; a mixed heterocycle; or a substituted mixed heterocycle; where said substituent groups are selected from hydroxyl (OH), alkoxy, alcohol, benzyl, phenyl, nitro ($NO_2$), thiol (SH), thioalkoxy, halogen, alkyl, aryl, alkenyl, and alkynyl groups;
each $R^6$ is =O, =S, =$NR^3$;
each m and n is, independently, zero to 5;
each p is, independently, zero or 1;
q is 1 to about 10;
each L is, independently, H, $C_1$–$C_{10}$ alkyl or substituted alkyl; $C_2$–$C_{10}$ alkenyl or substituted alkenyl; $C_2$–C alkynyl or substituted alkynyl; $C_4$–$C_7$ carbocyclic alkyl or substituted carbocyclic alkyl; alkenyl carbocyclic; substituted alkenyl carbocyclic; alkynyl carbocyclic; substituted alkynyl carbocyclic; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from alkyl, alkenyl, alkynyl, aryl, hydroxyl, alkoxy, alcohol, benzyl, nitro, thiol, thioalkyl, thioalkoxy, trifluoromethyl or halogen groups; or L is phthalimido, an ether having 2 to 10 carbon atoms and 1 to 4 oxygen or sulfur atoms, a metal coordination group, a conjugate group, halogen, hydroxyl, thiol., keto, carboxyl, $NR^1R^2$, $CONR^1$, amidine (C(=NH)$NR^2R^3$), guanidine (NHC(=NH)$NR^2R^3$), glutamyl ($R^1$OOCCH($NR^2R^3$)($CH_2$)$_2$C (=O) nitrate, nitro, nitrile, trifluoromethyl, trifluoromethoxy, NH-alkyl, N-dialkyl, O-aralkyl, S-aralkyl, NH-aralkyl, azido ($N_3$), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a drug, or a group capable of hydrogen bonding; and with the proviso that when A is 2,6-disubstituted pyridine with $g^1$ equal to 2 and $g^2$ equal to 2, and having 6 of said L groups, then not more than 3 of said L groups are H or para-toluenesulfonyl.

In some embodiments of the invention compounds are provided wherein $g^1$ is not equal to $g^2$, In other embodiment compounds are provided wherein $g^1$ is 1 and $g^2$ is 2. In further embodiments compounds are provided wherein $g^1$ is 1 and $g^2$ is 3.

In other embodiments of the invention compounds are provided wherein at least 3 of the L groups are different from each other. In further embodiments at least 4 of said L groups are different from each other. In yet further embodiments compounds are provided wherein at least one of said L groups is phthalimido.

In some embodiments of the invention compounds are provided wherein t is 1 and J is a heterocyclic ring system. In a preferred embodiment the heterocyclic ring system is piperazine.

In some preferred embodiments of the invention compounds are provided wherein A is benzene, naphthalene, anthracene, cyclohexane, cyclopentane or adamantane. In other preferred embodiments compounds are provided wherein A comprises a nitrogen, oxygen or sulfur containing heterocycle, preferably furan, pyran thiophene, aziridine, azetine, pyridine, 1,3,5-triazine, a-triazine, as-triazine, cyanuric acid, pyrrole, pyrazole, 1,2,3-triazole, imidazole, pyrimidine, purine, piperidine, pyrazole, pyrrolidine, piperazine, pyrazine, pyridazine, morpholine, oxazole, isoxazole, thiazole, or isothiazole.

In further embodiments of the invention compounds are provided wherein the sum of $g^1$ and $g^2$ is from 3 to 8, or the sum of $g^2$ and $g^2$ is from 3 to 6, or sum of $g^1$ and $g^2$ is from 3 to 4. In still further embodiments compounds are provided wherein the sum of $g^1$ added to $g^2$ is an odd number from 3 to 7.

The present invention provides novel libraries comprising aromatic compounds having at least 2 substituent groups containing nitrogenous sites bearing chemical functional groups. In certain embodiments libraries are provided comprising a plurality of chemically diverse compounds having the formula:

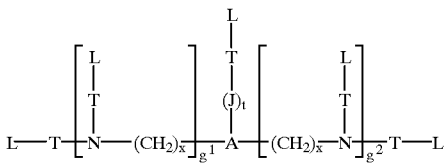

wherein:
$g^1$ is from 1 to about 4;
$g^2$ is from 2 to about 4;
A is an aromatic, heterocyclic, or alicyclic ring system;
each x is, independently, from 1 to about 8;
J is N, O, S, or a heterocyclic ring system having at least one nitrogen;
t is 0 or 1;
T is a single bond, a methylene group or a group having the structure:

each $R^1$, $R^2$ and $R^3$ is, independently, H, alkyl or haloalkyl having 1 to about 10 carbon atoms, alkenyl having 2 to about 10 carbon atoms, alkynyl having 2 to about 10 carbon atoms, or aryl having 6 to about 14 carbon atoms;
each $R^1$ and E is, independently, a single bond; CH=CH; C≡C; O; S; $NR^3$; $SO_2$; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from hydroxyl (OH), alkoxy, alcohol, benzyl, phenyl, nitro ($NO_2$), thiol (SH), thioalkoxy, halogen, alkyl, aryl, alkenyl, and alkynyl groups;
each $R^6$ is =O, =S, =$NR^3$;
each m and n is, independently, zero to 5;
each p is, independently, zero or 1;
q is 1 to about 10; and
each L is, independently, H, $C_1$–$C_{10}$ alkyl; substituted alkyl; $C_2$–$C_{10}$ alkenyl; substituted alkenyl; $C_2$–$C_{10}$ alkynyl; substituted alkynyl; $C_4$–$C_7$ carbocyclic alkyl; substituted carbocyclic alkyl; alkenyl carbocyclic; substituted alkenyl carbocyclic; alkynyl carbocyclic; substituted alkynyl carbocyclic; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from alkyl, alkenyl, alkynyl, aryl, hydroxyl, alkoxy, alcohol, benzyl, nitro, thiol, thioalkyl, thioalkoxy, trifluoromethyl or halogen groups; or L is phthalimido, an ether having 2 to 10 carbon atoms and 1 to 4 oxygen or sulfur atoms, a metal coordination group, a conjugate group, halogen, hydroxyl, thiol, keto, carboxyl, $NR^1R^2$, $CONR^1$, amidine (C (=NH)$NR^2R^3$), guanidine (NHC (=NH)$NR^2R^3$), glutamyl ($R^1OOCCH(NR^2R^3)(CH_2)_2C(=O)$), nitrate, nitro, nitrile, trifluoromethyl, trifluoromethoxy, NH-alkyl, N-dialkyl, O-aralkyl, S-aralkyl, NH-aralkyl, azido ($N_3$), hydrazino ($NHNH_2$) hydroxylamino ($ONH_2$), sulfoxide (SO), sulfone ($SO_2$), sulfide (S—), disulfide (S—S), silyl, a nucleosidic base, an amino acid side chain, a carbohydrate, a drug, or a group capable of hydrogen bonding.

In one embodiment of the invention libraries are provided having a plurality of chemically diverse compounds which differ from each other by having different T—L groups or by having T—L— groups in different locations on the compound.

In other embodiments of the invention libraries are provided wherein $g^1$ is not equal to $g^2$. In further embodiments libraries are provided wherein $g^1$ is 1 and $g^2$ is 2. In still further embodiments libraries are provided wherein $g^1$ is 1 and $g^2$ is 3.

In one preferred embodiment of the invention libraries are provided wherein at least 3 of said —T—L groups are different. In another preferred embodiment libraries are provided wherein at least 4 of said —T—L groups are different.

In even further embodiments of the invention libraries are provided wherein t is 1 and J is a heterocyclic ring system. In a preferred embodiment the heterocyclic ring system is piperazine.

In further embodiments of the invention methods are provided for generating a library of compounds having diverse properties, which have the formula:

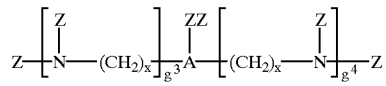

wherein:
$g^3$ is from 1 to about 4;
$g^4$ is from 2 to about 4;
A is an aromatic, heterocyclic, or alicyclic ring system;
each x is, independently, from 1 to about 8;

ZZ is H, a nitrogen protecting group, a heterocyclic ring system having at least one nitrogen that is protected, or a group having the formula —(J)t—T—L;

each Z is, independently, H or a nitrogen protecting group with the proviso that at least one Z is H;

selecting a plurality of chemical functional group reactants of the formula:

XX—T—L wherein:
XX is a reactive moiety capable of reacting to form a covalent bond between the T of T—L and a nitrogen;
J is N, O, S, or a heterocyclic ring system having at least one nitrogen;
t is 0 or 1;
T is a single bond, a methylene group or a group having the formula:

each $R^1$, $R^2$ and $R^3$ is, independently, H, alkyl or haloalkyl having 1 to about 10 carbon atoms, alkenyl having 2 to about 10 carbon atoms, alkynyl having 2 to about 10 carbon atoms, or aryl having 6 to about 14 carbon atoms;

each $R^5$ and E is, independently, a single bond; CH=CH; C≡C; O; S; $NR^3$; $SO_2$; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from hydroxyl (OH), alkoxy, alcohol, benzyl, phenyl, nitro ($NO_2$), thiol (SH), thioalkoxy, halogen, alkyl, aryl, alkenyl, and alkynyl groups;

each $R^6$ is =O, =S, =$NR^3$;

each m and n is, independently, zero to 5;

each p is, independently, zero or 1;

q is 1 to about 10;

each L is, independently, H, $C_1$–$C_{10}$ alkyl; substituted alkyl; $C_2$–$C_{10}$ alkenyl; substituted alkenyl; $C_2$–$C_{10}$ alkynyl; substituted alkynyl; $C_4$–$C_7$ carbocyclic alkyl; substituted carbocyclic alkyl; alkenyl carbocyclic; substituted alkenyl carbocyclic; alkynyl carbocyclic; substituted alkynyl carbocyclic; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from alkyl, alkenyl, alkynyl, aryl, hydroxyl, alkoxy, alcohol, benzyl, nitro, thiol, thioalkyl, thioalkoxy, trifluoromethyl or halogen groups; or L is phthalimido, an ether having 2 to 10 carbon atoms and 1 to 4 oxygen or sulfur atoms, a metal coordination group, a conjugate group, halogen, hydroxyl, thiol, keto, carboxyl, $NR^1R^2$, $CONR^1$, amidine ($C(=NH)NR^2R^3$), guanidine ($NHC(=NH)NR^2R^3$), glutamyl ($R^1OOCCH(NR^2R^3)(CH_2)_2C(=O)$) nitrate, nitro, nitrile, trifluoromethyl, trifluoromethoxy, NH-alkyl, N-dialkyl, O-aralkyl, S-aralkyl, NH-aralkyl, azido ($N_3$), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a drug, or a group capable of hydrogen bonding; and reacting said chemical functional group reactants with said substituted cyclic compound to form covalent bonds between said T groups of said chemical functional group reactants and unprotected nitrogen groups on said substituted cyclic compounds.

In one embodiment of the invention the method for generating a library of compounds having diverse properties further comprises selectively deprotecting at least one of the nitrogen protecting groups to give at least one deprotected nitrogen. In further embodiments the method further comprises reacting at least one deprotected nitrogen with a further chemical functional group reactant of the formula:

XX—T—L thereby forming a covalent bond between said —T—L group and said nitrogen.

In preferred embodiments of the invention each nitrogen is an amine, hydroxylamine, amides, hydrazide, carbamate, urea, hydrazine, sulfonamide, sulfanamide or sulfinamide.

In another embodiment of the invention the ring system is heteroaromatic, preferably aziridine, azetine, pyridine, 1,3,5-triazine, a-triazine, as-triazine, cyanuric acid, pyrrole, pyrazole, 1,2,3-triazole, imidazole, pyrimidine, purine, piperidine, pyrazole, pyrrolidine, piperazine, pyrazine, pyridazine, morpholine, oxazole, isoxazole, thiazole, isothiazole, furan, pyran, thiophene, benzene, naphthalene, anthracene, cyclohexane, cyclopentane or adamantane.

In a further embodiment of the invention each chemical functional group reactant is an aldehyde, ketone, acid, acid halide, halide, acid anhydride, isocyanate, isothiocyanate, chloroformate or activated ester.

In some embodiments of the invention the method for generating a library of compounds having diverse properties is effected by iterative reaction of nitrogens with the chemical functional group reactants. In other embodiments the chemical functional group reactants are reacted with the nitrogens iteratively, and in each of the iterative reactions, each of the chemical functional group reactants are reacted with the nitrogen essentially simultaneously. In further embodiments of the invention the chemical functional group reactants are reacted with the nitrogens in a single reaction step.

BRIEF DESCRIPTION OF THE DRAWINGS

The numerous objects and advantages of the present invention may be better understood by those skilled in the art by reference to the accompanying figures, in which.

DETAILED DESCRIPTION OF THE PREFERRED EMBODIMENTS

Figure 1:
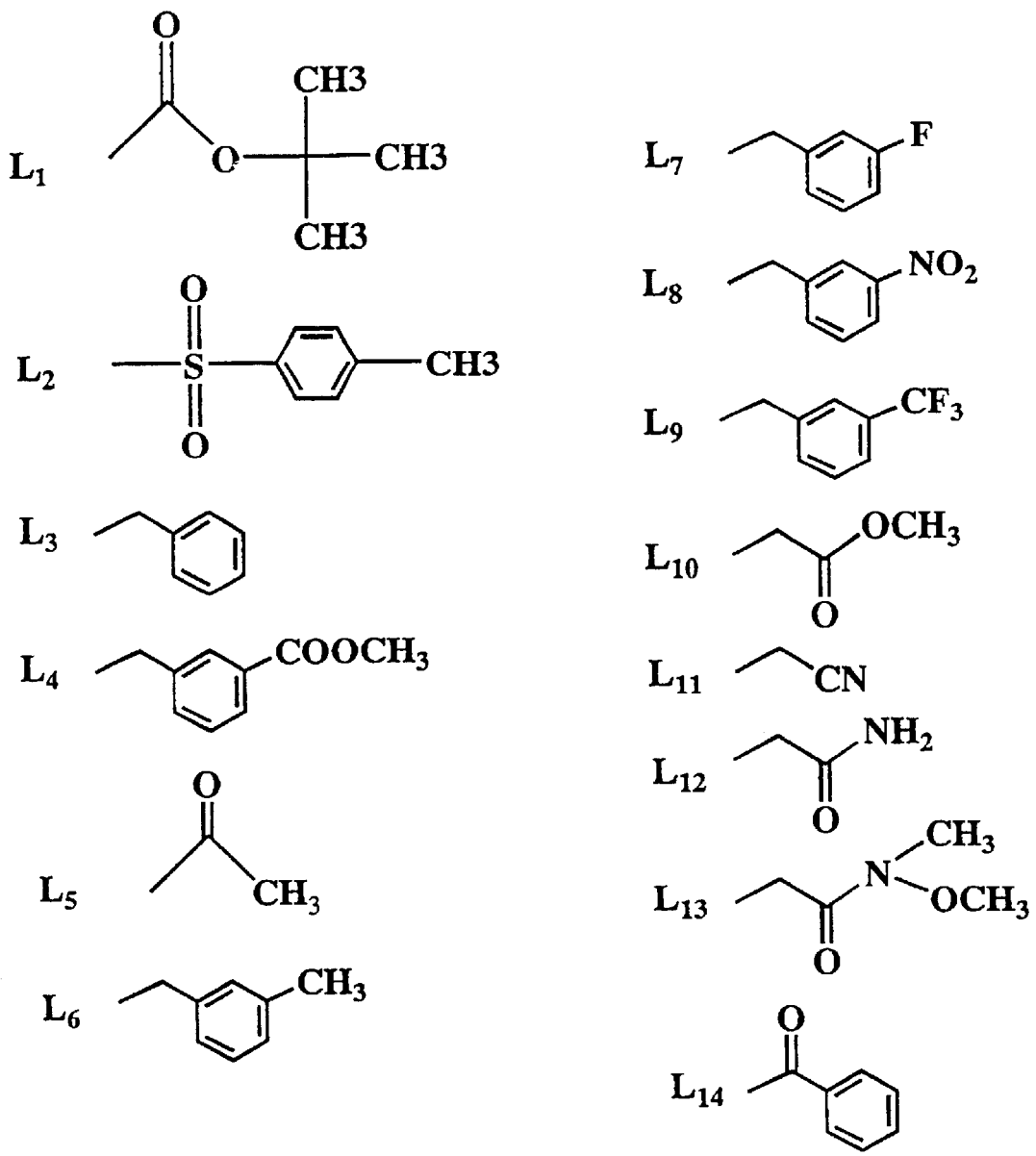
FIG. 1 is a representative list of some of the "letters" amenable to the present invention.

The present invention relates to compounds having a central ring system, and two covalently attached substituent groups that contain a plurality of functionalized nitrogenous moieties, and to combinatorial libraries consisting of the compounds. The central ring system can be aromatic, alicyclic, or heterocyclic single or multiple-ring structure. The nitrogenous moieties are sites which are functionalized to bear functional groups (pendant groups), which impart diversity characteristics to the compound. The nitrogenous moieties (also referred to as "sites") can also be located in the central ring system of compounds of the invention, either as ring nitrogen atoms, or appended to the ring system. Each nitrogenous moiety can be derivatized with one or two chemical functional groups, which can selected from a variety of chemical functional groups. Libraries of such compounds having various permutations and combinations of chemical functional groups and nitrogenous sites can be prepared and used in standard biological assays, such as standard antibiotic assays.

Preferred compounds of the invention include a central heterocyclic aromatic compound substituted with two linear groups having at least 3 nitrogenous sites substituted with chemical functional groups, and a third substituent having 1 nitrogenous site substituted with a chemical functional group. More preferred compounds of the invention include a central heterocyclic aromatic compound substituted with two linear groups having at least 3 nitrogenous sites substituted with chemical functional groups.

The pendent chemical functional groups on the compounds of the invention provide for binding of the compounds to proteins, including enzymes, nucleic acids, lipids and other biological targets.

In preferred embodiments of the invention, chemical functional groups are bound to nitrogenous moieties by reacting the nitrogenous moieties with chemical functional group reactants (referred to herein as "ated compounds"), which are activated forms of the chemical functional groups. As used herein, a "chemical functional group" is a chemical group that, when attached to a parent molecule, imparts to that molecule a particular and unique characteristic, thus contributing diversity to the parent molecule by rendering the parent molecule different in some way from what it was before attachment of the group. Several chemical functional groups can be attached to a particular molecule, and, when considered together, the sum total of their properties will impart global diversity characteristics to the parent molecule. Each set of combinations of chemical functional groups on a particular molecule will modify the parent such that the parent molecule having each particular combination of groups will be different from the parent molecule having any of the other combinations of groups. A combinatorial library according to the invention is the set of compounds which includes all of the combinations of the chemical functional groups on the parent molecule.

Compounds of the invention can be synthesized with both the position and the choice of the chemical functional groups predetermined, or the position and the choice of the chemical functional groups can be selected by combinatorial selection. In the context of this invention, "combinatorial" does not mean arbitrary, haphazard or indiscriminate. In the context of this invention, "combinatorial" is construed to mean that within the totality of the population of molecules that can be formed using a particular set of chemical functional groups and a particular nitrogenous moiety, there will be sub-populations of each of the possible species. Thus, each of the different combinations of a) choice of chemical functional group and b) positioning of the chemical functional groups will be represented.

"Combinatorial" is distinct from "random." To illustrate the distinction, if all or nearly all possible combinations are present in the total molecular population, then it is a combinatorial population of molecules. If, however, only one or a small number of molecules from that total population is selected, then the selected molecule or molecules might be randomly selected if it is picked at whim or will from the total population. When the totality of the population is considered, all species are present and it is not a random population. If a systematic selection was made until the totality of the population was exhausted, then all of the species would eventually be selected, however, the order of selection might be random. Thus, in certain preferred embodiments, a pre-ordered selection and/or location of chemical functional groups will be present. In further preferred embodiments, a combinatorialized population of all possible combinations and ordering of the chemical functional groups is present. In even further preferred embodiments, the sequence is modulated between fixed and combinatorial. This is especially useful, as for example, in certain deconvolution strategies.

"Deconvolution" is construed to mean taking the totality of a population and systematically working through that population to establish the identity of a particular member, selected members, or all members of the population. In deconvoluting a combinatorial library of compounds, systematic selection is practiced until an individual compound or a group of individual compounds having a particular characteristic, as for instance being an active species in a specific functional assay, is identified.

The compounds of the invention are prepared by modification of nitrogenous moieties by reaction with chemical functional group reactants. Chemical functional group reactants (or "reactant compounds") are compounds that contain both a site that is capable of reaction with a nitrogen atom of a nitrogenous moiety, and a further chemical functional group that serves to impart diversity to both the reactant compound, and to any molecule to which it might be covalently bonded. Reaction between a reactant compound and a nitrogenous moiety produces a covalent bond between the chemical functional group and the nitrogen atom of the nitrogenous site. This covalent bonding of the chemical functional group to the nitrogen atom of the nitrogenous moiety introduces a point of functionality or point of diversity at that particular nitrogen atom. Alternatively, a particular nitrogenous moiety might include a "null" in place of the functional group, i.e. it might lack a functional group. This is accomplished by having a hydrogen atom covalently bonded to the nitrogen atom or by having a double bond between the nitrogen atom and an adjacent atom, e.g. as an oxime or imine.

The reactant compounds may also include a tether giving a further element of diversity to the functional groups. Hence, the incoming reactant compound bearing a chemical functional moiety imparts diversity to the compounds of the invention and, upon bonding to a nitrogenous site, its residue can be referred to as a pendant chemical functional group.

The covalent bonding of chemical functional groups to the nitrogenous sites of the compounds of the invention yields compounds having unique sets of properties. These properties include the overall global shape, the conformational space, electron density, dipole moment and ability of the compound to interact with enzyme pockets and other binding sites and other similar properties.

In one embodiment, compounds of the invention include a ring system and two linear substituents. The ring system can be an aromatic ring system, a heterocyclic ring system, an alicyclic ring system, or a mixed ring system such as an araalicyclic ring system (i.e., mixed aromatic-alicyclic, such as tetralin or fluorene) ring system. The linear substituent groups contain nitrogenous sites that are substituted with chemical functional groups. Nitrogenous sites are separated from the ring system and other nitrogenous sites by at least one methylene group. Preferably, one of the linear substituents contains at least 2 nitrogenous sites, and the other contains at least 1 nitrogenous site.

Further nitrogenous moieties can reside in the central ring system or can be appended to the central ring system through, for example, a tether. In some embodiments, a nitrogenous moiety is present in a heterocyclic ring system that is covalently bound to the central ring system. In other embodiments a nitrogenous moiety is appended by a tether group to a central ring system through a N, O, or S heteroatom that is appended directly to the ring system.

Nitrogenous moieties residing in the ring system include constituent nitrogen atoms of heterocyclic rings. In certain preferred embodiments of the invention, the central ring system is an aromatic nitrogen heterocycle having one or more nitrogens such as, for example, pyridine, acridine or pyrimidine, or an aliphatic nitrogen heterocycle or a non-aromatic nitrogen heterocycle, such as piperidine, that is derivatized with chemical functional groups. In other preferred embodiments, no chemical functional groups are included on the ring nitrogens of the heterocycle.

In some preferred embodiments the compounds of the invention will have from 3 to 9 nitrogenous moieties. In other preferred compounds of the invention, there will be from 3 to 6 nitrogenous moieties. A preferably, there will be from 3 to 4 nitrogenous moieties.

In the context of this invention, a heterocyclic ring system includes single ring compounds as well as multi-ring compounds. Heterocyclic ring systems may be saturated, partially saturated, or unsaturated and will contain at least one hetero atom such as N, O, or S.

Illustrative non-heterocyclic ring systems useful in compounds of the invention include, but are not limited to, benzene, cyclopentane, cyclohexane, cycloheptane, cyclooctane, cyclononane, cyclodecane, transcyclooctane, cyclooctyne, cyclohepta-1,3-diene, [10]annulene (cyclodecapentaene), and [9]annulene {cyclonona-1,3,5,7-tetraene}.

Illustrative monocyclic nitrogen heterocycles useful in compounds of the invention include, but are not limited to, cyanuric acid, aziridine, azetine 1,3-diazetidine, cyclopentaazane, pyrrole, pyrazole, imidazole, 1,2,3-triazole, 1,2,4-triazole, 1,2,3-triazine, 1,2,4-triazine, cyanuric acid, pyridine, pyridazine, piperidine, pyrrolidine, pyrimidine, pyrazine, piperazine, pyridazine, s-triazine, azepine, 1,2,4-triazepine, and azocine.

Illustrative oxygen heterocycles useful in compounds of the invention include, but are not limited to, furan, 1,4-pyran, 1,2-dioxane, 1,3-dioxane, oxepin, 1,3,5,7-tetraoxocane and 1,4,8,11-tetraoxacyclotetradecane. Illustrative sulfur heterocycles include, but are not limited to thiophene, thiepine, 1,4-thiazepine. Illustrative mixed heterocycles include, but are not limited to, 1,2,3-oxathiole, isoxazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,4-oxazine, 1,3,2-oxazine, 1,3,6-oxazine, 1,2,6-oxazine, 1,4-oxazine o-isoxazine, p-isoxazine, 1,2,5-oxathiazine, 1,2,6-oxthiazine, 1,4,2-oxadiazine, 1,3,5,2-oxadiazine, 1,4-thiazepine and morpholine.

For the purposes of this invention a ring system is defined to include one ring, or two or more rings, that are joined together to form an extended or condensed ring. Such ring systems include extended aromatic systems, alicyclic systems, araalicyclic systems, bicyclic Systems and even spiro systems. Examples include aromatic, alicyclic and mixed aromatic-alicyclic (araalicyclic) multiple ring systems, spiro systems, bicyclic systems, non-aromatic multiple ring systems such as adamantane, decalin, steroids and terpenes, including sesquiterpenes, diterpenes, triterpenes and tetraterpenes, and multiple ring heterocyclic systems. Illustrative carbon ring systems include, but are not limited to, naphthalene, tetrahydronaphthalene (tetralin), anthracene, phenanthrene, fluorene, pyrene, coronene, azulene, cluorene, benzonaphthene, benzo[8]annulene, pentalene, heptalene, octalene, indene, isoindene biphenyl, biphenylene and triphenylene condensed rings; spiropentane, spiro[2.4]heptane, spiro[4.5]decane, spiro[3.4]octane, dispiro[5.1.7.2]heptadecane spiro systems, bornane, norbornane, camphor, bicyclo[2.2.1]heptane, bicyclo[3.2.1]octane, 7-methylbicyclo[2.2.1]heptane and trans and cis-bicyclo[4.4.0]decane (trans and cis-decalin) bicyclic systems; carotenes, delta-3-carene, alpha-pinene, camphor, ascaridole, azulene, cadinene, beta-selinene, ambrein, beta-amyrin and lupeol terpenes; cholesterol, lanosterol, coprostanol, stigmasterol, ergosterol, calciferol, cholic acid, deoxycholic acid, estrone, estradiol, estratriol, progesterone, stilbestrol, testosterone, androsterone, deoxycorticosterone, cortisone and 17-hydroxycorticosterone steroids.

Illustrative multiple ring heterocyclic systems include, but are not limited to, carbazole, acridine, xanthene, purine, 1,4-benzisoxazine, 1,2-benzisoxazine, 30 3,1,4-benzoxazine, 2,3,1-benzoxazine, 1,4,2-benzoxazine, 1,3,2-benzoxazine, pyrido[4,3-b]pyridine, pyrido[3,2-b]pyridine, pyrido[3,4-b]pyridine, naphthyridine, quinazoline, cinnoline, isoquinoline, quinoline, 1,2-benzoyran, anthranil, benzoxazole, indoxazine, indolazine, pyrano[3,4-b]pyrrole, 1,5-pyridine, 2-isobenzole, indolenine, indole, isothionaphthene, thionaphthene, isobenzofuran, benzofuran, and 2,2'-bipyridine.

Preferred rings and ring systems include aziridine, azetine, pyridine, 1,3,5-triazine, a-triazine (or as-triazine,) cyanuric acid, pyrrole, pyrazole, 1,2,3-triazole, imidazole, pyrimidine, purine, piperidine, pyrazole, pyrrolidine, piperazine, pyrazine, pyridazine, morpholine, oxazole, isoxazole, thiazole, isothiazole, furan, pyran, thiophene, benzene, naphthalene, anthracene, cyclohexane, cyclopentane and adamantane.

The chemical functional groups appended to the nitrogenous moieties of the compounds of the invention can be of various structures that impart particular interactive properties to the compounds of the invention. These chemical functional groups can effect interactions of at least the following types: hydrogen-bond donors and acceptors, ionic, polar, hydrophobic, aromatic, electron donors and acceptors, pi bond stacking or metal binding. As a result of such interactions, the compounds of the invention have unique properties effecting the overall global shape, the conformational space, electron density, dipole moment and ability of the compound to interact with enzyme pockets and other binding sites and other similar properties. While not wishing to be bound by any theory, it is believed that placement of the chemical functional groups on the compounds of the invention "geometrically constrains" the molecules for better binding characteristics with target molecules.

The chemical functional groups can also be referred to as functional groups or as "letters," reflecting the fact that the different functional groups on the compounds of the invention are positioned in sequences (either predetermined or by combinatorial methods) much like letters of the alphabet. Letters can be "reactive" or "non-reactive." "Reactive" letters will interact with a target molecule in some manner (which need not, but can be predefined). "Non-reactive" letters are those which are not intended react with a target molecule, but, rather, serve to impart other properties to the molecule such as, for example, effecting or facilitating up-take, distribution, metabolism or identification. Although non-reactive letters are not primarily intended to interact with a target molecule, they may nevertheless may do so.

A first preferred group of chemical functional groups according to the invention includes H, $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocyclic alkyl or substituted carbocyclic alkyl, alkenyl carbocyclic or substituted alkenyl carbocyclic, alkynyl carbocyclic or substituted alkynyl carbocyclic, or $C_6$–$C_{14}$ aryl or substituted aryl where the substituent groups are selected from hydroxyl (OH), alkoxy, alcohol, benzyl, phenyl, nitro ($NO_2$), thiol (SH), thioalkoxy, halogen, alkyl, aryl, alkenyl, and alkynyl groups; or L is phthalimido, an ether having 2 to 10 carbon atoms and 1 to 4 oxygen or sulfur atoms, a nitrogen containing heterocycle, a sulfur containing heterocycle, an oxygen containing heterocycle, a metal coordination group, a conjugate group, halogen, hydroxyl, thiol, keto (C=O), carboxyl (COOH), amide ($CONR^1$), amidine (C(=NH)$NR^2R^3$), guanidine (NHC((=NH)$NR^2R^3$), glutamyl ($R^1OOCCH(NR^2R^3)(CH_2)_2C$(=O)), nitrate ($ONO_2$), nitro, nitrile (CN), trifluoromethyl ($CF_3$), trifluoromethoxy ($OCF_3$), O-alkyl, S-alkyl, NH-alkyl, N-dialkyl, O-aralkyl, S-aralkyl, NH-aralkyl, amino ($NH_2$), azido ($N_3$), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a drug, or a group capable of hydrogen bonding, where each $R^1$, $R^2$ and $R^3$ is, independently, H, alkyl or haloalkyl having 1 to about 10 carbon atoms, alkenyl having 2 to about 10 carbon atoms, alkynyl having 2 to about 10 carbon atoms, or aryl having 6 to about 14 carbon atoms.

Heterocycles, including nitrogen heterocycles, suitable for use as functional groups include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyridine, pyrrole, and carbazole groups. Imidazole and pyridine groups are especially preferred.

Purines and pyrimidines suitable for use as functional groups include adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering,* pages 858–859, Kroschwitz, J. I., ed. John Wiley & Sons, 1990, and those disclosed by Englisch et al., *Angewandte Chemie, International Edition* 1991, 30, 613. The disclosures of each of the preceding publications are hereby incorporated by reference.

In the context of this specification, alkyl (generally $C_1$–$C_{20}$), alkenyl (generally $C_2$–$C_{20}$), and alkynyl (generally $C_2$–$C_{20}$) groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylbutyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups containing a pi bond, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

In the context of the invention, a straight chain compound means an open chain compound, such as an aliphatic compound, including alkyl, alkenyl, or alkynyl compounds; lower alkyl, alkenyl, or alkynyl as used herein include but are not limited to hydrocarbyl compounds having from about 1 to about 6 carbon atoms. The term branched compound, as used herein, denotes a straight chain compound, such as an alkyl, alkenyl, alkynyl compound, which has further straight or branched chains attached to one or more the carbon atoms of the straight chain. A cyclic compound, as used herein, refers to closed chain compounds, i.e. a ring of atoms, such as an alicyclic or aromatic compound. The straight, branched, or cyclic compounds may be internally interrupted, as in alkoxy or heterocyclic compounds.

Aryl groups preferably have 6 to 20 carbon atoms, and include but are not limited to substituted and unsubstituted aromatic hydrocarbyl groups. Aralkyl groups preferably have 7 to 20 carbon atoms, and include but are not limited to groups having both aryl and alkyl functionalities, such as benzyl and xylyl groups, which are attached through their alkyl portions. Preferred aryl and aralkyl groups include, but are not, limited to, phenyl, benzyl, xylyl, naphthyl, tolyl, pyrenyl, anthracyl, azulyl, phenethyl, cinnamyl, benzhydryl, and mesityl. These can be substituted or unsubstituted. It is preferred that if an aryl or alkyl group is substituted, the substitution be at a position on the aryl or aralkyl group such that the electronic effects of the substituent are isolated from the reactive functionality used to attach the aromatic moiety to the nitrogenous moiety or the tether. Accordingly, it is preferred that such substitutions be meta to the point of attachment of the aromatic moiety to the nitrogenous moiety or the tether.

The aliphatic and aromatic groups as noted above may be substituted or unsubstituted. In the context of this invention, substituted or unsubstituted, means that the compounds may optionally have any one of a variety of substituents, in replacement, for example, of one or more hydrogen atoms in the compound. Typical substituents for substitution of the aliphatic and aromatic groups of the invention include, but are not limited to, hydroxyl, alkoxy, alcohol, benzyl, phenyl, nitro, thiol, thioalkoxy, halogen, or alkyl, aryl, alkenyl, or alkynyl groups. Metal coordination groups according to the invention include, but are not limited to, carbonyl moieties, hyroxyl moieties, amine moieties, acid moieties and other more complex moieties such as hydroxamic acids, catecholamide, acetylacetone, 2,2'-bipyridine, 1,10-phenanthroline, diacetic acid, pyridine-2-carboxamide, isoalkyldiamine, thiocarbamate, oxalate, glycyl, histidyl and terpyridyl. Other metal coordination groups are also known (Mellor, D. P., *Chemistry of Chelation and Chelating Agents in International Encyclopedia of Pharmacology and Therapeutics,* Section 70, The Chelation of Heavy Metals, Levine, W.G. Ed., Pergamon Press, Elmford, N.Y., 1979). The disclosures of each of the preceding references are hereby incorporated by reference in their entirety.

Non-reactive functionalities used as chemical functional groups, such as groups that enhance pharmaco-dynamic properties, include groups that improve uptake and enhance resistance to enzymatic or chemical degradation. Non-reactive functionalities may also enhance pharmacokinetic properties. In the context of this invention, such groups improve uptake, distribution, metabolism or excretion. Non-reactive functionalities include, but are not limited to, alkyl chains, polyamines, ethylene glycols, steroids, polyamides, aminoalkyl chains, amphipathic moieties, and conjugate groups attached to any of the nitrogenous sites for attachment, as described above.

Conjugate groups of the invention include intercalators, reporter molecules, polyamines, polyamides, poly ethers including polyethylene glycols (PEGs), and other moieties known in the art for enhancing the pharmacodynamic properties or the pharmacokinetic properties. Typical conjugate groups include PEG groups, cholesterols, phospholipids, biotin, phenanthroline, phenazine, phenanthridine, anthraquinone, acridine, fluoresceins, rhodamines, coumarins, and dyes.

A number of chemical functional groups can be introduced into compounds of the invention in a blocked form and subsequently deblocked to form a final, desired compound. In general, a blocking group renders a chemical functionality of a molecule inert to specific reaction conditions and can later be removed from such functionality in a molecule without substantially damaging the remainder of the molecule (see, for example, Green and Wuts, Protective Groups in Organic Synthesis, 2d edition, John Wiley & Sons, New York, 1991). For example, amino groups can be blocked as phthalimido groups, as 9-fluorenylmethoxycarbonyl (PMOC) groups, and with triphenylmethylsulfenyl, t-BOC or benzyl groups. Carboxyl groups can be protected as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl)xanthine-9-yl (MOX). Chemical functional groups can also be "blocked" by including them in a precursor form. Thus, an azido group can be used considered as a "blocked" form of an amine since the azido group is easily converted to the amine.

Nitrogenous moieties can be incorporated into compounds of the invention in a blocked form to facilitate manipulation of chemical functional groups to particular sites within a given compound (see, for example, FIGS. 2–7). Blocking certain sites followed by reacting unblocked sites with a chemical functional group reactant and then selectively deblocking to give further unblocked sites is a useful method for deconvoluting a library. Preferred groups used for the blocking which can be selectively deblocked include T-BOC and o-nitrophenylsulfenyl. Another preferred blocking group that also includes the nitrogen is the phthalimido group which is deblocked to give a primary amine. These three protecting groups are especially useful in that each can be selectively removable without removing the others.

The compounds of the invention can be synthesized by a variety of chemistries. One preferred method of synthesizing the compounds of the invention is by solution phase synthesis. Another preferred method of synthesizing the compounds of the invention is by solid phase synthesis, using known methods and techniques.

Representative solid supports useful in the present invention include controlled pore glass (CPG), oxalyl-controlled pore glass (Alul et al., *Nucleic Acids Research* 1991, 19, 1527), TentaGel Support, which is an aminopolyethyleneglycol derivatized support (Wright et al., *Tetrahedron Letters* 1993, 34, 3373) or Poros which is a copolymer of polystyrene/divinylbenzene.

The chemical functional groups, i.e. groups that give individual characteristics to individual molecules, are attached to their respective monomeric units via the nitrogen atoms of the nitrogenous moieties. These chemical functional groups provide diverse properties or diversity to the resulting compounds. Such diversity properties include hydrogen-bond donors and acceptors, ionic moieties, polar moieties, hydrophobic moieties, aromatic centers, electron-donors and acceptors, pi bond stacking and metal binding. Together, the properties of the individual repeating units contribute to the uniqueness of the compounds in which they are found. Thus, a library of such compounds would have a myriad of properties, i.e. diversity. Collectively, the properties of the chemical functional groups on any individual compound contribute to the uniqueness of that compound and impart certain characteristics thereto for interaction with proteins, lipids, or nucleic acids, or for cellular or enzymatic interactions with a target molecule. The compounds of the invention may also possess herbicidal or insecticidal properties.

As noted above, the compounds of the invention can be prepared having each nitrogenous moiety functionalized with one or more chemical functional group in a predetermined configuration, or the nitrogenous moieties can be substituted with chemical functional groups via combinatorialization strategies. One useful combinatorial strategy is a "fix last" strategy noted in certain of the examples below. A further useful combinatorial strategy is the above-noted SURF™ strategy, which is disclosed and claimed in U.S. patent application Ser. No. 749,000, filed Aug. 23, 1991, and PCT Application US92/07121, filed Aug. 21, 1992, both of which are commonly assigned with this application. The entire disclosure of these applications are herein incorporated by reference.

Illustrative of the SURF™ strategy is a 2'-O-methyl oligonucleotide library (Ecker et. al., supra) shown in Table I below. Table I describes the selection of a 2'-O-methyl oligonucleotide for binding to an RNA hairpin. The $K_D$s, i.e.

the binding constants, were determined by gel shift. "X", is used to indicate the position being varied and underlining is used to indicate positions that become fixed during successive iterations of the SURFυ strategy.

TABLE I

| Subsets | K$_D$ (mM) | | | |
|---|---|---|---|---|
| | X = A | X = C | X = G | X = T |
| Round 1 | | | | |
| NNNNXNNNN | 22 | <u>10</u> | >100 | >100 |
| Round 2 | | | | |
| NNN<u>NC</u>XNN | >10 | <u>4</u> | >10 | >10 |
| Round 3 | | | | |
| NNXN<u>C</u>N<u>C</u>NN | >10 | <u>0.5</u> | >10 | >10 |
| Round 4 | | | | |
| NN<u>C</u>X<u>C</u>N<u>C</u>NN | >10 | <u>0.15</u> | >10 | >10 |
| Round 5 | | | | |
| NN<u>CCC</u>X<u>C</u>NN | <u>0.08</u> | >1 | 0.4 | >1 |
| Round 6 | | | | |
| NN<u>CCCAC</u>XN | <u>0.05</u> | >0.5 | 0.08 | >0.5 |
| Round 7 | | | | |
| NX<u>CCCACA</u>N | >0.1 | >0.1 | <u>0.03</u> | >0.1 |
| Round 8 | | | | |
| N<u>GCCCACA</u>X | 0.05 | <u>0.02</u> | 0.05 | 0.04 |
| Round 9 | | | | |
| X<u>GCCCACAC</u> | 0.03 | 0.05 | 0.02 | <u>0.01</u> |

This SURF™ strategy has not been previously used for libraries, except those that employ naturally-occurring nucleotide monomer units, in phosphodiesters or phosphorothioates. Other combinatorial strategies have been previously used only for libraries that employ amino acids as monomeric units.

One advantage of the present invention is that the simple design of compounds of the invention, having multiple sites for diversity, enables the combining of rational drug design with methodologies used for the screening of thousands of compounds. This is achieved by using the compounds of the invention in combinatorial techniques such as the SURF™ strategy or the "fix last" strategy described herein.

The compounds of the invention can be used in diagnostics, therapeutics and as research reagents and kits. They can be used in pharmaceutical compositions by including a suitable pharmaceutically acceptable diluent or carrier. In preferred embodiments, the compounds of the invention act as inhibitors of enzymes such as phospholipase $A_2$; as inhibitors of pathogens such as viruses, mycobacterium, bacteria (gram negative and gram positive), protozoa and parasites; as inhibitors of ligand-receptor interactions such as PDGF (platelet derived growth factor), $LTB_4$ (leukotriene $B_4$), IL-6 and complement $C5_A$; as inhibitors of protein/protein interactions including transcription factors such as p50 (NFκB protein) and fos/jun; for the inhibition of cell-based interactions including ICAM induction (using inducers such as IL1-β, TNF and LPS) and as herbicides and insecticides. In other preferred embodiments, the compounds of the invention are used as diagnostic reagents for each of the above noted biological entities, and as reagents in assays and as probes. In other preferred embodiments, the compounds of the invention are used to chelate heavy metals and as imaging agents.

The compounds of the invention generally are prepared by coupling preselected bifunctional synthons under conditions effective to form the compounds. In certain embodiments, compounds of the invention are prepared by intermolecular reductive coupling. In other embodiments, compounds of the invention can be prepared by intermolecular radical addition reactions. In further embodiments, compounds can be prepared by nucleophilic displacement. In each of these embodiments, nitrogen atoms in the resulting substituents can be further functionalized. For example, the nitrogen atoms of the nitrogenous moieties can be reacted with a group having structure $R_L$—T—L, thereby displacing the $R_L$ leaving group and forming a covalent —N—T—L linkage where T—L represents a chemical functional group (wherein T is a single bond or part of the functional group) or a tethered chemical functional group.

Desired amino compounds, if not directly available, can be synthesized by treating the corresponding hydroxyl-terminated compound with $Ph_3P$, $CBr_4$ and $LiN_3$ according to the procedure of Hata et al. (*J. Chem. Soc. Perkin* 1 1980, 306) to furnish a terminal azide. Reduction of the azido group with tributyltin hydride provides the desired amino functionality.

Hydroxylamino nitrogenous groups can be prepared by treating the corresponding hydroxyl compound with N-hydroxyphthalimide, triphenylphosphine and diethylazodicarboxylate under Mitsunobu conditions to provide an O-phthalimido derivative. The free hydroxylamino compound can be generated in quantitative yield by hydrazinolysis of the O-phthalimido derivative.

Hydrazino compounds can be prepared by treating hydroxyl-terminated compounds with tosyl chloride in pyridine to give an O-tosylate derivative. Treatment of benzylcabazide with O-tosylate will furnish a benzylcarbazide derivative, which on hydrogenation provides the free hydrazino moiety for reductive coupling.

The hydrazino compound (hydrazine) synthesized as described above can be further converted to a hydrazide by reacting it with a carboxylic ester, or an acid halide in the presence of a base such as pyridine or DIEA.

Amino compounds (amines) may be further functionalized to form amides, hydrazides, carbamates, ureas, sulfonamides, sulfinamides and sulfanamides. An amide compound can be prepared by treating the amine with an acid halide, such as an acid chloride, in the presence of a base such as pyridine. Alternatively, amides can also be prepared by the action of an amine on a carboxylic ester.

Carbamates can also be synthesized from amines. The procedure involves reaction of the amine with an alkyl halide and potassium carbonate in the presence of a phase transfer catalyst such as $Bu_4NH^+$ $HSO_4^-$. Carbamates can also be obtained by the treatment of an amine with an appropriate alkyl or aryl chloroformate, or by reacting an amine with carbon monoxide, oxygen and an alcohol, in the presence of a catalyst such as pyridine.

Further, amines can be converted to ureas by reacting the amine with carbon monoxide in the presence of selenium or sulfur, or $Pd(OAc)_2$—$I_2$—$K_2CO_3$ (only for secondary amines). Also, amines can be added to isocyanates to form ureas. Symmetrically substituted ureas can be obtained by the reaction of an amine with phosgene or ethyl carbonate.

Sulfonamides can be prepared from amines by the reaction of an amine with a sulfonyl chloride in the presence of a base. Sulfinamides can be prepared by the reaction of an amine with a sulfinyl chloride in the presence of a base. The sulfonamide or sulfinamide thus formed can further be reduced to a sulfanamide by $LiAlH_4$, zinc and acetic acid or triphenylphosphine and iodine.

The nitrogen atoms of nitrogenous compounds such as amines, hydroxylamines, hydrazines, amides, carbamates, ureas, sulfonamides, sulfinamides and sulfanamides can be alkylated by treating the nitrogenous compound with a base such as sodium hydroxide or sodium hydride, and then reacting the resulting sodium salt with a halide such as the illustrative halides (benzyl bromide, 3-methylbenzyl bromide, 3-methoxybenzyl bromide or 3-nitrobenzyl bromide) used in the examples below. A wide spectrum of halides can be used for this purpose.

The above-mentioned nitrogenous compounds can also be acylated at the nitrogen atom by treating them with a base such as sodium hydroxide or sodium hydride, and then reacting the resultant sodium salt of the nitrogenous compound with an acid halide. Illustrative acid halides include, but are not limited to, benzoyl chloride, 3-methylbenzoyl chloride, 3-methoxybenzoyl chloride or 3-nitrobenzoyl chloride.

Additionally, the nitrogenous compounds can be functionalized at the nitrogen atom by reaction of the nitrogenous compound with an aldehyde or ketone forming a Schiff base. The Schiff base is then reduced in the presence of a reducing agent such as $NaCNBH_3$, sodium metal in ethanol, or organometallic compounds such as allylic boranes and allylic stannanes.

Figure 2:
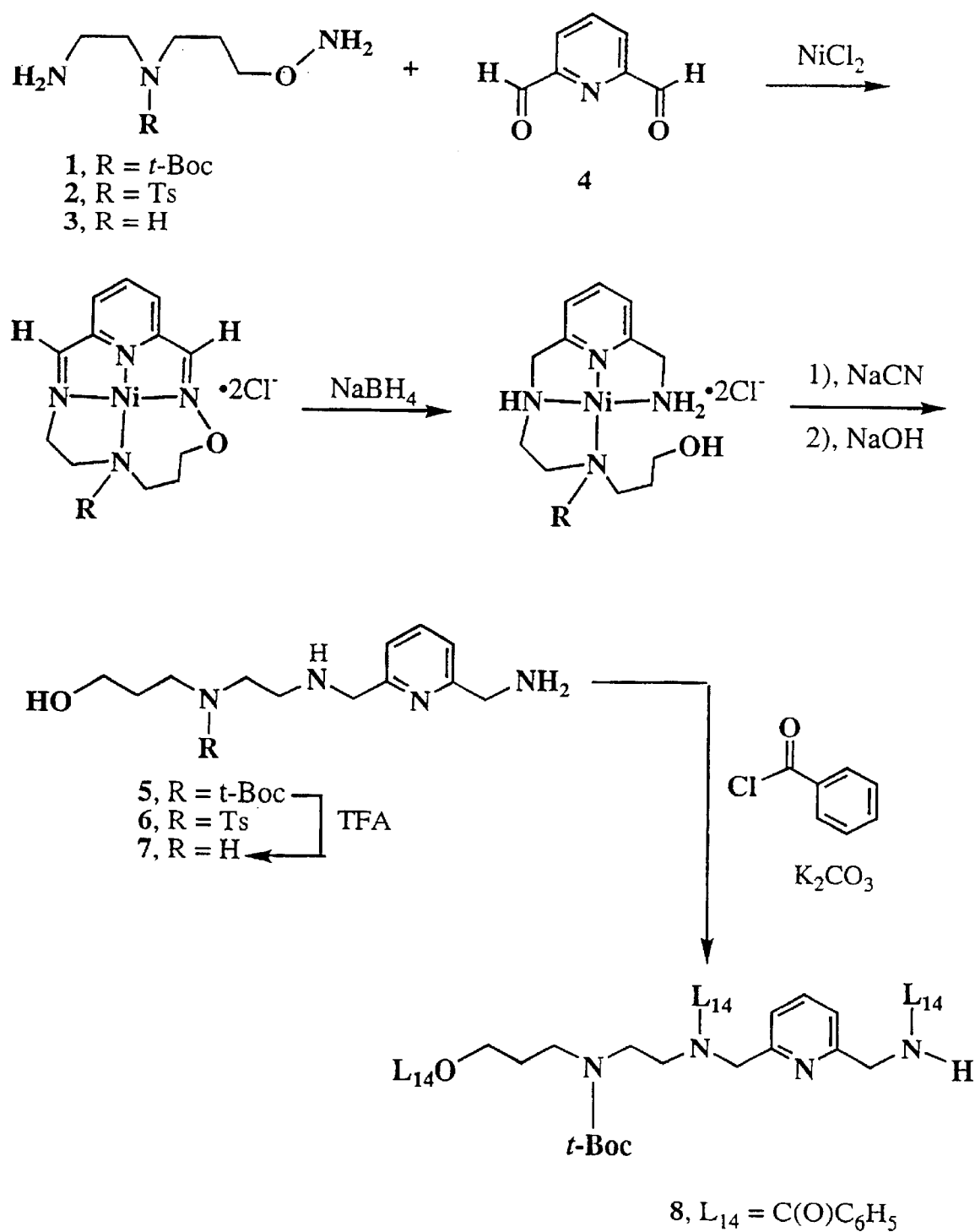
FIGS. 2 and 3 show the synthesis of a di-substituted pyridine compound wherein the substituents are attached by the reaction of 2,6-bis-formalpyridine with a single aminooxy containing compound.
Figure 3:
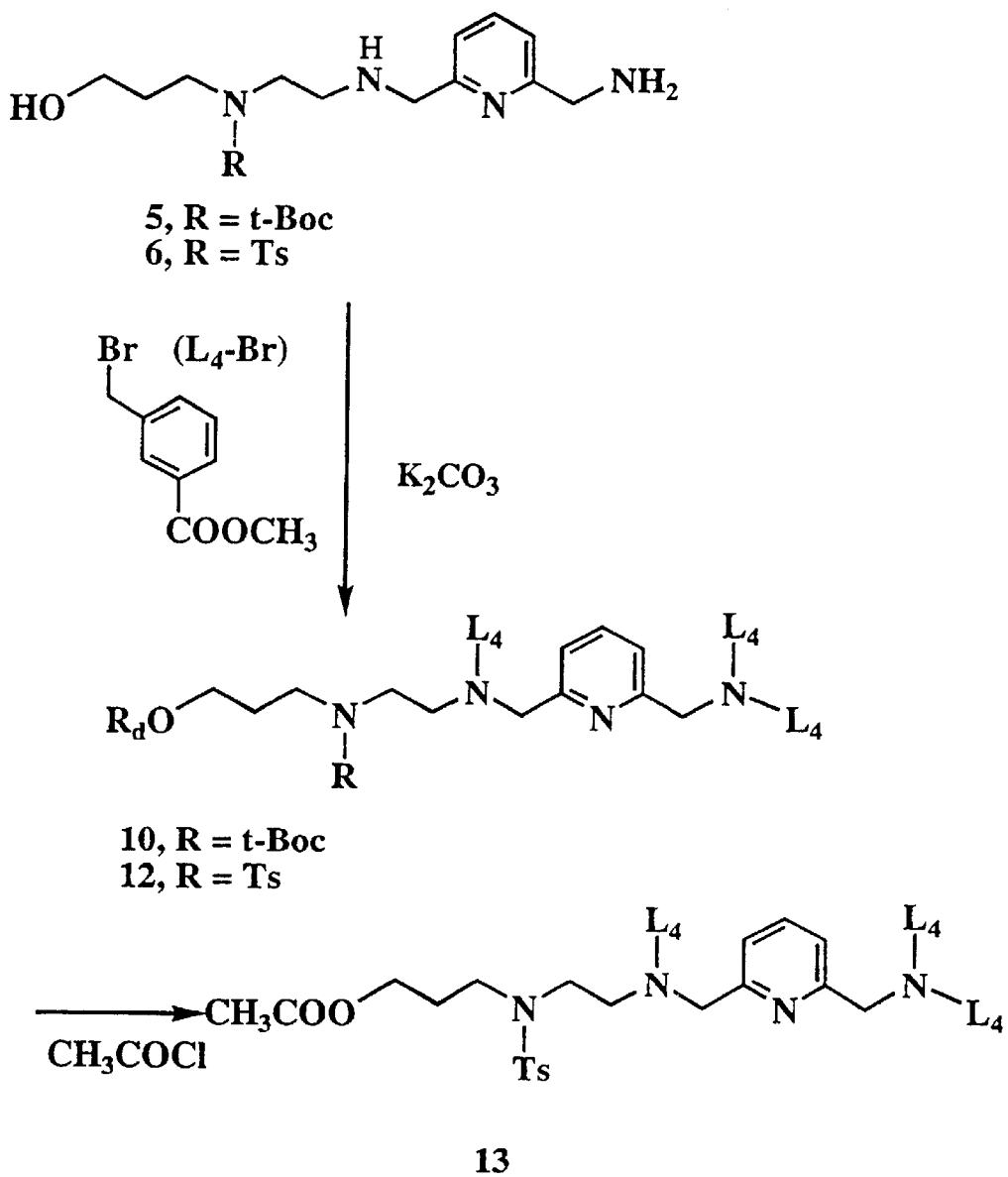
Figure 4:
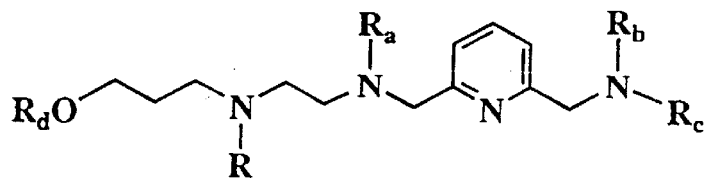
FIG. 4 shows libraries of compounds synthesized according to the procedures shown in FIGS. 2 and 3.

In one aspect of the invention, compounds and libraries are synthesized as shown in FIGS. 2 and 3, using letters shown in FIG. 1. FIGS. 3 and 4 show the synthesis of a di-substituted pyridine compound wherein the substituents are attached by the reaction of 2,6-bis-formalpyridine with a single aminooxy containing compound. The aminooxy bond is cleaved to form the di-substituted pyridine having 3 nitrogenous moieties, 2 of which are secondary and one which is primary. These nitrogenous moieties contain 4 nitrogenous sites that can be substituted with chemical functional groups. As illustrated in FIG. 3, three of the nitrogenous sites are substituted in a single reaction, leaving a fourth site protected. The blocked nitrogenous site can be deblocked and treated with a further chemical functional group to give the final library.

Figure 8:
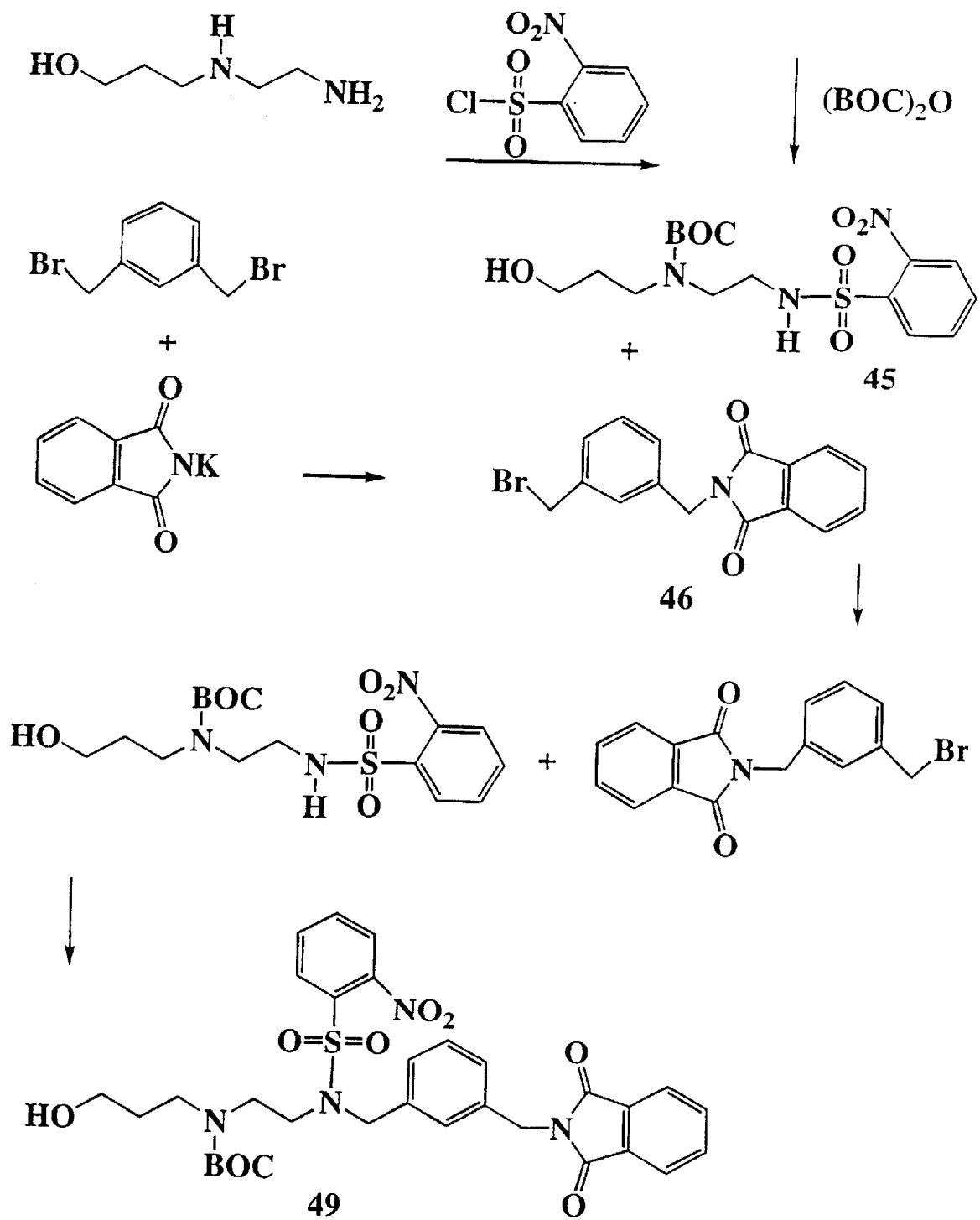
FIGS. 8 and 9 show the synthesis of a di-substituted benzene compound wherein the substituents are attached to the benzene one at a time in separate reactions.
Figure 9:
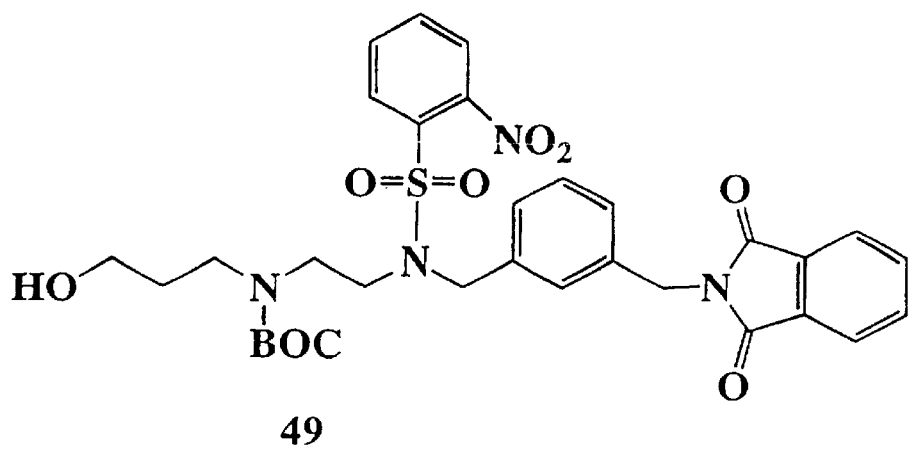
Figure 9:
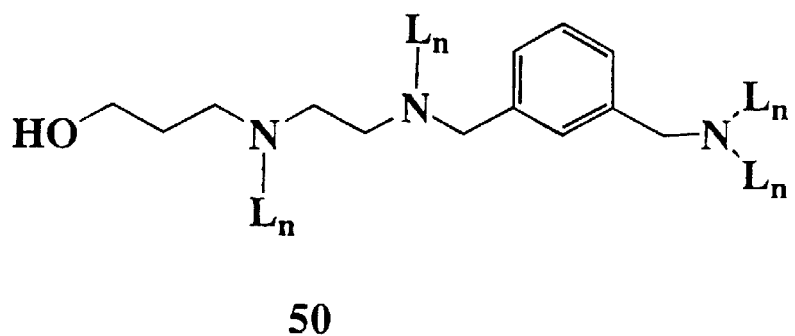

In another aspect of the invention, compounds and libraries are synthesized according to FIGS. 8 and 9, which show the synthesis of a di-substituted benzene compound wherein the substituents are attached to the benzene one at a time in separate reactions. One advantage to this synthetic procedure is the inclusion of protecting groups on the substituent groups. The use of protecting groups enables the complete deconvolution of each compound of the invention. As illustrated in FIG. 8 and Examples 79–86, the phthalimido, t-butyloxycarbony, and o-nitrophenylsulfonyl protecting groups are used to synthesize an intermediate compound (49, FIG. 8) that is used to prepare either a library or a single compound.

The overall extent of diversification will be a factor of both the number of sites and the number of reactant species presented to each site for covalent bonding to the site. To achieve a library having limited diversification, only a few sites or chemical functional groups need be used as illustrated in Examples 23–26. To achieve a high degree of diversification, the number of sites, the number of chemical functional groups, or both is expanded. The complexity of the library is represented by the number of chemical functional groups taken to the power represented by the number of sites at which these chemical functional groups can be located. Thus for example, 5 chemical functional groups at three unique sites will give a library of 125 ($5^3$) compounds, 20 chemical functional groups at 4 sites will give a library of 160,000 ($20^4$) compounds, and 8 chemical functional groups at 6 sites will give a library of 262,144 ($8^6$) compounds. Normally, to obtain a large library of linear oligomeric compounds such as peptides, the length of the peptide, as for instance a 10-mer, is the determinant. A peptide of this length synthesized combinatorially using all 20 or so naturally occurring amino acids offers a large number of sites. Thus, the resulting library will be very complex, having about $10^{13}$ different compounds.

In constructing and assaying compounds of the invention, if an enzyme binder or other like biological property is desired, normally a compound having a smaller number of nitrogenous sites would be selected such that the spatial size (the three dimensional global footprint) of the macromolecule does not exceed a pre-selected size in order to fit into the enzyme pocket or other biological target. If uptake of a molecule is a consideration and it is determined that the molecular weight of the molecule should not exceed a pre-selected molecular weight range, as for instance a molecular weight of 500, 1000 or 1500, then a small number of sites might also be selected. In these instances, the number of sites that can be combinatorialized is maintained relatively small (typically less than 10, preferably less than 6 and more preferred from 3 to 4). In order to construct very complex (large) libraries, a greater number of chemical functional groups are used to expand the libraries such that they contain a large number of individual species. As opposed to peptides, where normally only 20 amino acids are available for selection as the chemical functional groups, in diversifying the compounds of the invention one is not constrained as far as chemical functional groups are concerned, and any number of chemical functional groups can be selected.

For targets where size of the macromolecule is not an overriding consideration, such as in a metal ion scavenger to be used in an industrial waste stream, macromolecules having a large number of sites can be selected and the number of chemical functional groups decreased. Thus, only those chemical functional groups that are known to be metal coordinating groups might be selected. In these instances, the number of nitrogenous sites included in the molecule would be selected in the high range, such as, for example, from 4 to 9, preferably 6 to 9.

The chemical functional groups can be selected on the basis of chain length (i.e. short versus long), the use of a ring versus a linear group, the use of an aromatic versus aliphatic group, the use of a functionalized group versus a non-functionalized group, or any of the wide variety of chemical functional groups available. Indeed, simply varying functional moieties, e.g. acid, alcohol, aldehyde, amide, amine, amidine, azo, azoxy, double bond, ether, ethylene oxide, guanidine, halide, haloalkyl, hydrazine, hydroxylamine, ketone, mercaptan, nitrate, nitrile, nitro, nitroso, quaternary nitrogen, sulfide, sulfone, sulfoxide, triple bond, urea, etc. on a single backbone, e.g. a simple alkyl group, yields a vast array of diversity functions. When this is expanded to include placement of such varied functional moieties on a broad platform of backbones, e.g. a series of alkyl compounds, a series of aryl compounds, a series of alicyclic compounds, etc., the potential for a vast array of chemical functional groups is apparent. Other chemical functional groups include alkyl, alkenyl, alkynyl, alicyclic and substituted alkyl, alkenyl, alkynyl, alicyclic; aryl and substituted aryl; aralkyl, substituted aralkyl, heterocycles, moieties as found in the a-position of amino acids, nucleobases such as pyrimidines and purines; and metal chelating groups.

Chemical functional groups of the invention can be represented by the formula:

—T—L wherein:
each T is, independently, a single bond, a methylene group or a group having the formula:

—{[CR$^1$R$^2$]$_m$—(R$^5$)—[CR$^1$R$^2$]$_n$—[C(R$^6$)]$_p$—(E)—}$_q$— each R$^1$, R$^2$ and R$^3$ is, independently, H, alkyl or haloalkyl having 1 to about 10 carbon atoms, alkenyl having 2 to about 10 carbon atoms, alkynyl having 2 to about carbon atoms, or aryl having 6 to about 14 carbon atoms;
each R$^5$ and E is, independently, a single bond; CH=CH; C≡C; O; S; NR$_3$; SO$_2$; C$_6$–C$_{14}$ aryl; substituted C$_6$–C$_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from hydroxyl (OH), alkoxy, alcohol, benzyl, phenyl, nitro (NO$_2$), thiol (SH), thioalkoxy, halogen, alkyl, aryl, alkenyl, and alkynyl groups;
each R$^1$ is =O, =S, =NR$_3$;
each m and n is, independently, zero to 5;
each p is, independently, zero or 1;
q is 1 to about 10; and
each L is, independently, H, C$_1$–C$_{10}$ alkyl; substituted alkyl; C$_2$–C$_1$ alkenyl; substituted alkenyl; C$_2$–C$_{10}$ alkynyl; substituted alkynyl; C$_4$–C$_7$ carbocyclic alkyl; substituted carbocyclic alkyl; alkenyl carbocyclic; substituted alkenyl carbocyclic; alkynyl carbocyclic; substituted alkynyl carbocyclic; C$_6$–C$_{14}$ aryl; substituted C$_6$–C$_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from alkyl, alkenyl, alkynyl, aryl, hydroxyl, alkoxy, alcohol, benzyl, nitro, thiol, thioalkyl, thioalkoxy, trifluoromethyl or halogen groups; or L is phthalimido, an ether having 2 to 10 carbon atoms and 1 to 4 oxygen or sulfur atoms, a metal coordination group, a conjugate group, halogen, hydroxyl, thiol, keto, carboxyl, NR$^1$R$^2$, CONR$^1$, amidine (C(=NH)NR$^2$R$^3$), guanidine (NHC(=NH) NR$^2$R$^3$), glutamyl (R$^1$OOCCH(NR$^2$R$^3$)(CH$_2$)$_2$C(=O), nitrate, nitro, nitrile, trifluoromethyl, trifluoromethoxy, NH-alkyl, N-dialkyl, O-aralkyl, S-aralkyl, NH-aralkyl, azido (N$_3$), hydrazino (NHNH$_2$), hydroxylamino (ONH$_2$), sulfoxide (SO), sulfone (SO$_2$), sulfide (S—), disulfide (S—S), silyl, a nucleosidic base, an amino acid side chain, a carbohydrate, a drug, or a group capable of hydrogen bonding.

To covalently bind chemical functional groups to nitrogen atoms of nitrogenous moieties, various chemical functional group reactant compounds are used. These are the reactive forms of the chemical functional groups; i.e., they have a further functional group thereon which is capable of effecting or facilitating the covalent bond to the nitrogen atom of the nitrogenous moiety. Examples of these further functional groups include the variety of functionalities known to interact with amine nitrogens, such as, for example, OHC-(aldehydes), R$_1$C(O)—(ketones) halogens, HO$_2$C-(carboxyl groups), and halogen-CO— (acid halides).

Figure 6:
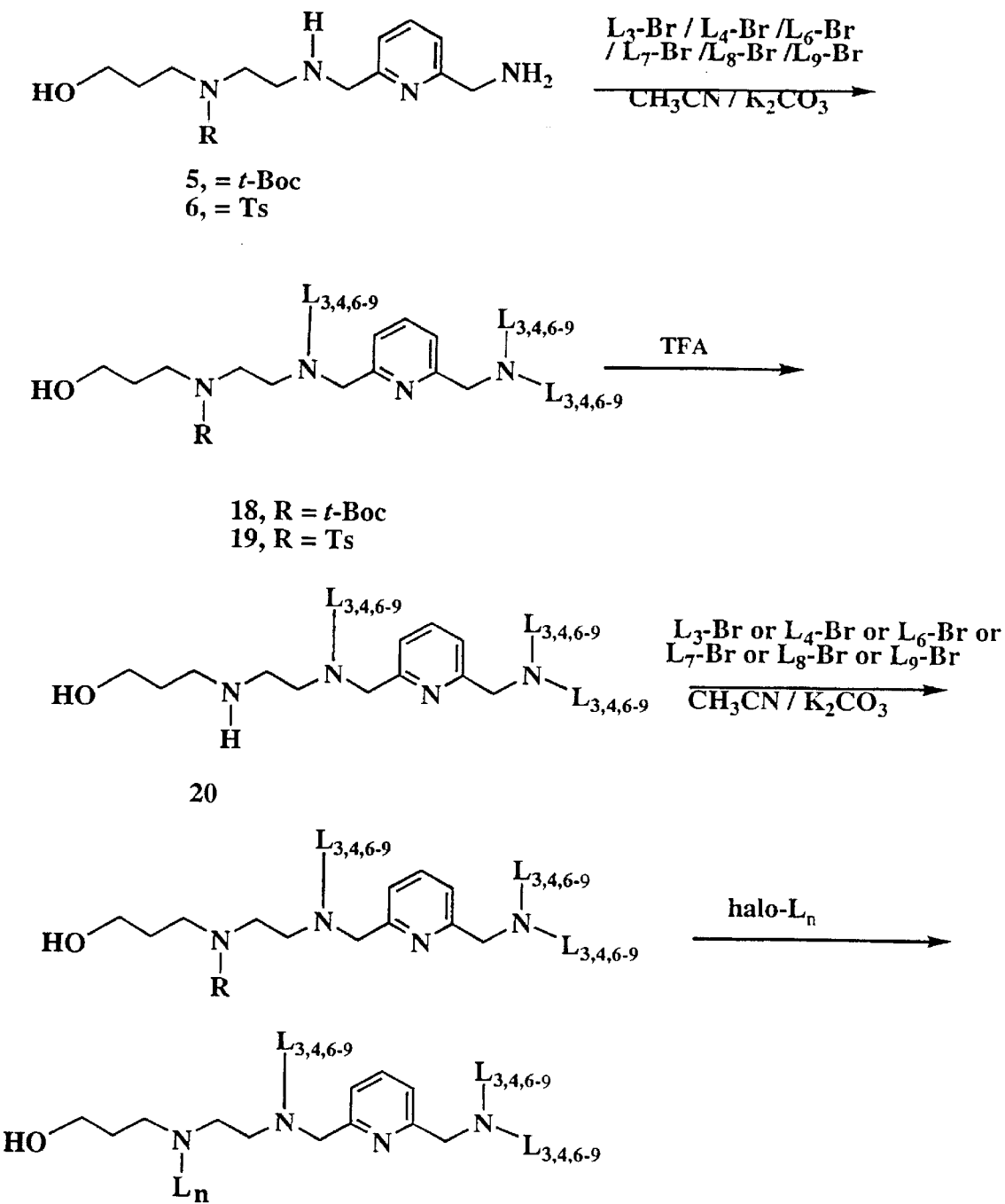
FIGS. 6 and 7 show the combinatorialization of a macromolecule having three nitrogenous sites coupled with four chemical functional groups to achieve an overall complexity of 625 ($5^4$) compounds, using a "fix last" deconvolution strategy.
Figure 7:
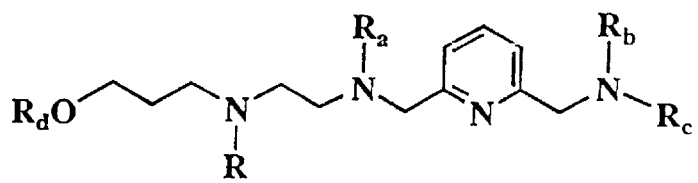

The "diversity end" of chemical functional group reactant compounds have other functionalities, as described above. FIGS. 6 and 7 show the combinatorialization of a macromolecule having three nitrogenous sites coupled with four chemical functional groups to achieve an overall complexity of 625 (54) compounds. A "fix last" deconvolution strategy is utilized.

In addition to the preceding process for the deconvolution of combinatorial libraries, which includes the iterative processes of splitting and fixing one position, there are many other strategies used by those skilled in the art. One such strategy utilizes a subtractive technique where selected letters are removed from selected pools and the active pools are pursued to elicit the most active compound (see e.g., Carell, T., supra). Other methods known in the art include labeling (including chemically or radioisotopically), enzyme binding assays, and selection assays. Another method, mentioned previously, is fixing one letter at a time. A further method discussed above involves the use of protecting groups to make selected sites unavailable for functionalization until other sites are functionalized. Many of these methods can be combined to customize conditions to meet synthetic needs.

In some preferred embodiments, libraries containing compounds of the invention are generated by selecting a substituted cyclic compound and a plurality of chemical functional group reactants as discussed above, and reacting the chemical functional group reactants with the substituted cyclic compounds to form covalent bonds between said T groups of said chemical functional group reactants, and unprotected nitrogen groups on the substituted cyclic compound. Preferably, a further nitrogen is selectively deprotected, and with a further chemical functional group reactant, resulting in the covalent binding of —T—L to the nitrogen. The chemical functional group reactants are preferably reacted with each nitrogen essentially iteratively. More preferably, each of nitrogens are reacted with the chemical functional group reactants iteratively, and in each of the iterative reactions, the chemical functional group reactants are reacted with the nitrogen essentially simultaneously.

Combinatorial libraries in accordance with the present invention have been tested for antibacterial and antifungal activity utilizing assays that determine the minimum inhibitory concentration (MIC). The antibacterial assays utilize staphylococcus aureus, *Streptococcus pyogenes,* and *Escherichia coli* imp– and the antifungal assay utilizes candida albicans. Activity has been detected in a number of libraries of the present invention. A number of libraires have been further deconvoluted to subset libraries. Many of these subset libraries also have antibacterial and/or antifungal activity.

The following data are for first round libraries or parent libraries that were assayed for activity in accordance with the methods illustrated in Procedures 1–4.

| MIC ASSAYS | | | | |
|---|---|---|---|---|
| Library | S. aureus | S. pyrogenes | E. coli | C. albicans |
| 20 (Ex. 29) | 1–5 | 1–5 | 1–5 | 5–25 |
| 21 (Ex. 31) | 1–5 | 1–5 | 1–5 | 5–25 |
| 28 (Ex. 36) | | 5–12 | 5–25 | 25–50 |
| 29 (Ex. 37) | | 12–25 | 5–25 | |
| 30 (Ex. 38) | | 5–12 | 5–25 | 25–50 |
| 9 (Ex. 59) | | 5–25 | 5–25 | 1–5 |
| 57 (Ex. 133) | | 42 | | |
| 58 (Ex. 133) | | 42 | 20 | |

Libraries 20, 21, 28, 29, and 30 (see FIG. 7) have been deconvoluted to give numerous Libraries having activity in the MIC assays for *E. coli* imp– and *S. pyrogenes*.

Selected libraries have been assayed for activity against $PLA_2$. Procedure 8 illustrates the materials and methods utilized in this assay. Two of the selected libraries showed activity in the assay.

| PLA₂ ASSAY | |
|---|---|
| Library | inhibition at 100 μM |
| 18 (Ex. 27) | 23% |
| 20 (Ex. 29) | 68% |

Selected Libraries have also been assayed for their ability to inhibit tat/TAR RNA/protein interactions. Assays were performed in accordance with Procedure 5. Libraries are examined at a concentration of 100 μM.

| tat/TAR Assay | |
|---|---|
| Compound | Inhibition |
| 20 (Ex. 29) | 31% |
| 23 (Ex. 32) | 10% |
| 24 (Ex. 33) | 12% |

| Library | Inhibition |
|---|---|
| 58 | (38%) 100 μM |

In the illustrative examples below, the basic chemistry employs various types of nitrogenous moieties, e.g. primary amine, secondary oxyamine, secondary amine, each of which is protected with a suitable protecting group when necessary. For illustrative purposes, the protective groups selected for protecting these nitrogen atoms are azido (a precursor-type protecting group which gives an amino group), tert-butoxycarbonyl, sulfenyltriphenyl, o-nitrophenylsulfenyl, and phthaloyl. The tert-butoxycarbonyl (t-Boc) and the sulfenyltriphenyl [S(Ph)₃] moieties can be removed under differential acid conditions, and the phthaloyl moiety can typically be removed with hydrazine (basic conditions), or under certain acid conditions.

EXAMPLE 1

N-Benzyl-3-amino-1-propanol

To a solution of benzaldehyde (10 g, 94.23 mmol) and trimethylorthoformate (15.5 mL, 141 mmol) in MeOH (300 mL) was added dropwise 3-amino-1-propanol (7.21 mL, 94.23 mmol) at room temperature. The reaction was allowed to stir at room temperature for 5 hours followed by cooling to 0° C. in an ice bath. Sodium borohydride (3.56 g, 94.23 mmol) was added in two portions and when the bubbling stopped the solvent was evaporated. The resulting residue was partitioned between ethyl acetate (75 mL) and water (75 mL). The aqueous layer was extracted twice with ethyl acetate (75 mL). The ethyl acetate extracts were collected and washed twice with Brine (50 mL), dried over $MgSO_4$, filtered, and concentrated. Drying afforded 14.42 g (93%) of the compound which was used in the next step of synthesis without further purification.

EXAMPLE 2

N-Phthalimidoethyl(benzyl)-3-amino-1-propanal

N-Benzyl-3-amino-1-propanol (6 g, 36.76 mmol) was dissolved in DMF (300 mL). To this solution was added $K_2CO_3$ (1.52 g, 11.03 mmol) and KI (915 mg, 0.551 mmol) and the reaction mixture was heated to 65° C. for 10 hours. The reaction had gone to completion as indicated by TLC using ethyl acetate:dichloromethane (2:3, v/v). The solvent volume was reduced by evaporation under vacuo and the resulting residue was partitioned between ethyl acetate (100 mL) and water (100 mL). The water layer was extracted 3× with 50 mL of ethyl acetate. The ethyl acetate layers were combined and washed twice with brine (50 mL), dried over $MgSo_4$, filtered and concentrated. The title compound was purified by silica gel flash column chromatography using ethyl acetate:Hexanes (2:5, v/v) as the eluent. The appropriate fractions were collected and concentrated to afford 7.0 g (56%) of the title compound as a clear oil.

$^1$H NMR ($CDCl_3$) δ1.64–1.78 (m, 2H), 2.66–2.80 (m, 4H), 3.58–3.68 (m, 4H), 3.80 (t, 2H), 7.09–7.20 (m, 5H), 7.69–7.88 (m, 4H). HRMS (FAB) m/z 339.169 (M+$C_s$)+ ([$C_{20}H_{22}N_2O_3+C_s$] requires 339.170).

EXAMPLE 3

N-Phthalimidoethyl-3-amino-1-propanol (acetate salt)

N-Phthalimidoethyl(benzyl)-3-amino-1-propanol (4.62 g, 11.95 mmol), Pd/C 10% (1 g) and MeOH:acetic acid (95:5, v/v) (100 mL) was transferred to a 250 mL par hydrogenation flask. The flask was purged and filled with $H_2$ three times and then left under $H_2$ at 55 psi with shaking. The mixture absorbed 20 psi of $H_2$ in 30 minutes. The shaking was stopped and the pressure was raised to 55 psi again. After 3 hrs the pressure was 45 psi so the pressure was increased to 55 psi once more. The reaction was complete as indicated by TLC dichloromethane:MeOH (9:1, v/v) in 4 hours. The reaction mixture was filtered though a bed of celite and the solvent evaporated under vacuo to leave a yellowish oil. The oil was purified by silica gel flash column chromatography using dichloromethane:MeOH (9:1, v/v) as the eluent. The appropriate fractions were combined and concentrated under vacuo to afford 2.51 g (68%) of the title compound as a white solid (m.p. 94–95° C.).

$^1$H NMR ($CDCl_3$) δ1.49–1.64 (m, 2H), 1.83 (s, 3H), 2.66 (t, 2H, J=7.0 Hz), 2.84 (t, 2H, J=6.3 Hz), 3.44 (t, 2H, J=6.3 Hz), 6.20 (bs, 2H, disappeared in $D_2O$), 7.80–7.92 (m, 4H. $^{13}$C NMR ($CDCl_3$) δ21.87, 31.87, 36.77, 45.76, 46.56, 59.6, 1.96, 131.84, 134.28, 168.02, 172.84,. HRMS (FAB) m/z 249.124 (m)⁺($C_{13}H_{17}N_2O_3$, requires 249.123).

EXAMPLE 4

N-[Phthalimidoethyl-(t-Boc)]-3-amino-1-propanol

N-Phthalimidoethyl-3-amino-1-propanol (2.51 g, 8.14 mmol) and triethylamine were added to dichloromethane (40 mL). Di-tert-butyl-dicarbonate (3.55 g, 16.28 mmol) was added in one portion. The reaction went to completion in 4 hours as indicated by TLC using ethyl acetate:hexanes (1:1, v/v). The reaction mixture was washed 3× with water and once with brine, dried over $MgSO_4$, filtered, and concentrated. The residue was purified by silica gel flash column chromatography using hexanes:ethyl acetate (8:2 to 1:1, v/v). The appropriate fractions were combined and evaporated to afford 2.31 g (81%) of the title compound as a colorless oil.

$^1$H NMR (CDCl$_3$) δ1.29 (s, 9H), 1.58–1.80 (M, 2 h), 3.27–3.61 (M, 6 h), 3.65 (BS, 1 h, disappears in D$_2$O), 3.84 (t, 2H, J=6.3 Hz), 7.65–7.79 (m, 2H), 7.80–7.91 (m, 2H). $^{13}$C NMR (CKCl$_3$) δ27.88, 30.4, 35.61, 4.4, 58.1, 80.40, 13.17, 31.89, 133.98, 156.50, 167.92. HRMS (FAB) m/z 371.157 (m+Na)$^+$ ([C$_{18}$H$_{24}$N$_2$O$_5$+Na] requires 371.158).

EXAMPLE 5

N-[Phthalimidoethyl(t-Boc)]-3-amino-1(O-phthalimido)-propanol

N-[Phthalimidoethyl(t-Boc)]-3-amino-1-propanol (1.16 g, 3.33 mmol), triphenylphosphine (959 mg, 3.66 mmol) and N-hydroxyphthalimide (597 mg, 3.66 mmol) were dissolved in distilled THF (30 mL). The solution was cooled to 0° C. in an ice bath and diethylazodicarboxylate (DEAD, 0.629 mL, 4.00 mmol) was added dropwise. Five drops of DEAD were added and the next five were added after the orange color had dissipated, this procedure was repeated until all the DEAD was added over a period of about 2 hours. The reaction mixture was allowed to warm up to room temperature overnight. The end point of the reaction was detected by TLC using ethyl acetate: hexanes (1:1, v/v). The solvent was removed under vacuo and dry diethyl ether (100 mL) was added. The title compound precipitated out of the solution to afford 1.23 g (75%) as a white solid after drying (m.p. 171–173° C.).

$^1$H NMR (CDCl$_3$) δ1.20 (s, 9H), 1.90–2.10 (m, 2H), 3.40–3.54 (m, 2H), 3.55–3.66 (m, 2H), 3.89 (t, 2H), 4.22 (t, 2H), 7.63–7.89 (m, 4H). HRMS (FAB) m/z 626.089 (M+Cs)$^+$ ([C$_{26}$H$_{27}$N$_3$O$_7$+Cs] requires 626.090).

EXAMPLE 6

N1[(t-Boc)-3-(O-amino)propanol-1-yl] diaminoethane 1 (FIG. 2)

N-[Phthalimidoethyl(t-Boc)]-3-amino-1-(O-phthalimido)-propanol (10.35 g, 20.97 mmol) was suspended in Ethanol (absolute, 300 mL). To this solution was added hydrazine (5 eq. 105 mmol, 3.3 mL) in one portion. The reaction mixture was stirred for 6 hours at which time the resulting white precipitate was filtered off. The filtrate was concentrated under vacuo to a white solid with a yellowish green oil. To the residue was added ethyl ether (150 ml), the white solid was filtered, and the filtrate was concentrated to a white solid with a yellowish green oil. The target compound was purified from this mixture by silica gel flash column chromatography using dichloromethane: MeOH (9:1, v/v) followed by dichloromethane:NH$_4$OH:MeOH (85:10:5, v/v) as the eluents. The desired fractions were combined, concentrated, and dried to afford 3.1 g (63%) of the title compound as a colorless oil.

$^1$H NMR (CDCl$_3$) δ1.39 (s, 9H), 1.64–1.75 (m, 2H), 2.76 (t, 2H, J=6.4 Hz), 3.10–3.32 (m, 4H), 3.61 (t, 2H, J=6.3 Hz), 4.39 (bs, 4H, disappears in D$_2$O). $^{13}$C NMR (CDCl$_3$) δ28.48, 40.72, 45.54, 49.86, 73.79, 79.70, 156.38. HRMS (FAB) m/z 234.182 (m+H)$^+$ ([C$_{10}$H$_{23}$N$_3$O$_3$+H] requires 234.182).

EXAMPLE 7

2-Aminamethylene-6-{[N1-(methyl-1yl)-N2-(t-Boc) 1-propanol-3-yl]-1,2-diaminoethane}pyridine 5 (FIG. 2)

A solution of N1[(t-Boc)-3-(O-amino)propanol-1-yl] diaminoethane (1, FIG. 2, 2.50 g, 10.7 mmol) in ethanol (15 ml) was added to a stirred solution of nickel(II) chloride hexahydrate (2.55 g, 10.7 mmol) in ethanol-water (1:1, 60 ml). Pyridine-2,6-dicarboxaldehyde (4, FIG. 2, Aldrich, 1.45 g, 10.7 mmol) was added to the above blue solution followed by glacial acetic acid (1.0 mL). The resulting deep blue solution was stirred at room temperature for 2 hours and then at 80° C. for 6 hours. The solution was cooled to 0° C. and then sodium borohydride (2.0 g, 52 mmol) was added in portions. The reaction mixture was stirred at room temperature overnight and at 80° C. for 2 hours. The cooled reaction mixture was concentrated under reduced pressure to remove ethanol. The reaction mixture was diluted with water (30 mL) and sodium cyanide (4.9 g, 100 mmol) was added. The resulting mixture was stirred at 80° C. for 1 hour. The cooled reaction mixture was made basic (e.g. pH 13–14) with aqueous sodium hydroxide solution and then extracted with chloroform. The chloroform extract was washed with brine and dried over anhydrous sodium sulfate. The solvent was evaporated under reduced pressure and the resulting residue was purified by flash chromatography on a silica gel column (20 cm×3 cm). Elution with methanol and then methanol/ 30% aqueous ammonium hydroxide (100:1) gave 0.94 g (26%) of the title compound as a pale yellow oil.

TLC: Rf: 0.40; methanol:30% aqueous ammonium hydroxide; 30:1, v/v; silica gel. $^1$H NMR (CDCl$_3$) δ1.38 (s, 9H), 1.63 (m, 2H), 2.77 (t, 2H, J=6.5 Hz), 3.28 (m, 4H), 3.48 (m, 2H), 3.83 (s, 2H), 3.88 (s, 2H), 7.08 (d, 2H, J=7.5 Hz), 7.54 (t, 1H, J=7.5 Hz). $^{13}$C NMR (CDCl$_3$) δ28.39, 31.04, 43.84, 47.66, 48.01, 54.88, 58.68, 79.87, 119.42, 120.20, 136.93, 156.48, 158.99, 161.43. Mass spectrum (EI), m/z 338 (M)$^+$. Mass spectrum (CI$^+$ and FAB$^+$), m/z 339 (M+1)$^+$; mass spectrum (CI$^-$), m/z 337 (M−1)$^-$; mass spectrum (HREI), m/z 338.231 (M)$^+$ (C$_{17}$H$_3$N$_4$O$_3$ requires 338.231).

EXAMPLE 8

2-Aminomethylene-6-{[N1-(methyl-1-yl)-N2-1-propanol-3-yl]-1,2-diaminoethane}pyridine 7 (FIG. 2)

Trifluoroacetic acid (5.0 mL) was added to a stirred solution of 2-aminomethylene-6-{(N1-(methyl-1yl)-N2-(t-Boc)1-propanol-3-yl]-1,2-diaminoethane}pyridine (5, FIG. 2, 190 mg, 0.56 mmol) in dichloromethane (2.0 mL) at 0° C. The resulting reaction mixture was stirred at room temperature for 4 hours. The solvent was evaporated and the residue was purified by flash chromatography on a silica gel column (2×10 cm) using methanol and then methanol:30% ammonium hydroxide, 10:1, v/v, as the eluent. The product fractions were combined, concentrated and dried to give 75 mg (56%) of the title compound as a colorless oil.

TLC: Rf 0.40; 5:1 methanol:30% ammonium hydroxide, silica gel. $^1$H NMR (CDCl$_3$) δ1.57–1.72 (m, 2H), 2.57 (bs, H), 2.65–2.88 (m, 6H), 3.69 (t, 2H, J=5.6 Hz), 3.81 (s, 2H), 3.88 (s, 2H), 7.07 (dd, 2H, J=7.6, 2.8 Hz), 7.53 (t, 1H, J=7.6 Hz). $^{13}$C NMR (CDCl$_3$) δ31.27, 47.68, 48.78, 49.02, 49.36, 54.99, 63.19, 119.39, 120.25, 136.93, 159.22, 161.38. Mass spectrum (HRFAB), m/z 239.187 (m+1)$_+$ ($C_{12}H_{23}N_4O$ requires 239.187)

EXAMPLE 9

2-(N-benzoyl-aminomethylene)-6-{N1-[(benzoyl) methyl-1-yl]-N2[(t-Boc)-o-benzoyl-propanol-3-yl]-1,2-diaminoethane}pyridine 8 (FIG. 2)

Benzoyl chloride (0.5 mL, 0.71 g, 4.2 mmol) was added dropwise at room temperature to a stirred solution of 2-aminomethylene-6-{[N1-(methyl-1-yl)-N2-(t-Boc)1-propanol-3-yl]-1,2-diaminoethane}pyridine (5, FIG. 2, 40 mg, 0.11 mmol) in chloroform (5 mL) containing triethylamine (0.5, mL). After stirring at room temperature for 1 hour, the reaction mixture was diluted with chloroform. The solution was washed with aqueous sodium bicarbonate solution and brine. The chloroform solution was dried ($Na_2SO_4$), filtered, concentrated under reduced pressure, and the resulting residue was purified by flash chromatography on a silica gel column (10 cm×2 cm). Elution with hexanes-ethyl acetate (1:1, v/v) and 100% ethyl acetate afforded 60 mg (78%) of the tribenzoylated title compound as a pale yellow oil.

TLC: Rf 0.30; hexanes:ethyl acetate; 1:2, v/v; silica gel. $^1$H NMR ($CDCl_3$) δ1.34 (s, 9H), 1.70 (m, 2H), 3.20–3.70 (m, 6H), 4.25–4.38 (m, 2H), 4.74 (s, 2H), 4.77 (s, 2H), 7.00–8.10 (m, 18H). Mass spectrum (electrospray), m/z 651 (M+1)$^+$; 673 (M+Na)$^+$.

EXAMPLE 10

2-[Bis-N,N-(methyl-3-methylbenzoate-3-yl) aminamethyl]-6-{[N1-methyl-N1-(methyl-3-methylbenzoate-3-yl)-N2-(t-Boc)1-propanol]-1,2-diaminoethane}pyridine 10 (FIG. 3); 2-[N-(methyl-3-methylbenzoate-3-yl)aminoetyhl]-6-{[N1-methyl-N1-(methyl-3-methylbenzoate-3-yl)-N2-(t-Boc)1-propanol]-1,2-diaminoethane}pyridine 11; and 2-[bis-N,N-(methyl-3-methylbenzoate-3-yl) aminomethyl]-6-{[N1-methyl-N2-(t-Boc)1-propanol]-1,2-diaminoethane)pyridine 11 (FIG. 4)

A solution of methyl 3-bromomethyl benzoate (135 mg, 0.59 mmol, 1.98 eq) in acetonitrile (5 mL) was added to a stirred mixture of 2-aminomethylene-6-{[N1-(methyl-1yl)-N2-(t-Boc)l-propanol-3-yl]-1,2-diaminoethane}pyridine 5 (FIG. 1) (100 mg, 0.297 mmol) and potassium carbonate (170 mg, 1.23 mmol) in acetonitrile (12 mL). The resulting reaction mixture was stirred at room temperature for 6 hours. The solvent was evaporated under reduced pressure. The residue was dissolved in water and chloroform. The layers were separated and the aqueous phase was extracted with chloroform. The organic extract was washed with brine, dried ($Na_2SO_4$), and filtered. The solvent was evaporated and the residue was purified by flash chromatography on a silica gel column (12 cm×2 cm). Elution with hexanes:ethyl acetate (1:1, v/v) followed by ethyl acetate afforded 90 mg (39%) of the trisubstituted product 10 as a colorless oil.

TLC: Rf: 0.52; ethyl acetate; silica gel. The column was further eluted with ethyl acetate:methanol (10:1 and 5:1, v/v) giving 80 mg (42%) of the mixture of di-substituted products 11 as a pale yellow oil. TLC: Rf: 0.42; ethyl acetate: methanol; 5:1, v/v; silica gel.

Product 10: $^1$H NMR ($CDCl_3$) δ1.24 (s, 9H), 1.40–1.60 (m, 2H), 2.56–2.68 (m, 2H), 3.15–3.35 (m, 4H), 3.38–3.54 (m, 2H), 3.58–3.78 (m, 10H), 3.88, 3.89 (ds, 9H), 7.30–7.48 (m, 4H), 7.50–7.70 (m, 4H), 7.83–8.07 (m, 6H). $^{13}$C NMR ($CDCl_3$) δ28.21, 30.51, 43.05, 44.98, 52.08, 57.92, 58.22, 58.68, 59.68, 60.43, 80.02, 120.99, 128.42, 129.75, 129.95, 130.21, 133.33, 137.06, 139.49, 139.68, 156.70, 158.71, 158.85, 167.08. Mass spectrum (electrospray), m/z 783 (M+1)$^+$.

Products 11: $^1$H NMR ($CDCl_3$) δ1.28 (s, 9H), 1.45–1.60 (m, 2H), 2.64 (t, 2H, J=6.5 Hz), 2.88 (bs, 1H, NH), 3.15–3.32 (m, 4H), 3.38–3.50 (m, 2H), 3.70 (s, 2H), 3.76 (s, 2H), 3.80–3.95 (m, 10 H), 7.08–7.18 (m, 1H), 7.27–7.42 (m, 3H), 7.46–7.68 (m, 3H), 7.83–8.05 (m, 4H). Mass spectrum (electrospray), m/z 635 (M+1)$^+$.

EXAMPLE 11

N-t-Boc-2-amino-1-bromoethane 2-bromoethylamine hydrobromide (14.3 g, 70 mmol) was dissolved in $CH_3CN$ (250 mL) and triethyl amine (11 mL, 77 mmol) and di-t-butyl dicarbonate (15.2 mL, 66.5 mmol) was added. The reaction mixture was stirred at room temperature for 12 hours under an atmosphere of argon. Saturated $NaHCO_3$ (200 mL, aq) was added and stirring was continued for 15 minutes. The mixture was poured into a separatory funnel and extracted several times with ether. The combined ether extracts were dried over $Na_2SO_4$. The dried ether layer was filtered and concentrated in vacuo to give 15.28 g (97.4%) of the title compound.

TLC: Rf 0.7; 10% MeOH:$CH_2Cl_2$. $^1$H NMR ($CDCl_3$) δ1.5 (s, 9H, t-butyl $CH_3$), 3.5 (m, 4H, $CH_2$), 5.1 (s, 1H, NH). $^{13}$C NMR ($CDCl_3$) δ28.3 ($CH_3$), 32.7 ($CH_2$), 42.3 ($CH_2$), 79.7 (C($CH_3$)$_3$), 155.5 (CO).

EXAMPLE 12

N-t-Boc-(2-azido)-1-aminoethane

N-t-Boc-2-amino-1-bromoethane (15.28 g, 68.2 mmol) was suspended in DMF (200 mL) and sodium azide (5.0 g, 75 mmol) was added. The reaction mixture was stirred at about 80° C. for 12 hours under an atmosphere of argon. The reaction mixture was cooled and diluted with ether (400 mL). The reaction mixture was washed five times with saturated NaCr and dried over $Na_2SO$. The dried ether layer was filtered and concentrated in vacuo to give 9.8 g (77.1%) of the title compound.

TLC (Rf: 0.4; 20% EtOAc/Hexane). $^1$H NMR ($CDCl_3$,) δ1.4 (s, 9H, t-butyl $CH_3$), 3.2 (t, 2H, $CH_2$), 3.3 (m, 2H, $CH_2$), 4.9 (s, 1H, NH). $^{13}$MNR ($CDCl_3$) δ28.2 ($CH_3$), 40 ($CH_2$), 51.1 ($CH_2$), 79.7 (C($CH_3$)$_3$), 155.7 (CO).

EXAMPLE 13

N-t-Boc-diaminoethane

To N-t-Boc-(2-azido)-1-aminoethane (9.8 g, 52.6 mmol), in THF (200 mL), was added $H_2O$ (0.8 mL) and triphenyl phosphine (15 g, 58 mmol). The reaction mixture was stirred at about 80° C. for 12 hours under an atmosphere of argon. The reaction mixture was evaporated to a white solid residue. $NaH_2PO_4$ (200 mL, 0.5 M, ag) was added and the mixture was stirred for about 15 minutes. The mixture was washed with EtOAc. The aqueous layer was separated and made basic with 3 N NaOH. The resulting mixture was extracted with ether and the combined ether extracts dried over $Na_2SO_4$. The dried ether layer was filtered and concentrated in vacuo to give 8.1 g (96.5%) of the title compound.

TLC: Rf 0.2; 20% MeOH/$CH_2Cl_2$. $^1$H NMR ($CDCl_3$) δ1.3 (s, 2H, $NH_2$), 1.4 (s, 9H, t-butyl $CH_3$), 2.8 (t, 2H, $CH_2$), 3.2 (m, 2H, CH$_2$), 4.8 (s, 1H, NH). $^{13}$C NMR (CDCl$_3$) δ28.4 (CH$_3$), 41.9 (CH$_2$), 43.5 (CH$_2$), 79.2 (C(CH$_3$)$_3$), 156.2 (CO).

The title compound was also prepared according to the procedure of Saari, et. al., *J. Med. Chem.*, 1990, 33 97–101.

EXAMPLE 14

N1-(t-Boc)-N2-tosyl-diaminoethane

To a solution of N-(t-Boc)-diaminoethane (153 g, 0.95 mol) and triethylamine (202 mL) in CH$_2$Cl$_2$ (1400 mL) at room temperature, was added p-toluenesulfonyl chloride (190 g, 1.0 mol). The reaction was stirred for 16 hours, partitioned with water and separated. The organic phase was dried (MgSO$_4$), filtered, and concentrated. The resulting residue was triturated with hexane to give 36 g, (84%) of the title compound as a white solid.

$^1$H NMR (CDCl$_3$) δ1.41 (s, 9H, (CH$_3$)$_3$); 2.40 (s, 3H, CH$_3$); 3.03 (m, 2H, CH$_2$); 3.21 (m, 2H, CH$_2$); 5.2 (brs, 1H, NH); 7.29 (d, 2H, Ar); 7.34 (d, 2H, Ar).

EXAMPLE 15

N1-(t-Boc)-N2-[(3-chloropropyl)]tosyl] diaminoethane

A solution of N1-(t-Boc)-N2-tosyl-diaminoethane (297 g, 0.94 mol), 1-(methanesulfonyl)-3-chloropropanol (188 g, 1.09 mol) and Cs$_2$CO$_3$ (344 g, 1.06 mol) in acetone(9 L) was heated at reflux for 16 hours. The reaction mixture was concentrated, partitioned between CH$_2$Cl$_2$ and H$_2$O, separated, dried (MgSO4), filtered and concentrated. Trituration of the resulting white solid with ether:hexane (1/1, v/v), gave 327 g (89%), of the title compound. mp 95–96° C. $^1$H NMR (CDCl$_3$) δ1.42 (s, 9H, t-Butyl); 2.0 (m, 2H, CH$_2$); 2.41 (s, 3H, CH$_3$), 3.22 (m, 6H, CH$_2$); 3.55 (m, 2H, CH$_2$); 4.91 (bs, 1H, NH); 7.30 (d, 2H, ArH); 7.66 (d, 2H, ArH). $^{13}$C NMR (CDCl$_3$) δ21.51, 28.37, 37.34, 40.31, 41.45, 47.37, 48.79, 79.59, 127.27, 129.88, 135.70, 143.71. MS (FAB) m/z 523 (m+Cs)$^+$. Anal. Calcd for C$_{17}$H$_{27}$N$_2$OSCl: C, 52.23; H, 6.96; N, 7.17. Found: C, 52.13; H, 6.93; N, 7.17.

EXAMPLE 16

N1-(t-Boc)-N2-[(3-phthalimidooxypropyl)tosyl] diaminoethane

A suspension of N1-(t-Boc)-N2-[(3-chloropropyl)-tosyl] diaminoethane (27 g, 0.69 mol), sodium iodide (13.5 g, 0.09 mol), sodium carbonate (10.8 g, 0.10 mol) and N-hydroxyphthalimide (97%, 16.5 g, 0.1 mol) in DMF (1000 mL) was stirred vigorously at 80° C. for 24 hours. The reaction was concentrated, partitioned between CH$_2$Cl$_2$ and H$_2$O and washed thoroughly with H$_2$O (3×200 mL). The organic layer was separated, dried (MgSO4), filtered and concentrated. The resulting solid was recrystallized from methanol to give 20.0 g (56%) of the title compound as a white solid.

mp 111–112° C. $^1$H NMR (CDCl$_3$) δ1.41 (s, 9h, t-butyl); 2.0 (m, 2H, CH$_2$); 2.41 (s, 3H, Ar—CH$_3$); 3.20 (m, 6H, CH$_2$); 4.25 (t, 2H, CH$_2$); 5.07 (bs, 1H, NH); 7.29 (d, 2 h, ArH); 7.67 (m, 6H, ArH). $^{13}$C NMR (CDCl$_3$) δ21.51, 28.39, 40.00, 46.73, 49.06, 75,74, 79.00, 123.58, 127.32, 127.34, 128.95, 129.85, 134.56, 135.82, 143.56, 156.28, 163.61. MS (FAB) m/z 518(m+H)$^+$. Anal. Calcd for C$_{25}$H$_{31}$N$_3$O$_7$S: C, 58.01; H, 6.04; N, 8.12 Found: C, 58.02; H, 5.84; N, 8.12.

EXAMPLE 17

N1-(t-Boc)-N2-[(3-O-aminopropanol-1-yl)tosyl] diaminoethane

A solution of N1-(t-Boc)-N2-[(3-phthalimidooxypropyl)-tosyl]diaminoethane (49 g, 95 mmol) and hydrazine (30 mL, 0.94 mol) in methanol (1500 mL) was stirred at 35° C. for 3 hours. The solid was then filtered off, toluene was added to the mother liquor, and the mother liquor was concentrated. The resultant oil was chromatographed on silica gel (EtOAC) to afford 27 g. (73%) of the title compound as a colorless oil.

$^1$H NMR (CDCl$_3$) δ1.39 (s, 9H, (CH$_3$)$_3$); 1.78 (m, 2H, CH$_2$); 2.32 (s, 3H, CH$_3$); 3.06–3.23 (m, 6H, CH$_2$); 3.59 (m, 2H, CH$_2$); 5.21 (bs, 1H, NH); 5.34 (s, 2H, NH$_2$); 7.20 (d, 2H, Ar); 7.66 (d, 2H, Ar). $^{13}$C NMR (CDCl$_3$) δ21.38, 28.33, 39.89, 46.73, 48.38, 72.50, 79.17, 127.44, 129.74, 136.00, 143.35, 156.00. MS (FAB) m/z 338 (m+H)$^+$. Anal. Calcd for C$_{17}$H$_{29}$N$_3$O$_5$S: C, 52.69; H, 7.54; N, 10.84. Found: C, 52.46; H, 7.61; N, 11.02.

EXAMPLE 18

N2-[(3-O-aminopropanol-1-yl)tosyl] diaminoethane.HCl

A solution of N1-(t-Boc)-N2-(3-O-aminopropanol-1-yl) tosyl]diaminoethane (11.5 g, 30 mmol) in ethyl acetate (50 mL) was added to a solution of HCl (gas) (88 g) dissolved in ethyl acetate (1000 mL). After 1 hour the product was filtered off and washed with ether. After drying 9.8 g (92%) of the title compound was isolated as a colorless oil (m.p. 205–206° C.).

$^1$H NMR (DMSO) δ1.84 (m, 2H, CH$_2$); 2.42 (s, 3H, CH$_3$); 2.95 (m, 2H, CH$_2$); 3.17 (m, 2H, CH$_2$), 3.29 (m, 2H, CH$_2$); 4.07 (m, 2H, CH$_2$); 7.47 (d, 2H, Ar); 7.73 (d, 2H, Ar); 8.24 (bs, 2H, NH$_2$); 11.1 (bs, 2H, ONH$_2$). $^{13}$C NMR (CDCl$_3$) δ21.03, 26.60, 38.09, 45.02, 46.09, 71.65, 127.13, 130.06, 135.00, 143.73. MS (FAB) m/z 208 (m+H)$^+$. Anal. Calcd for C$_{12}$H$_{21}$N$_3$O$_3$S.2HCl: C, 40.00; H, 6.43; N, 11.66. Found: C, 39.94; H, 6.49; N, 11.35.

EXAMPLE 19

Preparation of N1-[(tosyl)-O-aminopropanol-3-yl] diainoethane 2 (FIG. 2)

N1-[(tosyl)-O-aminopropanol-3-yl]diaminoethane.2HCl (9.0 g, 22.7 mmol) was treated with a solution of sodium hydroxide (5 g, 0.125 mol) in water (150 mL) for 1 hour. The solution was diluted with brine (100 mL) and then extracted with ethyl acetate. The combined organic extract was dried (Na$_2$SO$_4$) and filtered. The solvent was evaporated under reduced pressure and the residue was dried under high vacuum. The title compound 6.5 g (99%) was obtained as a colorless oil.

$^1$H NMR (CDCl$_3$) δ1.75–1.92 (m, 2H), 2.41 (s, 3H), 2.85 (t, 2H, J=6.2 Hz),3.09–3.24 (m, 4H), 3.65 (t, 2H, J=6.0 Hz), 7.29 (d, 2H, J=8.4 Hz), 7.68 (d, 2H, J=9.0 Hz). HRMS (FAB) m/z 288.137 (M+H)$^+$ ([C$_{12}$H$_{21}$N$_3$O$_3$S+H] requires 288.138).

EXAMPLE 20

2-(Aminomethyl)-6-[N1-methyl-N2-[(tosyl)-1-propanol]-1,2-diaminoethane]pyridine 6 (FIG. 2)

A solution of N1-[(tosyl)]-O-aminopropanol-3-yl] diaminoethane (2, 1.1 g, 3.8 mmol) in ethanol (10 mL) was added to a stirred solution of nickel(II) chloride hexahydrate (0.88 g, 3.7 mmol) in ethanol:water (1:1, v/v)(30 mL). Pyridine-2,6-dicarboxaldehyde (4, Aldrich, 0.5 g, 3.7 mmol) was added to the above solution followed by glacial acetic acid (0.4 mL). The resulting deep blue solution was stirred at room temperature for 2 hours, and then at 80° C. for 6 hours. The solution was cooled to 0° C. and then sodium borohydride (1.2 g, 31 mmol) was added in portions. The reaction mixture was stirred at room temperature overnight and at 80° C. for 2 hours. The cooled reaction mixture was concentrated under reduced pressure to remove ethanol. The reaction mixture was diluted with water (20 mL) and sodium cyanide (1.81 g, 37 mmol) was added. The resulting mixture was stirred at 80° C. for 1 hour. The cooled reaction mixture was made basic (e.g. pH 13–14) with aqueous sodium hydroxide and then extracted three times with chloroform. The chloroform extract was washed with brine, dried ($Na_2SO_4$), and filtered. The solvent was evaporated under reduced pressure and the resulting residue was purified by flash chromatography on a silica gel column (20 cm×3 cm). Elution with methanol and then methanol:30% aqueous ammonium hydroxide (100:1, v/v) gave 0.30 g (21%) of the title compound as a pale yellow oil.

TLC: Rf 0.42; methanol:30% aqueous ammonium hydroxide; 20:1, v/v; silica gel. $^1$H NMR ($CDCl_3$) δ1.65–1.80 (m, 2H), 2.36 (s, 3H), 2.77 (t, 2H, J=6.0 Hz), 3.05–3.20 (m, 4H), 3.55 (t, 2H, J=5.7 Hz), 3.79 (s, 2H), 3.86 (s, 2H), 7.05 (d, 2H, J=7.6 Hz), 7.21 (d, 2H, J=8.0 Hz), 7.51 (t, 1H, J=7.6 Hz), 7.61 (d, 2H, J=8.0 Hz). Mass spectrum (FAB), m/z 393 (M+1)$^+$, 525 (M+Cs)$^+$. Mass spectrum (electrospray), m/z 393 (M+1)$^+$. $^{13}$C NMR ($CDCl_3$) δ21.46, 31.93, 46.67, 47.40, 48.13, 49.46, 54.54, 58.50, 119.67, 120.50, 127.5, 129.69, 135.74, 137.08, 143.35, 158.61, 161.04. HRMS (FAB) m/z 393.197 (m+H)$^+$ ([$C_{19}H_{28}N_4O_3S$+H] requires 393.196).

EXAMPLE 21

2-[Bis-N,N-(methyl-3-methylbenzoate-3-yl) aminomethyl]-6-{[N1-methyl-N1-(methyl-3-methylbenzoate-3-yl)-N2-(tosyl)1-propanol]-1,2-diaminoethane}pyridine 12 (FIG. 3)

A solution of methyl m-bromomethylbenzoate (137 mg, 0.6 mmol, 1.8 eq) in acetonitrile (5 mL) was added to a stirred mixture of 2-(aminomethyl)-6-[N1-methyl-N2-] (tosyl)-1-propanol-1,2-diaminoethanelpyridine 6 (FIG. 1) (130 mg, 0.33 mmol) and potassium carbonate (0.20 g, 1.4 mmol) in acetonitrile (8 mL). The resulting reaction mixture was monitored by TLC and stirred at room temperature for 7 hours. The solvent was evaporated and the residue was dissolved in water:chloroform. The layers were separated and the aqueous phase was extracted with chloroform. The chloroform extract was dried ($Na_2SO_4$), filtered, and concentrated. The residue was purified by flash chromatography on a silica gel column (15 cm×2 cm). Elution with hexanes: ethyl acetate (5:1, v/v) and then ethyl acetate afforded 110 mg (49%) of the title compound as a colorless oil.

TLC: Rf: 0.37; hexanes:ethyl acetate; 1:2, v/v; silica gel. $^1$H NMR ($CDCl_3$) δ1.48–1.60 (m, 2H), 2.35 (s, 3H), 2.66 (t, 2H, J=6.5 Hz), 3.07–3.25 (m, 4H), 3.48–3.60 (m, 2H), 3.64 (s, 4H), 3.67 (s, 2H), 3.71 (s, 2H), 3.75 (s, 2H), 3.89, 3.90 (ds, 9H), 7.14–7.70 (m, 13H), 7.84–8.08 (m, 6H). $^{13}$C NMR ($CDCl_3$) δ21.45, 31.25, 45.64, 46.77, 52.12, 52.80, 57.95, 58.68, 59.67, 60.28, 121.12, 121.36, 127.03, 128.44, 129.68, 129.97, 130.22, 133.38. 133.51, 136.80 137.06, 139.51, 143.20, 158.33, 158.94, 167.13. Mass spectrum (electrospray), m/z 837 (M+1)$^+$. Mass spectrum (HRFRAB), m/z 837.356 (M+1)$^+$ ($C_{46}H_{52}N_4SO_9$ requires 837.353).

When Hünig's base was used as a base and chloroform was used as solvent, the reaction was completed in 48 hours. The title compound was isolated with the same chromatographic, and spectroscopic properties.

EXAMPLE 22

2-[Bis-N,N-(methyl-3-methylbenzoate-3-yl) aminometyhl]-6-{[N1-methyl-N1-(methyl-3-methylbenzoate-3-yl)-N2-(tosyl)1-(O-acetyl) propanol]-1,2-diaminoethane}pyridine 13 (FIG. 3)

Acetyl chloride (0.5 mL) was added dropwise to a stirred solution of 2-[bis-N,N-(methyl-3-methylbenzoate-3-yl) aminomethyl]-6-([N1-methyl-N1-(methyl-3-methylbenzoate-3-yl)-N2-(tosyl)1-propanol]-1,2-diaminoethane}pyridine 12 (40 mg, 0.047 mmol) and triethylamine (0.5 mL) in chloroform (5 mL). The resulting reaction mixture was stirred at room temperature for 1 hour and diluted with chloroform (50 mL). The chloroform solution was washed 3 times with an aqueous solution of sodium bicarbonate and once with brine. The dried ($Na_2SO_4$) chloroform phase was filtered, concentrated under reduced pressure, and the resulting residue purified by flash chromatography on a silica gel column (12 cm×2 cm). Elution with hexanes:ethyl acetate (2:1, v/v) and then ethyl acetate afforded 40 mg (95%) of the title compound as a pale yellow oil.

TLC: Rf: 0.42; hexanes:ethyl acetate; 1:1, v/v; silica gel. $^1$H NMR ($CDCl_3$) δ1.55–1.70 (m, 2H), 1.94 (s, 2H), 2.37 (s, 3H), 2.60–2.73 (m, 2H), 2.99–3.10 (m, 2H), 3.13–3.25 (m, 2H), 3.25–3.40 (m, 2H), 3.64 (s, 4H), 3.67(s, 2H), 3.71 (s, 2H), 3.76 (s, 2H), 3.88, 3.91 (ds, 9H), 7.20 (d, 2H, J=8.3 Hz), 7.30–7.70 (m, 9H), 7.85–8.10 (m, 6H). Mass spectrum (FAB), m/z 879 (M+1)$^+$ Mass spectrum (HRFAB); m/z 1011.258 (M+Cs)$^+$, ($C_{48}H_4N_4SO_{10}Cs$ requires 1011.261).

EXAMPLE 23

Figure 5:
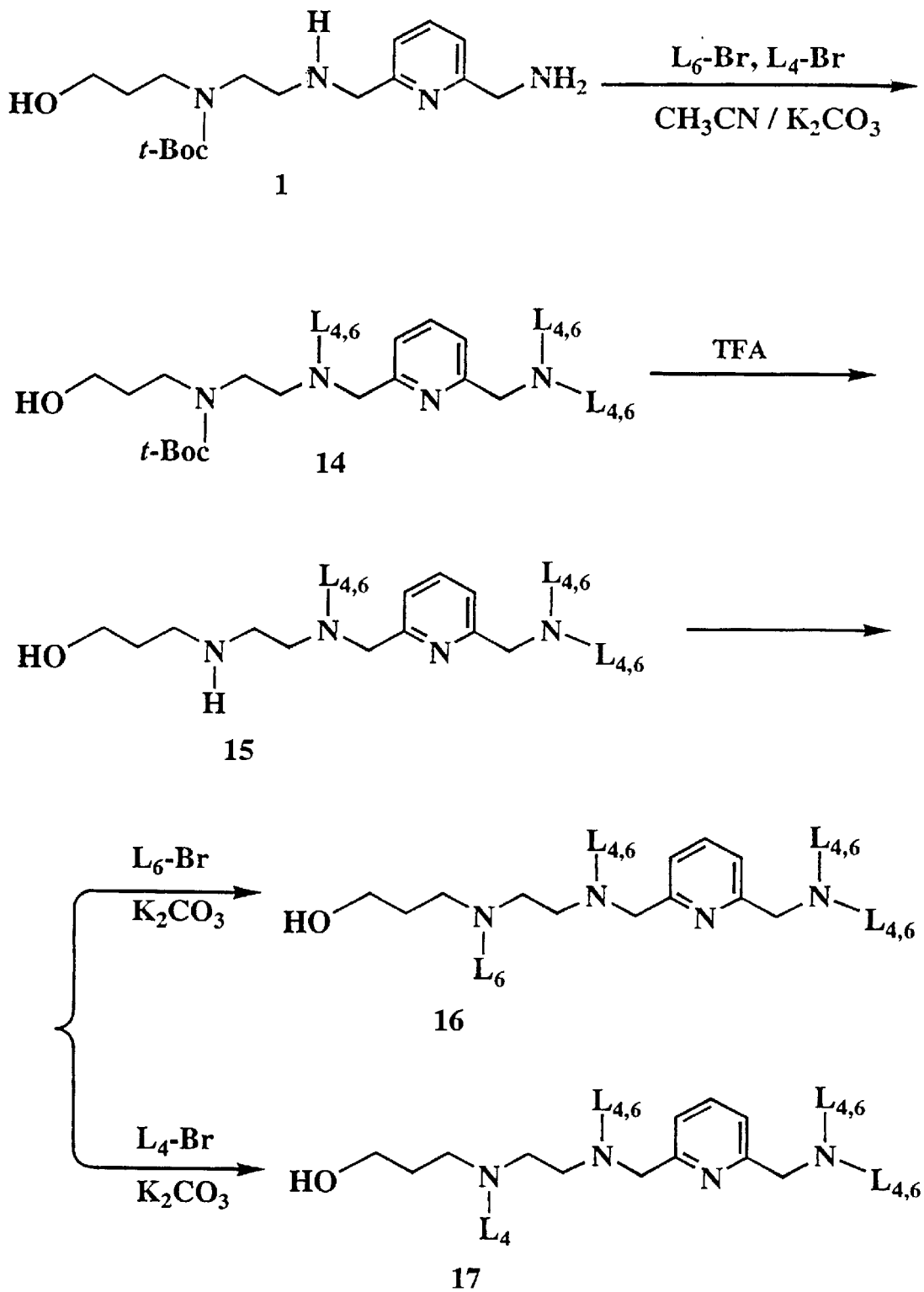
FIG. 5 shows processes for the synthesis of libraries of compounds according to the invention.

Preparation of Library 14 (FIG. 5)

A solution of α-bromo-m-xylene (0.494 g, 2.66 mmol, 2 eq) and methyl 3-bromomethylbenzoate (0.61 g, 2.66 mmol, 2 eq) in acetonitrile (25 mL) was added dropwise at room temperature to a stirred mixture of 2-aminomethyl-6-{[N1-methyl-N2-(t-Boc)1-propanol]-1,2-diaminoethane}pyridine (0.45 g, 1.33 mmol) and potassium carbonate (2.67 g, 19.3 mmol) in acetonitrile (40 mL). The resulting reaction mixture was stirred at room temperature overnight. The solvent was evaporated and the resulting residue was dissolved in water and chloroform. The layers were separated and the aqueous layer was extracted with chloroform. The chloroform extract was washed with brine, dried ($Na_2SO_4$), and filtered. The solvent was evaporated and the resulting residue was purified by flash chromatography on a silica gel column (12 cm×3 cm). Elution with hexanes:ethyl acetate (10:1, v/v) and then ethyl acetate afforded 0.88 g (93%) of Library 35 as a pale yellow oil.

TLC: Rf 0.31, 0.42, 0.54 and 0.62; hexanes:ethyl acetate; 1:2, v/v; silica gel. $^1$H NMR ($CDCl_3$) δ1.26 (s, 9H), 1.40–1.60 (m, 2H), 2.32, 2.34 (ds, 4.5H), 2.57–2.68 (m, 2H), 3.15–3.35 (m, 4H), 3.40–3.52 (m, 2H), 3.55–3.78 (10H), 3.91, 3.92 (ds, 4.5H), 6.98–7.08 (m, 2H), 7.10–7.24 (m, 4H), 7.30–7.72 (m, 6H), 7.85–8.10 (m, 3H). Mass spectrum (electrospray), m/z 651, 695, 739, 783 (M+1)$^+$; 673, 717, 761, 805 (M+Na)$^+$.

EXAMPLE 24

Deprotection of Library 14, Preparation of Library 15 (FIG. 5)

Trifluoroacetic acid (TFA) (8 mL) was added to a flask containing Library 14 (0.75 g, 1.04 mmol) at 0° C. The resulting solution was stirred at room temperature for 3 hours. The TFA was evaporated under reduced pressure and the residue was dissolved in chloroform (200 mL). The resulting solution was washed 3 times with saturated solution of aqueous potassium carbonate, dried ($Na_2SO_4$), and filtered. The solvent was evaporated and the residue was purified by flash chromatography on a silica gel column (12 cm×3 cm). Elution with methanol and then methanol:30% aqueous ammonium hydroxide (100:1, v/v) afforded 0.50 g (78%) of Library 15 as a pale yellow oil.

TLC: Rf 0.43; methanol:30% aqueous ammonium hydroxide; 100:1, v/v; silica gel. $^1$H NMR ($CDCl_3$) δ1.52–1.67 (m, 2H), 2.32, 2.34 (ds, 4.5H), 2.56–2.68 (m, 6H), 3.54–3.78 (m, 12H), 3.90, 3.92 (ds, 4.5H), 6.98–7.23 (m, 6H), 7.27–7.70 (m, 6H), 7.86–8.09 (m, 3H). Mass spectrum (electrospray), m/z 551, 595, 639, 683 $(M+1)^+$.

EXAMPLE 25

Preparation of Library 16 (FIG. 5)

A solution of α-bromo-m-xylene (85 μL, 116 mg, 0.63 mmol, 1.5 eq) in acetonitrile (5 mL) was added at room temperature to a stirred mixture of Library 15 (0.26 g, 0.42 mmol) and potassium carbonate (0.8 g, 5.7 mmol) in acetonitrile (10 mL). The resulting reaction mixture was stirred at room temperature for 23 hours. The solvent was evaporated under reduced pressure and the residue was dissolved in water:chloroform. The layers were separated and the aqueous layer was extracted with chloroform. The chloroform extract was dried ($Na_2SO_4$), filtered, and the solvent evaporated. The residue was purified by preparative thin layer chromatography (TLC) using ethyl acetate: methanol (20:1, v/v) as the developing agent giving 160 mg (53%) of the Library 16 as a colorless oil.

TLC Rf 0.36–0.54; ethyl acetate:methanol; 20:1, v/v, silica gel. $^1$H NMR ($CDCl_3$) δ1.55–1.70 (m, 2H), 2.25, 2.30, 2.34, (ts, 7.5H), 2.47–2.68 (m, 6H), 3.38–3.74 (m, 14H), 3.89, 3.92 (ds, 4.5H), 6.91–7.25 (m, 10H), 7.28–7.68 (m, 6H), 7.84–8.10 (m, 3H). Mass spectrum (electrospray), m/z 655, 699, 743, 787 $(M+1)^+$; 677, 721, 765, 809 $(M+Na)^+$.

EXAMPLE 26

Preparation of Library 17 (FIG. 5)

Library 17 was prepared using the procedure above for Library 16 using Library 15 (0.23 g, 0.37 mmol), methyl 3-bromomethylbenzoate (0.13 g, 0.56 mmol, 1.5 eq), and potassium carbonate (0.8 g, 5.7 mmol) in acetonitrile (15 ml). Library 17, 0.25 g (88%) was obtained as a pale yellow oil.

TLC: Rf 0.40–0.58; ethyl acetate:methanol; 20:1, v/v; silica gel. $^1$H NMR ($CDCl_3$) δ1.55–1.70 (m, 2H), 2.29, 2.33 (ds, 4.5H), 2.47–2.68 (m, 6H), 3.44–3.72 (m, 14H), 3.88, 3.89, 3.91 (ts, 7.5H), 6.97–7.22 (m, 7H), 7.28–7.68 (m, 7H), 7.78–8.08 (m, 5H). Mass spectrum (electrospray), m/z 699, 743, 787, 831 (M+1); 721, 765, 809, 853 $(M+Na)^+$.

EXAMPLE 27

Preparation of Library 18 (FIG. 6)

A solution of benzyl bromide (123 μL, 171 mg, 1.0 mmol), 3-fluorobenzylbromide (124 μL, 189 mg, 1.0 mmol), α-bromo-m-xylene (141 μL, 185 mg, 1.0 mmol), methyl-3-bromomethylbenzoate (229 mg, 1.0 mmol), 3-nitrobenzyl bromide (216 mg, 1.0 mmol) and α'-bromo-α,α,α-trifluoro-m-xylene (155 μL, 239 mg, 1.0 mmol) in acetonitrile (30 mL) was added to a stirred mixture of 2-aminomethyl-6-{[N1-methyl-N2-(t-Boc)1-propanol]-1,2-diaminoethane}pyridine 5 (560 mg, 1.65 mmol) and potassium carbonate (3.5 g, 25.0 mmol) in acetonitrile (60 mL). The resulting reaction mixture was stirred at room temperature overnight. The work-up and purification were the same as those for Library 14. Library 18, 0.89 g (76%) was obtained as a pale yellow oil.

TLC: Rf 0.30–0.70; hexanes:ethyl acetate; 1:2, v/v; silica gel. $^1$H NMR ($CDCl_3$) δ1.27 (s, 9H), 1.40–1.70 (m, 2H), 2.32, 2.34 (ds, 1.5H), 2.47–2.72 (m, 2H), 3.15–3.35 (m, 4H), 3.38–3.52 (m, 2H), 3.54–3.80 (m, 12H), 3.91, 3.92 (ds, 1.5H), 6.90–8.32 (m, 15-1/6H). Mass spectrum (electrospray), m/z 609–813 $(M+1)^+$.

EXAMPLE 28

Preparation of Library 19 (FIG. 6)

A solution of benzyl bromide (25 μL, 35 mg, 0.2 mmol), 3-fluorobenzyl bromide (25 μL, 38 mg, 0.2 mmol), α-bromo-m-xylene (28.5 μL, 37 mg, 0.2 mmol), methyl 3-bromomethylbenzoate (47.2 mg, 0.2 mmol), 3-nitrobenzyl bromide (44 mg, 0.2 mmol) and α-bromo-α',α,α-trifluoro-m-xylene (31 μL, 48 mg, 0.2 mmol) in acetonitrile (10 mL) was added to a stirred mixture of 2-(Aminomethyl)-6-[N1-methyl-N2-[(tosyl)-1-propanol]-1,2-diaminoethane] pyridine 6 (FIG. 2) (130 mg, 0.33 mmol) and potassium carbonate (0.8 g, 5.7 mmol) in acetonitrile (10 mL). The resulting reaction mixture was stirred at room temperature overnight. The work-up and purification were the same as those for library 18 to give 180 mg (71%) of library 19 as a pale yellow oil.

TLC: Rf: 0.30–0.70; hexanes-ethyl acetate, 1:4, v/v; silica gel. $^1$H NMR ($CDCl_3$) δ1.27 (s, 9H), 1.41–1.62 (m, 2H), 2.32, 2.34 (ds, 1.5H), 2.38 (s. 3H), 2.58–2.80 (m, 2H), 3.04–3.28 (m, 4H), 3.50–3.85 (m, 12H), 3.91, 3.92 (ds, 1.5H), 6.85–8.30 (m, 19-1/6H); mass spectrum (electrospray), m/z 663–867 $(M+1)^+$.

EXAMPLE 29

Deprotection of Library 18, Preparation of Library 20 (FIG. 6)

Library 20 was synthesized as above for Library 15 from 0.77 g (1.08 mmol) of Library 18, and TFA (8 mL). Library 20, 0.63 g (95%) was obtained as a pale yellow oil.

TLC: Rf 0.36–0.50; methanol:30% aqueous ammonium hydroxide; 100:1, v/v; silica gel. $^1$H NMR ($CDCl_3$) δ1.49–1.68 (m, 2H), 2.32, 2.34 (ds, 1.5H), 2.53–2.76 (m, 6H), 3.50–3.80 (m, 14H), 3.90, 3.92 (ds, 1.5H), 6.85–8.30 (m, 15-30 1/6H). Mass spectrum (electrospray), m/z 509–713 $(M+1)^+$.

EXAMPLE 30

Preparation of Library 25 (FIG. 6)

A solution of methyl 3-bromomethylbenzoate (56 mg, 0.24 mmol, 1.5 eq) in acetonitrile (2 mL) was added to a stirred mixture of Library 20 (100 mg, 0.163 mmol) and $K_2CO_3$ (0.4 g, 2.8 mmol) in acetonitrile (6 mL). The resulting reaction mixture was stirred at room temperature overnight. The solvent was evaporated and the residue was dissolved in water:chloroform. The layers were separated and the aqueous layer was extracted with chloroform. The chloroform extract was washed with brine, dried ($Na_2SO_4$), and filtered. The <solvent was evaporated and the residue was purified by preparative thin lager chromatography (TLC) using ethyl acetate:methanol (40:1, v/v) as the developing agent. Library 25, 60 mg (49%) was obtained as a colorless oil.

TLC: Rf 0.37–0.57; ethyl acetate:methanol; 40:1, v/v; silica gel. $^1$H NMR (CDCl$_3$) δ1.57–1.75 (m, 2H), 2.31, 2.33 (ds, 1.5H), 2.48–2.73 (m, 4H), 3.42–3.80 (m, 14H), 3.89, 3.91 (ds, 4.5H), 6.85–8.30 (m, 19-1/6H). Mass spectrum (eletrospray), m/z 656–860 (M)$^+$.

EXAMPLE 31

Preparation of Library 21 (FIG. 6)

Library 21 was synthesized as above for Library 25 using Library 20 (90 mg, 0.147 mmol), benzylbromide (27 μL, 38 mg, 0.22 mmol, 1.5 eq) and K$_2$CO$_3$ (0.4 g, 2.8 mmol) in acetonitrile (8 mL). After purification Library 21, 71 mg (701) was obtained as a colorless oil.

TLC: Rf 0.30–0.45; ethyl acetate:methanol; 20:1, v/v; silica gel. $^1$H NMR (CDCl$_3$) δ1.60–1.75 (m, 2H), 2.31, 2.33 (ds, 1.5H), 2.50–2.75 (m, 4H), 3.42–3.80 (m, 14H), 3.89, 3.91 (ds, 1.5H), 6.80–8.30 (m, 20-1/6H). Mass spectrum (electrospray), m/z 599–803 (M)$^+$.

EXAMPLE 32

Preparation of Library 23 (FIG. 6)

Library 23 was synthesized as above for Library 25 using Library 20 (90 mg, 0.147 mmol), 3-fluorobenzylbromide (30 μL, 46 mg, 0.244 mmol) and K$_2$CO$_3$ (0.45 g, 3.2 mmol) in acetonitrile (8 mL). After purification 45 mg (45%) of Library 23 was obtained as a colorless oil.

TLC: Rf 0.43–0.60; ethyl acetate:methanol; 40:1, v/v; silica gel. $^1$H NMR (CDCl$_3$) δ1.55–1.75 (m, 2H), 2.32, 2.34 (ds, 1.5H), 2.47–2.75 (m, 6H), 3.40–3.80 (m, 14H), 3.90, 3.92 (ds, 1.5H), 6.80–8.30 (m, 19-1/6H). Mass spectrum (electrospray), m/z 616–820 (M)$^+$.

EXAMPLE 33

Preparation of Library 24 (FIG. 6)

Library 24 was synthesized as above for Library 25 using Library 20 (90 mg, 0.147 mmol), 3-nitrobenzylbromide (48 mg, 0.22 mmol, 1.5 eq.) and K$_2$CO$_3$ (0.40 g, 2.8 mmol) in acetonitrile (8 mL). After purification Library 24, 45 mg (41%) was obtained as a pale yellow oil.

TLC: Rf 0.47–0.68; ethyl acetate:methanol; 50:1, v/v; silica gel. $^1$H NMR (CDCl$_3$) δ1.55–1.74 (m, 2H), 2.31, 2.33 (ds, 1.5H), 2.48–2.72 (m, 6H), 3.45–3.80 (m, 14H), 3.90, 3.92 (ds, 1.5H), 6.80–8.30 (m, 19-1/6H). Mass spectrum (electrospray), m/z 643–847 (M)$^+$.

EXAMPLE 34

Preparation of Library 26 (FIG. 6)

Library 26 was synthesized as above for Library 25 using Library 20 (85 mg, 0.139 mmol), α'-bromo-α,α-trifluoro-m-xylene (32 μL, 50 mg, 0.209 mmol, 1.5 eq) and K$_2$CO$_3$ (0.40 g, 2.8 mmol) in acetonitrile (8 mL). After purification Library 26, 75 mg (71%) was obtained as a pale yellow oil.

TLC: Rf 0.55–0.73; ethyl acetate:methanol; 50:1, v/v; silica gel. $^1$H NMR (CDCl$_3$) δ1.47–1.78 (m, 2H), 2.32, 2.34 (ds, 1.5H), 2.48–2.85 (m, 6H), 3.45–3.80 (m, 14H), 3.90, 3.92 (ds, 1.5H), 6.80–8.30 (m, 19-1/6H). Mass spectrum (electrospray), m/z 666–870 (M)$^+$.

EXAMPLE 35

Preparation of Library 22 (FIG. 6)

Library 22 was synthesized as above for Library 25 using Library 20, α-bromo-m-xylene (17 μL, 23.3 mg, 0.12 mmol, 1.2 eq) and K$_2$CO$_3$ (0.2 g, 1.4 mmol) in 6 mL acetonitrile. After purification Library 22 55 mg (78%) was obtained as a pale yellow oil.

TLC: Rf: 0.25–0.50; ethyl acetate-methanol, 20:1, v/v; silica gel. $^1$H NMR (CDCl$_3$) δ1.55–1.72 (m, 2H), 2.25 (s, 3H), 2.30, 2.34 (ds, 1.5H), 2.49–2.70 (m, 6H), 3.45 (s, 2H), 3.49–3.78 (m, 14H), 3.89, 3.92(ds, 1.5H), 6.85–8.30 (m, 19-1/6H). Mass spectrum (electrospray), m/z 613–817 (M+1)$^+$.

EXAMPLE 36

Preparation of Library 28 (FIG. 6)

Library 28 was synthesized as above for Library 25 using Library 20, (α-bromoacetonitrile (10 μL, 16.6 mg, 0.138 mmol, 1.38 eq) and K$_2$CO$_3$ (0.20 g, 1.4 mmol) in 5 mL of acetonitrile. After purification Library 28 37 mg (58%) was obtained as a pale yellow oil.

TLC: Rf: 0.48–0.69; ethyl acetate-methanol, 40:1, v/v; silica gel. $^1$H NMR (CDCl$_3$) d 1.57–1.74 (m, 2H), 2.30, 2.34 (ds, 1.5H), 2.56–2.80 (m, 6H), 3.38–3.82 (m, 16H), 5 3.91, 3.93 (ds, 1.5H), 6.85–8.30 (m, 15-1/6H); mass spectrum (electrospray), m/z S48–752 (M+1)$^+$.

EXAMPLE 37

Preparation of Library 29 (FIG. 6)

Library 29 was synthesized as above for Library 25 using Library 20, α-bromoacetamide (18.0 mg, 0.129 mmol, 1.29 eq) and K$_2$CO$_3$ (0.20 g, 1.4 mmol) in 5 mL of acetonitrile. The preparative TLC was developed by 3:1 ethyl acetate-methanol. After purification Library 29 35 mg (53%) was obtained as a pale yellow sticky oil.

TLC: Rf: 0.35–0.60; ethyl acetate-methanol, 3:1, v/v; silica gel. $^1$H NMR (CDCl$_3$) δ1.50–1.70 (m, 2H), 2.30, 2.34 (ds, 1.5H), 2.42–2.70 (m, 6H), 3.04 (s, 2H), 3.52–3.85 (m, 14H), 3.90, 3.92 (ds, 1.5H), 5.38–5.68 (bs, 2H), 6.85–8.32 (m, 15-1/6H). Mass spectrum (electrospray), m/z 566–770 (M+1)$^+$.

EXAMPLE 38

Preparation of Library 30 (FIG. 6)

Library 30 was synthesized as above for Library 25 using Library 20 (61 mg, 0.1 mmol), α-bromoacetamide (18.0 mg, 0.129 mmol, 1.29 eq) and K$_2$CO$_3$ (0.20 g, 1.4 mmol) in 5 mL of acetonitrile. The mixture was stirred at 50–60° C. for 24 hours. The work-up procedure was the same as above for Library 25. The preparative TLC was developed by 2:1 ethyl acetate-methanol. 42 mg (59%) of Library 30 was obtained as a pale yellow oil.

TLC: Rf: 0.15–0.46; ethyl acetate-methanol, 2:1, v/v; silica gel. $^1$H NMR (CDCl$_3$) δ1.50–1.76 (m, 2H), 2.30, 2.34 (ds, 1.5H), 2.55–2.82 (m, 6H), 3.09 (s, 3H), 3.37 (s, 5 2H), 3.48–3.80 (m, 17H), 3.90, 3.92 (ds, 1.SH), 6.85–8.32 (m, 15-1/6H). Mass spectrum (electrospray), m/z 610–814 (M+1)$^+$.

EXAMPLE 39

Preparation of Library 27 (FIG. 6)

Methyl α-bromoacetate (12 μL, 18.8 mg, 0.122 mmol, 1.22 eq) was added to a stirred mixture of Library 20 (61

Mg, 0.1 mmol) and $K_2CO_3$ (0.2 g, 1.4 mmol) in 85 mL of acetonitrile. The resulting reaction mixture was stirred at room temperature overnight. The solvent was evaporated and the residue was dissolved in water-chloroform. The organic layer was separated and the aqueous layer was extracted with chloroform. The combined chloroform extracts were washed with brine and dried ($Na_2S_4$). The solvent was evaporated and the residue was purified by preparative thin lager chromatography (TLC) on silica gel using 20:1 ethyl acetate-methanol as the developing agent. 45 mg (65%) of Library 27 was obtained as a pale yellow oil.

TLC: Rf: 0.39–0.56; ethyl acetate-methanol, 20:1, v/v; silica gel. $^1$H NMR ($CDCl_3$) d 1.50–1.68 (m, 2H), 2.31, 2.34 (ds, 1.5N), 2.56–2.80 (m, 6H), 3.25 (s, 2H), 3.52–3.80 (m, 17H), 3.90, 3.92 (ds, 1.5H), 6.85–8.30 (m, 15-1/6H).

Mass spectrum (eletrospray), m/z 581–785 (M+1)$^+$.

EXAMPLE 40

N-Trifluoroacetyl-3-amino-1-O-dimethoxytritylpropanol

3-Amino-1-propanol (Aldrich, 1 g, 13.31 mmol) was dissolved in $CH_2Cl_2$ (40 ml) and 1 equivalent of ethyltrifluoroacetate (1.58 mL, 13.31 mmol) was added at room temperature. The reaction was complete in 2 hours as indicated by TLC. The reaction mixture was concentrated in vacuo and the resulting residue was coevaporated with pyridine (3×25 ml). The clear oil was re-dissolved in pyridine (50 ml) and one equivalent of triethylamine (1.87 ml, 13.31 mmol) was added. Dimethoxytritylchloride (4.51 g, 13.31 mmol) was added in four equal portions. The reaction was complete in 20 hours as indicated by TLC. The reaction mixture was partitioned between $CH_2Cl_2$ and water. The $CH_2Cl_2$ layer was separated, dried ($MgSO_4$), filtered and concentrated in vacuo. The resulting residue was purified by silica gel flash column chromatography using a gradient of 5% to 10% EtOAc in hexanes with 1% triethyl amine as the eluent. The appropriate fractions were pooled and concentrated in vacuo to give 5.29 g (84%) of the title compound. $^1$H NMR (DMSO) δ1.79 (m, 2H, $CH_2$), 3.01 (t, 2H, $CH_2$), 3.32 (t, 2H, $CH_2$), 3.75 20 (s, 6H, 2x $OCH_3$), 6.88 (d, 4H, DMT), 7.23–7.40 (m, 9H, DMT), 9.36 (bs, 1H, NH). $^{19}$F NMR (DMSO) δ–75.72 (s, $CF_3$), ($^{19}$F peaks referenced to trifluoroacetic acid).

EXAMPLE 41

N-Acetylmethyl-N-trifluoroacetyl-3-amino-1-O-dimethoxytritylpropanol

N-(Trifluoroacetyl)-3-amino-1-O-dimethoxytritylpropanol (40 g, 84.50 mmol) was dissolved in DMF (600 ml) and cooled in an ice bath to 0° C. NaH (60% dispersion, 4 g, 1.2 eq., 101.40 mmol) was added in 4 equal portions and the reaction mixture was allowed to stir for 2 hours at 0° C. before methylbromoacetate (10.31 mL, 92.95 mmol) was added dropwise. The reaction was slowly warmed up to room temperature overnight. The reaction was complete in 20 hours as indicated by TLC. The reaction mixture was concentrated in vacuo to approximately 100 ml. The reaction mixture was then partitioned between $H_2O$ and $CH_2Cl_2$ (100 ml 1:1). The $CH_2Cl_2$ layer was dried ($MgSO_4$) and concentrated in vacuo. The resulting residue was purified by silica gel column flash chromatography using a gradient of 50 to 10% EtOAc in hexanes with 1% triethyl amine as the eluent. The appropriate fractions were pooled and concentrated in vacuo to give the title compound 35.90 g (83%). $^1$H NMR ($CDCl_3$) δ1.89 (m, 2H, $CH_2$), 3.12 (dd, 2H, $CH_2$), 3.61 (dd, 2H, $CH_2$), 3.70 (x, 6H, 2x $OCH_3$), 3.76 (d, 3H, $CH_3$), 4.08 (s, 2H, $CH_2$), 6.82–7.43 (m, 13H, DMT). $^{19}$F NMR ($CDCl_3$) δ–75.57 S, ($CF_3$), –75.15 (s, $CF_3$), (peaks referenced to trifluoroacetic acid). $^{13}$C NMR ($CDCl_3$) spectra is consistent with structure.

EXAMPLE 42

N-(2-Hydroxyethyl)-3-amino-1-o-dimethoxytritylpropanol N-Acetylmethyl-3-amino-1-O-dimethoxytritylpropanol (4.40 g, 8.62 mmol) was dissolved in a minimal amount of $CH_2Cl_2$ (75 ml) and MeOH (200 ml) was added. $NaBH_4$ (1.30 g, 34.48 mmol) was added in four equal portions. The reaction mixture was stirred at room temperature for 18 hours. After 18 hours the reaction had gone to completion as indicated by TLC. The reaction mixture was concentrated in vacuo to leave a white waxy solid which was partitioned between $H_2O$ and EtOAc (100 mL, 1:1). The $H_2O$ layer was extracted with EtOAc (3×50 ml). The EtOAc extracts were collected and dried ($MgSO_4$), filtered and concentrated in vacuo. The resulting residue was purified by silica gel flash column chromatography using a gradient of 5% to 10% MeOH in $CH_2Cl_2$ with 1% triethyl amine. The appropriate fractions were pooled and concentrated in vacuo to give the title compound 1.42 g (42%).

EXAMPLE 43

N-(2-Hydroxyethyl)-3-amino-1-propanol

N-(2-hydroxyethyl)-3-amino-1-O-dimethyoxytritylpropanol (5 g, 11.86 mmol) is dissolved in 80% AcOH (100 mL). The reaction is stirred until complete, as indicated by TLC. The reaction mixture is concentrated in vacuo. The resulting residue is purified by silica gel flash column chromatography using MeOH/$CH_2Cl_2$ as the eluent. The appropriate fractions are pooled and concentrated in vacuo to give the title compound.

EXAMPLE 44

N-(2-Hydroxyethyl)-N-tritylsulfenyl-3-amino-1-propanol

N-(2-hydroxyethyl)-3-amino-1-propanol (5.0 g, 41.9 mmol) is coevaporated several times with pyridine (20 mL) and then dissolved in pyridine (100 mL). The reaction flask is flushed with Argon and trimethylsilylchloride (2.47 g, 209.5 mmol) is added dropwise. The reaction mixture is stirred for 1 hour. Triphenyl methanesulfenyl chloride (14.32 g, 46.09 mmol) is dissolved in $CH_2Cl_2$ and added via dropping funnel to the cooled reaction mixture. The reaction mixture is warmed to room temperature and stirred for 18 hours. The reaction mixture is concentrated in vacuo and the resultant residue is partitioned between $H_2O$ and EtOAc (100 ml, 1:1). The $H_2O$ layer is separated and extracted with EtOAc (3×50 ml). The EtOAc extracts are pooled, dried ($MgSO_4$) and filtered. The filtrate is concentrated in vacuo and the residue is purified by silica gel flash column chromatography with EtOAc/hexanes as the eluent. The appropriate fractions are pooled and concentrated in vacuo to give the title compound.

EXAMPLE 45

N-(2-p-Toluenesulfonylethyl)-N-tritylsulfenyl-3-amino-1-O-p-toluenesulfonylpropanol N-(2-hydroxyethyl)-N-tritylsulfenyl-3-amino-1-propanol (5.0 g, 12.64 mmol) is dissolved in pyridine (100 mL) and cooled to 0° C. p-Toluensufonylchloride (2.65 g, 13.9 mmol) is dissolve in CH$_2$Cl$_2$ (50 mL) and added to the reaction mixture at 0° C. via dropping funnel. The reaction is monitored by TLC to completion. The reaction mixture is concentrated in vacuo and the resultant residue is dissolved in EtOAc and washed with H$_2$O (3×50 mL) and brine (2×50 mL). The EtOAc is dried (MgSO$_4$), filtered and concentrated in vacuo. The residue is purified by silica gel column chromatography using EtOAc/hexanes as eluent. The appropriate fractions are pooled and concentrated in vacuo to give the title compound.

EXAMPLE 46

N-(2-O-p-Toluensulfonylethyl)-N-tritylouIfenyl-3-amino-1-O-phthalimidopropanol, N-(2-O-phthalimidoethyl)-N-tritylsulfenyl-3-amino-1-p-toluenesulfonylpropanol N-(2-O-p-toluenesulfonylethyl)-N-tritylsulfenyl-3-amino-1-p-toluenesulfonylpropanol (5.0 g, 7.12 mmol), triphenylphosphine (2.05 g, 7.83 mmol) and N-hydroxyphthalimide (1.74 g, 10.68 mmol) are dissolved in dry THF under an atmosphere of argon. The reaction mixture is cooled to 0° C. and diisopropyl azodicarboxylate (1.89 g, 8.54 mmol) is added dropwise (slowly so the orange color created by the diisopropyl azodicarboxylate dissipates before the next addition). The reaction mixture is warmed up to room temperature and stirred for 18 hours. The reaction mixture is concentrated in vacuo and the residue partitioned between EtOAc and H$_2$O (100 mL, 1:1). The H$_2$O layer is separated and extracted with EtOAc (3×50 mL). The EtOAc extracts are dried (MgSO$_4$), filtered and concentrated in vacuo. The resultant residue is purified by silica gel flash column chromatography using EtOAc/hexanes as the eluent. The appropriate fractions are pooled and concentrated in vacuo. The residue is treated as per the procedure of Example 45 with p-toluene sulfonyl chloride to give both of the title compounds.

EXAMPLE 47

N-(2-O-Phthalimidoethyl)-N-tritylaulfenyl-3-amino-1-azidopropane

N-(2-O-phthalimidoethyl)-N-tritylsulfenyl-3-amino-1-p-toluenesulfonylpropanol (5.0 g, 9.51 mmol) is dissolved in dry DMF (100 mL). NaN$_3$ (0.74 g, 11.41 mmol) is added to the reaction mixture. The reaction mixture is warmed up to 40° C. The reaction progress is monitored by TLC. The reaction mixture is concentrated in vacuo and the residue partitioned between EtOAc and H$_2$O (100 mL, 1:1). The H$_2$O layer is separated and extracted with EtOAc (3×50 mL). The EtOAc extracts are dried (MgSO$_4$), filtered and concentrated in vacuo. The resultant residue is purified by silica gel flash column chromatography using EtOAc/hexanes as the eluent. The appropriate fractions are pooled and concentrated in vacuo to give the title compound.

EXAMPLE 48

N-(2-O-aminoethyl)-N-trityleulfenyl-1,3-diaminopropane

N-(2-O-phthalimidoethyl)-N-tritylsulfenyl-3-amino-1-azidopropane (5.0 g, 9.03 mmol) is dissolved in THF (100 mL) and a catalytic amount of H$_2$O is added to the reaction mixture. Triphenylphosphine (2.61 g, 9.93 mmol) is added at room temperature and the reaction mixture is allowed to stir. Reaction progress is monitored by TLC. The reaction mixture is concentrated in vacuo and the residue partitioned between EtOAc and H$_2$O (100 ml, 1:1). The H$_2$O layer is separated and extracted with EtOAc (3×50 mL). The EtOAc extracts are dried (MgSO$_4$), filtered and concentrated in vacuo. The residue is dissolved in CH$_2$Cl$_2$ (100 mL) and cooled to 0° C. Methylhydrazine (0.46 g, 9.93 mmol) is added to the reaction mixture drop wise. The reaction mixture is stirred until complete by TLC. The reaction mixture is concentrated in vacuo and the residue partitioned between EtOAc and H$_2$O (100 mL, 1:1). The H$_2$O layer is separated and extracted with EtOAc (3×50 mL). The EtOAc extracts are dried (MgSO$_4$), filtered and concentrated in vacuo. The resultant residue is purified by silica gel column chromatography using MeOH/CH$_2$Cl$_2$ as the eluent. The appropriate fractions are pooled and concentrated in vacuo to give the title compound.

EXAMPLE 49

Diethyl-4-bromo-2,6-pyridinedicarboxylate

To chelidamic acid (2.29 g, 11.38 mmol) was added phosphorus pentabromide (14.7 g, 34.14 mmol), and the mixture was stirred. The reaction mixture was heated to 90° C. for 3 hours. The reaction mixture was cooled and CHCl$_3$ (350 mL) was added and the mixture was filtered. To the filtrate was added absolute ethanol (350 mL), and the mixture was stirred for 2 hours. The volume of the reaction mixture was reduced to approximately 35 mL. The title compound was purified by crystallization upon sitting overnight to give, after a second crop of crystals and purification by silica gel flash column chromatography a yield of 72% (m. p. 95–96° C). $^1$H NMR (CDCl$_3$) δ1.49 (t, 6H, 2x CH$_3$), 4.44 (q, 4H, 2x CH$_2$), 8.39 (s, 2H, 2x Ar). $^{13}$C NMR (CDCL$_3$) δ14.19 (CH$_3$), 62.68 (CH$_2$), 131.02 (Ar), 134.87 (quaternary-Ar), 149.54 (quaternary-Ar), 163.51 (CO).

EXAMPLE 50

Diethyl-4-(3-azidopropoxy)-2,6-pyridinedicarboxylate

3-Azido-1-propanol (0.266 mL, 3.64 mmol) was dissolved in DMF (5 mL) and cooled to 0° C. NaH (146 mg, 3.64 mmol) was added and the mixture was stirred for 15 minutes. Diethyl-4-bromo-2,6-pyridinedicarboxylate was dissolved in DMF (5 mL) an added to the reaction mixture dropwise. The reaction was complete as indicated by TLC in 1 hour. The reaction mixture was partitioned between CH$_2$Cl$_2$ and water. The water was separated and extracted with CH$_2$Cl$_2$. The CH$_2$Cl$_2$ layers were combined, dried (MgSO4) and concentrated to an oil. The oil was purified by silica gel flash column chromatography to give a yield of 40% $^1$H NMR (CDCl$_3$) δ1.44 (t, 6H, 2x CH$_2$), 2.11 (m, 2H, CH$_2$), 3.54 (t, 2H, CH$_2$), 4.23 (t, 2H, CH$_2$), 4.45 (q, 4H, 2x CH$_2$), 7.78 (2, H, 2x Ar)

EXAMPLE 51

4-(3-Azidopropoxy)-2,6-dihydroxymethylpyridine

To a stirred solution of Diethyl-4-(3-azidopropoxy)-2,6-pyridinedicarboxylate (4.2 mmol) in dichloromethane (10 mL) and absolute ethanol (15 mL), was added in portions, NaBH$_4$ (4.2 mmol) at 25° C. Powdered CaCl2 (4.2 mmol) was added cautiously in small portions and the evolution of hydrogen was allowed to cease before each further addition. The reaction mixture was stirred for 2 hours. Water (100 mL) was added and the reaction mixture was extracted several times with ethyl acetate. The ethyl acetate layers were combined, dried (MgSO$_4$) and concentrated in vacuo. The resultant residue was purified by silica gel flash column chromatography to give the title compound. $^1$H NMR (DMSO) δ2.00 (m, 2H, CH$_2$), 3.52 (t, 2H, CH$_2$), 4.13 (t, 2H, CH$_2$), 4.45 (d, 4H, 2x CH$_2$), 5.36 (t, 2H, 2x OH), 6.87 (s, 2H, 2x AR).

EXAMPLE 52

4-(Azidopropoxy)-2,6-diforml-pyridine

DMSO (1.21 mL, 17.1 mmol) was diluted with CH$_2$Cl$_2$ (approximately 25 mL) and cooled to −78° C. Oxalyl chloride (0.745 mL, 8.45 mmol) was added dropwise and the reaction mixture was stirred for 15 minutes. 4-(3-azidopropoxy)-2,6-dihydroxymethylpyridine (1 g, 4.27 mmol) dissolved in CH$_2$Cl$_2$ (10 mL) was added slowly to the cooled reaction mixture. After 0.5 hour triethylamine (2.77 mL, 19.70 mmol) was added dropwise to the reaction mixture. The dry ice/acetone bath was removed and the reaction mixture was warmed to room temperature for approximately 40 minutes. The reaction mixture was partitioned between CH$_2$CH$_2$ and water and extracted several times with CH$_2$Cl$_2$. The CH$_2$Cl$_2$ layers were combined, dried (MgSO$_4$) and concentrated in vacuo. The resulting residue was purified by silica gel flash column chromatography to give the title compound.

$^1$H NMR (DMSO) δ2.02 (m, 2H, CH$_2$), 3.52 (t, 2H, CH$_2$), 4.31 (t, 2H,CH$_2$), 7.64 (s, 2H, 2x Ar), 10.01 (s ,2H, CHO). $^{13}$C NMR (DMSO) δ27.61 (CH$_2$), 47.40 (CH$_2$), 66.22 (CH$_2$), 111.58 (Ar), 154.40 (quaternary, Ar), 166,50 (quaternary, Ar), 192.44 (CHO).

EXAMPLE 53

2-(Aminamethyl)-4-azidoprpxy-6-[(N1-methyl-1-yl)-N2[(tritylsulfenyl)-1-ethanol-2-yl]-1,2-diaminopropane]-pyridine The title compound is prepared following the procedure of Example 20 using 4-(azidopropoxy)-2,6-diformyl-pyridine (Example 52) and N-(2-O-aminoethyl)-N-tritylsulfenyl-1, 3-diaminopropane (Example 48).

EXAMPLE 54

2,4,6-Triethoxycarbonyl-1,3,5-triazine

Hydrogen chloride gas was bubbled through neat ethyl-cyanoformate (0.997 ml, 10.1 mmol) until the solution became a white solid, approximately 2 hours. The solid was partitioned between CH$_2$Cl$_2$ and water. The CH$_2$Cl$_2$ layer was collected dried (MgSo$_4$) and concentrated to a white solid. The product was recrystallized from hot absolute ethanol to give the title compound (m. p. 169–170° C.). $^1$H NMR (CDCl$_3$) δ1.42 (t, 9H, 3x CH$_3$), 4.50 (q, 6H, 3x CH$_2$). $^{13}$C NMR (DMSO) δ14.06 (CH$_3$), 64.02 (CH$_2$), 161.27 (CO), 166.86 (Triazine Ar).

EXAMPLE 55

2,4,6-Trihydroxymethyl-s-triazine 2,4,6-Triethoxycarbonyl-s-triazine (1 g, 3.36 mmol) is dissolved in dichloromethane (15 mL) and absolute ethanol (25 mL) then cooled to 0° C. before sodium borohydride (127 mg, 3.36 mmol) is added. After 15 minutes calcium chloride (373 mg, 2.97 mmol) is added and the reaction mixture is warmed to room temperature. The reaction mixture is dried to a yellow solid and subjected to soxhlet extraction with ethanol. The ethanol is evaporated to a white solid. The product is crystallized from Methanol and water or purified by silica gel flash column chromatography to give the title compound.

EXAMPLE 56

4-(p-Toluensaulfonylmethyl)-2,6-dihydroxymethyl-s-triazine 2,4,6-Trihydroxymethyl-s-triazine (1 eq.) is dissolved in an excess of pyridine. p-Toluenesulfonylchloride (0.9 eq.) in CH$_2$Cl$_2$ is added and the reaction mixture is stirred overnight. The solvent volume is reduced to a slurry to which water and dichloromethane are added and the resulting mixture is extracted with CH$_2$Cl$_2$. The combined CH$_2$Cl$_2$ layers are dried (MgSO$_4$) and concentrated to an oil. The oil is purified by silica gel flash column chromatography to give the title compound.

EXAMPLE 57

4-(Azidamethyl)-2,6-dialdehyde-s-triazine (via 4-(azidomethyl)-2,6-dihydroxymethyl-S-triazine)

4-(p-Toluenesulfonylmethyl)-2,6-dihydroxymethyl-s-triazine is dissolved in DMF and sodium azide (1.1 eq.) is added. The reaction mixture is heated to 50° C. for 4 hours. The DMF is removed under reduced pressure and the residue is partitioned between CH$_2$Cl$_2$ and water. The CH$_2$Cl$_2$ layer is separated and the water layer is extracted several times with CH$_2$Cl$_2$. The CH$_2$Cl$_2$ layers are combined, dried (MgSO$_4$), and concentrated. The resultant residue is purified by silica gel flash column chromatography to give 4-(azidomethyl)-2,6-dihydroxymethyl-s-triazine.

DMSO is diluted with CH$_2$Cl$_2$ and cooled to −78° C. oxalyl chloride is added slowly and allowed to stir for 0.5 hours. The 4-(azidomethyl)-2,6-dihydroxymethyl-s-triazine dissolved in CH$_2$Cl$_2$ is added slowly to the reaction mixture. After 1 hour, triethylamine is added dropwise and the reaction is allowed to warm up to room temperature. The reaction mixture is diluted with water and CH$_2$Cl$_2$. The CH$_2$Cl$_2$ layer is separated and the water layer is extracted several times with CH$_2$Cl$_2$. The CH$_2$Cl$_2$ layers are combined, dried (MgSO4), and concentrated. The resultant oil is purified by silica gel flash column chromatography to give the title compound.

EXAMPLE 58

2-(Aninomethyl)-4-(azidamethyl)-6-[N1-methylene-N2-[(tosyl)-1-propanol-3-yl]-1,2-diaminoethane]-s-triazine The title compound is prepared following the procedure of Example 20 using N1-[(tosyl)-O-aminopropanol-3-yl] diaminoethane (Example 19) and 4-(azidomethyl)-2,6-dialdehyde-s-triazine (Example 57).

EXAMPLE 59

2-(N,N-dibenzylaminomethylene)-6-{[N1-[benzyl (methyl-1-yl)]-N2-(benzyl)-1-propanol-3-yl]-1,2-diaminoethane}pyridine 9 (FIG. 4)

A mixture of 2-aminomethylene-6-{[N1-(methyl-1-yl)-N2-1-propanol-3-yl]-1,2-diaminoethane}pyridine 7 (FIG. 2)

(37 mg, 0.155 mmol), $K_2CO_3$ (0.20 g, 1.4 mmol) and benzyl bromide (78 µL, 112 mg, 0.66 mmol, 4.25 eq) in 5 mL of acetonitrile and 2 mL of DMF was stirred at room temperature overnight. The solvent was evaporated under vacuum and the residue was dissolved in water and chloroform. The layers were separated and the aqueous layer was extracted with chloroform. The combined chloroform extracts were washed with brine and dried ($Na_2SO_4$). The solvent was evaporated and the residue was purified by preparative thin layer chromatography (preparative-TLC) on a silica gel plate using ethyl acetate-methanol (15:1, v/v) as the developing agent. 46 mg (51%) of the title compound was obtained as a pale yellow oil.

TLC: Rf: 0.43; ethyl acetate-methanol, 20:1, v/v; silica gel. $^1$H NMR ($CDCl_3$) δ1.56–1.75 (m, 2H), 2.50–2.75 (m, 6H), 3.45–3.85 (m, 14H), 7.12–7.70 (m, 23H). Mass spectrum (HRFAB), m/z 599.377 $(M+1)^+$ ($C_{40}H_{47}N_4O$ requires 599.375).

EXAMPLE 60

2-(N-t-Butyldiphenylsilyl)aminomethylene-6-{[N1-(methyl-1yl)-N2-(t-Boc)1-propanol-3-yl]-1,2-diaminoethane}pyridine 2-Aminomethylene-6-{[N1-(methyl-1yl)-N2-(t-Boc)1-propanol-3-yl]1,2-diaminoethane}pyridine 5 (FIG. 2) is dissolved in dichloromethane and treated with t-butylchlorodiphenylsilane (Aldrich) to give the title compound.

EXAMPLE 61

2-(N-t-Butyldiphenylsilyl)aminomethylene-6-{[N1-(benzyl)-(methyl-1yl)-N2-(t-Boc)1-propanol-3-yl]-1,2-diaminoethane}-pyridine 2-(N-t-Butyldiphenylsilyl)aminomethylene-6-{[N1-(benzyl)(methyl-1yl)-N2-(t-Boc)1-propanol-3-yl]-1,2-diaminoethane}pyridine is treated with benzylbromide as per the procedures of Examples 27–39 to give the title compound.

EXAMPLE 62

2-Aminomethylene-6-{(N1-(benzyl)(methyl-1yl)-N2-(t-Boc) 1-propanol-3-yl]-1,2-diaminoethane}pyridine 2-(N-t-Butyldiphenylsilyl)aminomethylene-6-{[N1-(benzyl)(methyl-1yl)-N2-(t-Boc)1-propanol-3-yl]-1,2-diaminoethane}pyridine is treated with an aqueous solution of acetic acid (60%, v/v) at 25° C. for 30 minutes to give the title compound.

EXAMPLE 63

2-(N-o-nitrophenylsulfonyl)aminomethylene-6-{[N1-(benzyl)(methyl-1yl)-N2-(t-Boc)1-propanol-3-yl]-1,2-diaminoethane}pyridine A solution of 2-nitrobenzenesulfonyl chloride (Aldrich, 5.32 g, 24 mmol, 2.4 eq) in dichloromethane (30 mL) is added dropwise to a stirred solution of 2-aminomethylene-6-{[N1-(benzyl)(methyl-1yl)-N2-(t-Boc)(benzyl)1-propanol-3-yl]-1,2-diaminoethane}pyridine (20 mmol) and triethylamine (16 mL) in dichloromethane (60 mL) at 0° C. The resulting reaction mixture is allowed to warm to room temperature and further stirred for 1 hour. The mixture is diluted with chloroform and washed with water and brine. The organic phase is dried ($Na_2SO_4$) and the solvent is evaporated under reduced pressure. The residue is purified by flash chromatography on a silica gel column (20 cm×3 cm) to give the title compound.

EXAMPLE 64

2-[N-(-methoxycarbonylbenzyl)(o-nitrophenylsulfonyl)-aminomethylene]-6-{[N1-(benzyl)(methyl-1yl)-N2-(t-Boc)1-propanol-3-yl]-1,2-diaminoethane}pyridine 2-(N-o-nitrophenylsulfonyl)aminomethylene-6-{[N1-(benzyl)(methyl-1yl)-N2-(t-Boc)1-propanol-3-yl]-1,2-diamino-ethane}pyridine is treated with methyl-m-bromomethylbenzoate as per the procedures of Examples 27–39 to give the title compound.

EXAMPLE 65

2-N(m-methoxycarbonylbenzyl)3aminomethylene-6-{[N1-(benzyl)-(methyl-1yl)-N2-(t-Boc)1-propanol-3-yl]-1,2-diaminoethane}-pyridine 2-[N(m-methoxycarbonylbenzyl)(N-o-nitrophenylsulfonyl)aminomethylene]-6-{[N1-(benzyl)(methyl-1yl)-N2-(t-Boc)1-propanol-3-yl]-1,2-diaminoethane}pyridine is dissolved in DMF and treated with thiophenol in the presence of $K_2CO_3$ to give the title compound.

EXAMPLE 66

2-N(m-methoxycarbonylbenzyl)(m-xylyl) aminomethylene-6-{[N1-(benzyl)(methyl-1yl)-N2-(t-Boc)-1-propanol-3-yl]-1,2-diaminoethane}pyridine 2-N(m-methoxycarbonylbenzyl)aminomethylene-6-{(N1-(methyl-1yl)-N2-(t-Boc)(benzyl)1-propanol-3-yl]-1,2-diaminoethane}pyridine is treated with α-bromomethylxylyl as per the procedures of Examples 27–39 to give the title compound.

EXAMPLE 67

2-N(m-methoxycarbonylbenzyl)(m-xylyl) aminomethylene-6-{[N1-(benzyl)(methyl-1yl)-N2–1-propanol-3-yl]-1,2-diaminoethane}pyridine 2-N-(m-methoxycarbonylbenzyl)(m-xylyl) aminomethylene-6-{(N1-(benzyl)(methyl-1yl)-N2-(t-Boc)-1-propanol-3-yl)-1,2-diaminoethane}pyridine (0.56 mmol) in dichloromethane (2.0 mL) at 0° C. is treated as per the procedure of Example 8 to give the title compound.

EXAMPLE 68

2-N-(m-methoxyearbonylbenzyl)(m-xylyl) aminomethylene-6-{[N1-(benzyl)(methyl-1yl)-N2(2-fluorobenzyl)-1-propanol-3-yl]-1,2-diaminoethane}pyridine 2-N-(m-methoxycarbonylbenzyl)(m-xylyl) aminomethylene-6-{[N1-(benzyl)(methyl-1yl}-N2–1-propanol-3-yl]-1,2-diaminoethanelpyridine is treated with 3-fluorobenzylbromide as per the procedures of Examples 27–39 to give the title compound.

EXAMPLE 69

Diethyl-4-piperazinyl-2,6-pyridinedicarboxylate

A mixture of diethyl 4-bromopyridine-2,6-dicarboxylate (Example 49) (3.02 g, 10.0 mmol) and piperazine (Aldrich, 4.3 g, 50 mmol) in dioxane (200 mL) was refluxed for 24 hours. The precipitate was filtered off and the filtrate was concentrated under vacuum. The residue was dissolved in ethyl acetate and washed four times with brine. The organic solution was dried ($Na_2SO_4$) and the solvent was evaporated. The residue was purified by flash chromatography on a silica gel column (22 cm×3 cm). Elution with methanol and then methanol:30% ammonium hydroxide (100:1, 50:1, and 20:1, v/v) gave 3.05 g (99%) of the title compound as a pale yellow foam.

TLC: Rf 0.35; methanol:30% ammonium hydroxide; 100:1, v/v; silica gel. $^1H$ NMR ($CDCl_3$) δ1.45 (t, 6H, J=7.2 Hz), 1.73 (bs, 1H), 2.95–3.06 (m, 4H), 3.38–3.50 (m, 4H), 4.44 (q, 4H, J=7.2 Hz), 7.63 (s, 2H). $^{13}C$ NMR ($CDCl_3$) δ14.18, 45.53, 46.96, 62.16, 111.34, 149.25, 156.37, 165.62. Mass spectrum (HRFAB), m/z 308.162, $(m+1)^+$ ($C_{15}H_{22}O_4N_3$ requires 308.161).

EXAMPLE 70

4-Piperazinyl-2,6-bis-hydroxymethyl pyridine

Diethyl-4-piperazinyl-2,6-pyridinedicarboxylate is dissolved in THF and treated with NaBH, and $CaCl_2$ as per the procedure of Example 51 to give the title compound.

EXAMPLE 71

4-piperazinyl-2,6-bis-aldehyde pyridine 4-piperazinyl-2,6-bis-hydroxymethyl pyridine and triethylamine are dissolved in THF and the resulting solution is treated with $CrO_3$. The reaction mixture purified by silica gel flash column chromatography to give the title compound.

EXAMPLE 72

4-(N4-CBZ-piperazine-1-yl)-2,6-bis-aldehyde pyridine

4-Piperazinyl-2,6-bis-aldehyde pyridine and triethyl amine are dissolved in chloroform and treated with an excess of benzyl chloroformate. The reaction mixture is washed with water and brine. The organic phase is dried ($Na_2SO_4$) and the solvent is evaporated. The residue is purified by silica gel flash column chromatography to give the title compound.

EXAMPLE 73

2-Aminomethylene-4-(N4-CBZ-piperazine-1-yl)-6-{[N1-(methyl-1-yl)-N2-(t-Boc)1-propanol-3-yl]-1,2-diaminoethane}pyridine 4-(N4-CBZ-piperazine-1-yl)-2,6-bis-aldehyde pyridine and Nit(t-Boc)-3-(O-amino)propanol-1-ylldiaminoethane 1 (FIG. 2) are treated as per the procedures of Example 7 to give the title compound.

EXAMPLE 74

2-Aminomethylene-4-(N4-CBZ-piperazine-1-yl)-6-{[N1-(methyl-1-yl)-N2-1-propanol-3-yl]-1,2-diaminoethane}pyridine 2-Aminomethylene-4-(N4-CBZ-piperazine-1-yl)-6-([N1-(methyl-1yl)-N2-(t-Boc)1-propanol-3-yl]-1,2-diaminoethane)pyridine is deprotected (t-Boc) as per the procedure of Example 8 to give the title compound.

EXAMPLE 75

Preparation of Library 31

2-N-Bis-($L_8$–$L_{12}$)-Aminomethylene-4-(N4-CBZ-piperazine-1-yl)-6-{[N1-($L_8$–$L_{12}$)(methyl-1yl)-N2-($L_8$–$L_{12}$)1-propanol-3-yl]-1,2-diaminoethane}pyridine 2-Aminomethylene-4-(N4-CBZ-piperazine-1-yl)-6-{[N1-(methyl-1yl)-N2-1-propanol-3-yl]-1,2-diaminoethane}-pyridine is treated with an equimolar mixture of m-nitrobenzylbromide ($L_8$—Br), m-trifluoromethylbenzylbromide ($L_9$—Br), methyl-α-bromo-methylacetate ($L_{10}$—Br), α-bromoacetonitrile ($L_{11}$—Br), α-bromo-acetamide ($L_{12}$—Br). The crude material is purified as per the procedure of Example 23 to give the title library.

EXAMPLE 76

Deprotection of Library 31, preparation of Library 32

2-N-Bis-($L_8$–$L_{12}$)-Aminomethylene-4-(piperazine-1-yl)-6-{[N1-($L_8$–$L_{12}$)(methyl-1yl)-N2-($L_8$–$L_{12}$)1-propanol-3-yl -1,2-diaminoethane}pyridine Hydrogen bromide in acetic acid (40%) is added to a flask containing (2.1 mmol) of Library 31 at 0° C. The resulting solution is stirred at room temperature for 3 hours. The reaction mixture is diluted with water and neutralized with aqueous sodium carbonate and then extracted with chloroform. The organic extract is dried ($Na_2SO_4$), the solvent is evaporated and the resulting residue is purified by flash chromatography on a silica gel column Elution with 100% methanol and then 100:1 methanol-30aqueous ammonium hydroxide will afford the deprotected library 32.

EXAMPLE 77

Preparation of Library 33

2-N-Bis-($L_8$–$L_{12}$)-Aminomethylene-4-(N4-($L_8$–$L_{12}$)-piperazine-1-yl)-6-{[N1-($L_8$–$L_{12}$)(methyl-1yl)-N2-($L_8$–$L_{12}$)1-propanol-3-yl]-1,2-diaminoethane}pyridine 2-N-Bis-($L_8$–$L_{12}$)-Aminomethylene-4-(piperazine-1 -yl)-6-{[N1-($L_8$–$L_{12}$)(methyl-1yl)-N2-($L_8$–$L_{12}$)1-propanol-3-yl]-1,2-diaminoethane}pyridine is treated as per the procedure of Example 75 to give Library 33.

EXAMPLE 78

2-N—($L_8$)($L_9$)-Aminamethylene-4-(N4-($L_{10}$)-piperazine-1-yl)-6-{[N1-($L_{11}$)(methyl-1yl)-N2-($L2_2$) 1-propanol-3-yl]-1,2-diaminoethane}pyridine Starting with 2-aminomethylene-4-(N4-CBZ-piperazine-1-yl)-6-{[N1-(methyl-1yl)-N2-(t-Boc)1-propanol-3-yl]-1,2-diaminoethane}pyridine, m-nitrobenzylbromide ($L_8$—Br), m-trifluoromethylbenzylbromide ($L_9$—Br), methyl-α-bromo-methylacetate ($L_{10}$—Br), α-bromoacetonitrile ($L_{11}$—Br), α-bromo-acetamide ($L_{12}$—Br), and following the procedures of examples 60–68 and 76–77, the deconvoluted title compound is prepared.

EXAMPLE 79

N-m-Nitrobenzyl-3-amino-1-propanol

To a solution of m-nitrobenzaldehyde (94.23 mmol) and trimethylorthoformate (15.5 mL, 141 mmol) in MeOH (300 mL) is added dropwise 3-amino-1-propanol (7.21 mL, 94.23 mmol) at room temperature. The reaction is allowed to stir at room temperature for 5 hours followed by cooling to 0° C. in an ice bath. Sodium borohydride (3.56 g, 94.23 mmol) is added in two portions and when the bubbling stops the solvent is evaporated. The resulting residue is partitioned between ethyl acetate (75 mL) and water (75 mL). The aqueous layer is extracted twice with ethyl acetate (75 mL). The ethyl acetate extracts are collected and washed twice with Brine (50 mL), dried over $MgSO_4$, filtered, and concentrated. Drying will give the title compound.

EXAMPLE 80

Diethyl-4-(N-m-nitrobenzyl)3-aminopropoxy-2,6-pyridinedicarboxylate

Diethyl-4-bromo-2,6-pyridinedicarboxylate is treated with N-benzyl-3-amino-1-propanol as per the procedure of Example 50 to give the title compound.

EXAMPLE 81

Diethyl-4-(N—$L_n$)3-aminopropoxy-2,6-pyridinedicarboxylate

Following the procedures of Examples 79 and 80 and using one of m-methyl benzaldehyde, cinnamaldehyde, m-cyanobenzaldehyde, m-bromobenzaldehyde, or m-chlorobenzaldehyde the other 5 analogs of diethyl-4-(N-m-nitrobenzyl)3-aminopropoxy-2,6-pyridinedicarboxylate are prepared. Each of the 6 compounds diethyl-4-(N—$L_n$) 3-aminopropoxy-2,6-pyridinedicarboxylate have a different letter ($L_n$) attached to the amino group e.g. m-nitrobenzyl (Example 80), m-methylbenzyl, cinnamyl, m-cyanobenzyl, m-bromobenzyl, or m-chlorobenzyl.

EXAMPLE 82

4-(N—$L_n$)3-aminopropoxy-2,6-bis-hydroxymethylene pyridine

The 6 compounds diethyl-4-(N—$L_n$)3-aminopropoxy-2, 6-pyridinedicarboxylate ($L_n$=m-nitrobenzyl (Example 80), m-methylbenzyl, cinnamyl, m-cyanobenzyl, m-bromobenzyl, or m-chlorobenzyl) prepared in Examples 80 and 81 are converted into the 2,6-bis-dihydroxymethyl compounds by treatment with sodiumborohydride and calcium chloride after dissolution in dichloromethane to give the title compounds.

EXAMPLE 83

4-(N—$L_n$)3-aminopropoxy-2,6-bis-formal pyridine

The 6 compounds of Example 82 are treated as per the procedure of Example 52 to give the title compounds ($L_n$=m-nitrobenzyl (Example 80), m-methylbenzyl, cinnamyl, m-cyanobenzyl, m-bromobenzyl, or m-chlorobenzyl).

EXAMPLE 84

4-(N—$L_n$)(N-tritylsulfenyl)3-aminopropoxy-2,6-bis-formal pyridine 4-(N—$L_n$)3-aminopropoxy-2,6-bis-formal pyridine was treated with tritylsulfenylchloride as per the procedure of Example 44 to give the title compound.

EXAMPLE 85

Preparation of Library 34

2-(Aminomethylene)-4-(N—$L_n$)(N-tritylsulfenyl)3-aminopropoxy-6-[(N1-methylene-1-yl)-N2-[(t-Boc)-1-propanol-3-yl]-1,2-diaminoethane]pyridine An equimolar mixture of 4-(N—$L_n$)(N-tritylsulfenyl)3-aminopropoxy-2,6-bis-formal pyridine and N1[(t-Boc)-3-(O-amino)propanol1-yl]diaminoethane is treated as per the procedure of Example 7 to give the title Library.

EXAMPLE 86

Protection of Library 34, preparation of Library 35

2-(N-t-Butyldiphenylsilyl)aminomethylene-4-(N—$L_n$)(N-tritylsulfenyl)3-aminopropoxy-6-[(N1-methylene-1-yl)-N2–1(t-Boc)-1-propanol-3-yl]-1,2-diaminoethane]pyridine Library 34 is treated as per the procedure of Example 60 to give the title Library.

EXAMPLE 87

Preparation of Library 36

2-(N-t-Butyldiphenylsilyl)aminomethylene-4-(N—$L_n$)(N-trityl-sulfenyl)3-aminopropoxy-6-[(N1-$L_n$)(N1-methylene-1-yl)-N2-[(t-Boc)-1-propanol-3-yl]-1,2-diaminoethane)pyridine 2-(N-t-Butyldiphenylsilyl)aminomethylene-4-(N—$L_n$)(N-tritylsulfenyl)3-aminopropoxy-6-[(N1-methylene-1-yl)]-N2-[(t-Boc)-1-propanol-3-yl]-1,2-diaminoethane)pyridine is treated with an equimolar mixture of m-xylyl bromide ($L_8$—Br), m-nitrobenzyl bromide ($L_8$—Br), cinnamyl bromide ($L_{15}$—Br), m-cyanobenzyl bromide ($L_{16}$—Br), m-bromobenzyl bromide ($L_{17}$—Br), im-chlorobenzyl bromide ($L_8$—Br) as per the procedures of Examples 27–39 to give the title Library.

EXAMPLE 88

Deblocking of Library 36, preparation of Library 37

2-aminomethylene-4-(N—$L_n$)(N-tritylsulfenyl) 3-aminopropoxy-6 -[(N1—$L_n$)(N1-methylene-1-yl)-N2-[(t-Boc)-1-propanol-3-yl]-1,2-diaminoethanelpyridine 2-(N-t-Butyldiphenylsilyl)aminomethylene-4-(N—$L_n$) (N-tritylsulfenyl) 3-aminopropoxy-6-[(N1—$L_n$)(N1-methylene-1-yl)-N2-[(t-Boc)-1-propanol-3-yl]-1,2-diaminoethane]pyridine is treated as per the procedure of Example 62 to give the title Library.

EXAMPLE 89

Preparation of Library 38

2-(N-o-nitrophenylsulfonyl)aminomethylene-4-(N—$L_n$)(N-tritylsulfenyl)3-aminopropoxy-6-(N1—$L_n$)(N1-methylene-1-yl)-N2-[(t-Boc)-1-propanol-3-yl]-1,2-diaminoethane]pyridine 2-aminomethylene-4-(N—$L_n$)(N-tritylsulfenyl)3-aminopropoxy-6-[(N1-$L_n$)(N1-methylene-1-yl)]-N2-[(t-Boc)-1 -propanol-3-yl]-1,2-diaminoethane)pyridine is treated with o-nitrobenzenesulfonyl chloride as per the procedure of Example 63 to give the title Library.

EXAMPLE 90

Preparation of Library 39

2-(N-o-nitrophenylaulfonyl)(N—$L_n$) aminamethylene-4-(N—$L_n$)(N-tritylsulfenyl)3-aminopropoxy-6-[(N1-$L_n$)(N1-methylene-1-yl)N2-[(t-Boc)-1-propanol-3-yl]-1,2-diaminoethanelpyridine 2-(N-o-nitrophenylsulfonyl)aminomethylene-4-(N—$L_n$) (N-tritylsulfenyl)3-aminopropoxy-6-[(N1-$L_n$)(N1- methylene-1-yl)-N2-[(t-Boc)-1-propanol-3-yl]-1,2-diaminoethane]-pyridine is treated with an equimolar mixture of m-xylyl bromide ($L_6$—Br), m-nitrobenzyl bromide ($L_8$—Br), cinnamyl bromide ($L_{15}$—Br), m-cyanobenzyl bromide ($LI_6$—Br), m-bromobenzyl bromide ($L_{17}$—Br), m-chlorobenzyl bromide ($L_{19}$—Br) as per the procedures of Examples 27–39 to give the title Library.

EXAMPLE 91

Deprotection of Library 39, preparation of Library 40

2-(N—$L_n$)aminomethylene-4-(N—$L_n$)(N-tritylsulfenyl)3-aminopropoxy-6-[(N1-L)(N1-methylene-1-yl)-N2-[(t-Boc)-1-propanol-3-yl]-1,2-diaminoethane]pyridine 2-(N-o-nitrophenylsulfonyl)(N—$L_n$)aminomethylene-4-(N—$L_n$)(N-tritylsulfenyl)3-aminopropoxy-6-[(N1—L)(N1methylene-1-yl)-N2-[(t-Boc)-1-propanol-3-yl]-1,2-diaminoethane]pyridine is treated as per the procedure of Example 65 to give the title library.

EXAMPLE 92

Preparation of Library 41

2-(Bis-N,N—$L_n$)aminomethylene-4-(N—$L_n$)(N-tritylsulfenyl)3-aminopropoxy-6-[(N1-$L_n$)(N1-methylene-1-yl)-N2-[(t-Boc)-1-propanol-3-yl]-1,2-diaminoethanelpyridine 2-(N—$L_n$)aminomethylene-4-(N—$L_n$)(N-tritylsulfenyl)3-aminopropoxy-6-[(N1-$L_n$)(N1-methylene-1-yl)-N2-[(t-Boc)-1-propanol-3-yl]-1,2-diaminoethanelpyridine is treated with an equimolar mixture of m-xylyl bromide ($L_6$—Br), m-nitrobenzyl bromide ($L_8$—Br), cinnamyl bromide ($L_{15}$—Br), m-cyanobenzyl bromide ($L_{16}$—Br), m-bromobenzyl bromide ($L_{17}$—Br), m-chlorobenzyl bromide ($L_{18}$—Br) as per the procedures of Examples 27–39 to give the title Library.

EXAMPLE 93

Deprotection of Library 40, preparation of Library 41

2-(Bis-N,N—$L_n$)aminomethylene-4-(N—$L_n$)3-aminopropoxy-6-[(N1-$L_n$)(N1-methylene-1-yl)-N2-[(t-Boc)-1-propanol-3-yl]-1,2-diaminoethane]pyridine 2-(Bis-N,N—$L_n$)aminomethylene-4-(N—$L_n$)(N-tritylsulfenyl)3-aminopropoxy-6-[(N1-$L_n$)(N1-methylene-1-yl)-N2-[(t-Boc)-1-propanol-3-yl]-1,2-diaminoethane)pyridine (200 mmol) is dissolved in ethyl acetate and treated with 0.1 N HCl for 5 to 12 hours, adjusted to neutrality, and evaporated to dryness to provide a residue containing Library 41. Library 41 can be further purified by column chromatography.

EXAMPLE 94

Preparation of Library 42

2-(Bis-N,N—$L_n$)aminonmethylene-4-(Bis-N,N—L)3-aminopropoxy-6-[(N1-$L_n$)(N1-methylene-1-yl)-N2-[(t-Boc)-1-propanol-3-yl]-1,2-diaminoethane]pyridine 2-(Bis-N,N—$L_n$)aminomethylene-4-(N—$L_n$)3-aminopropoxy-6-((N1-$L_n$)(N1-methylene-1-yl)-N2-[(t-Boc)-1-propanol-3-yl]-1,2-diaminoethane]pyridine is treated with an equimolar mixture of m-xylyl bromide ($L_6$—Br), m-nitrobenzyl bromide ($L_8$—Br), cinnamyl bromide ($L_{15}$—Br), m-cyanobenzyl bromide ($L_{16}$—Br), m-bromobenzyl bromide ($L_{18}$—Br), m-chlorobenzyl bromide ($L_{18}$—Br) as per the procedures of Examples 27–39 to give the title Library.

EXAMPLE 95

Deprotection of Library 42, preparation of Library 43

2-(Bis-N,N—$L_n$)aminomethylene-4-(Bis-N,N—$L_n$) 3-aminopropoxy-6-[(N1-$L_n$)(N1-methylene-1-yl)-N2-[1-propanol-3-yl]-1,2-diaminoethane]pyridine 2-(Bis-N,N—$L_n$)aminomethylene-4-(Bis-N,N—$L_n$)3-aminopropoxy-6-[(N1-$L_n$)(N1-methylene-1-yl)-N2-[(t-Roc)-1-propanol-3-yl]-1,2-diaminoethanelpyridine is treated with TFA as per the procedure of Example 8 to give the title Library.

EXAMPLE 96

Preparation of Library 44

2-(Bis-N-N,N—$L_n$)aminomethylene-4-(Bis-N,N—$L_n$)3-aminopropoxy-6-[(N1-$L_n$)(N1-methylene-1-yl)-N2-($L_n$)1-propanol-3-yl]-1,2-diaminoethane]pyridine 2-(Bis-N,N—$L_n$)aminomethylene-4-(Bis-N,N—$L_n$)3-aminopropoxy-6-[(N1-$L_n$)(N1-methylene-1-yl)-N2-[1-propanol-3-yl]-1,2-diaminoethane]pyridine is treated with an equimolar mixture of m-xylyl bromide ($L_6$—Br), m-nitrobenzyl bromide ($L_8$—Br), cinnamyl bromide ($L_{25}$—Br), m-cyanobenzyl bromide ($L_6$—Br), m-bromobenzyl bromide ($L_{17}$—Br), m-chlorobenzyl bromide ($L_{18}$—Br) as per the procedures of Examples 27–39 to give the title Library.

EXAMPLE 97

2-(N—$L_a$)(N—$L_b$)aminamethylene-4-(N—$L_c$)(N—$L_d$)3-aminopropoxy-6-[(N—$L_e$)(N1-methylene-1-yl)-N2-[(N—$L_f$)1-propanol-3-yl]-1,2-diaminoethane]pyridine The title compound is prepared following the procedures of Examples 79–96. In each step resulting in the addition of a letter only one reactive form of a letter is used. The reactive forms of the letters are selected from m-xylyl bromide ($L_6$—Br), m-nitrobenzyl bromide ($L_{18}$—Br), cinnamyl bromide ($L_{15}$—Br), in-cyanobenzyl bromide ($L_{16}$—Br), m-bromobenzyl bromide ($L_{17}$—Br), m-chlorobenzyl bromide ($L_{18}$—Br) 2-(Bis-N,N—$L_n$). The final compound is substituted with 6 letters at 6 sites.

EXAMPLE 98

Synthesis of Libraries having the structure 2-(N—$L_a$)(N—$L_b$)aminomethylene-4-(N—$L_c$)(N—$L_d$) 3-aminopropoxy-6-[(N—$L_e$)(N1-methylene-1-yl)-N2-[(N—$L_f$)1-propanol-3-yl]-1,2-diaminoethane] pyridine using various selected halides Using the procedure of Examples 79–97, libraries are prepared that are derivatized with one, two, three, four or more of the following halides available from Aldrich Chemical Company, Inc., Milwaukee, Wis. The Aldrich catalog number is given in the left hand column and the compound name is given in the right hand column:

13925-4 Alpha,2,4-trichlorotoluene
19349-6 2-Iodobenzyl chloride
25917-9 Alpha-3,4-trichlorotoluene
10733-6 2-Nitrobenzyl chloride
10030-7 Alpha-bromo-2,6-dichlorotoluene
T5630-8 Alpha-2,6-trichlorotoluene
14011-2 4-Nitrobenzyl chloride
19164-7 3,5-Dinitrobenzyl chloride
13672-7 3-Chlorobenzyl bromide
19166-7 3-Nitrobenzyl chloride
30726-2 2,4-Dinitrobenzyl chloride
25225-5 2-Chlorobenzyl bromide
C5490-2 2-Chloromethyl-4-nitrophenol
42369-6 3,5-Dinitrobenzyl chloride
F760-1 2-Fyluorobenzyl chloride
11196-1 4-Chlorobenzyl chloride
21811-1 2-Chloro-6-fluorobenzyl chloride
F780-6 3-Fluorobenzyl chloride
11522-3 3-Chlorobenzyl chloride
19625-8 4-Chloro-2-nitrobenzyl chloride
F800-4 4-Fluorobenzyl chloride
11588-6 3-Chlorobenzyl chloride
27250-7 2-Chloro-2',4'-difluoroacetophenone
19425-5 2-Chlorobenzyl chloride
24118-0 2-Chlorobenzyl chloride
15907-7 Alpha-4-dichloroanisole
13359-0 Benzyl chloride
S62774-7 2-(Chloromethyl)benzonitrile
S77343-3 N-(2-Chloroethylidene)-2,4-dinitroaniline
16770-3 Alpha'-chloro-alpha,alpha, alpha-trifluoro-m-xylene
25070-8 Alpha,-chloro-alpha,alpha,alpha-trifluoro-o-xylene
36581-5 Alpha'-chloro-alpha,alpha,alpha-trifluoro-p-xylene
19875-7 4-Bromophenyl 2-chloroethyl ether
30511-1 2-Chlorophenyl 2-bromoethyl ether
S67805-8 2-(2-Bromoethoxy)-5-chloro-1-nitrobenzene
S60515-8 2-Bromoethyl-4-chlorophenyl ether
S45235-1 1-(2-Chloroethyl)-4-fluorobenzene
19177-9 5-Methyl-2-nitrobenzyl chloride
19232-5 5-Methyl-3-nitrobenzyl chloride
19536-7 2-Methyl-3-nitrobenzyl chloride
C7330-3 Alpha-chloro-o-xylene
S43061-7 Beta-chlorophenetole
S92214-5 3-Methyl-4-nitrobenzyl chloride
C7335-4 Alpha-chloro-m-xylene
C7340-0 Alpha-chloro-p-xylene
20938-4 3-Methoxybenzyl chloride
41760-2 2-Chloroethylphenyl sulfide
27024-5 4-Methoxybenzyl chloride
26340-0 3,5-Bis(trifluoromethyl)benzyl chloride
S61404-1 2-Chloroethyl-4-chlorophenyl sulfide
$C_{4040}$-5 (2-chloroethyl)benzene
S44579-7 4'-Bromo-3-chloropropiophenone
S65169-9 2-Chloroethyl-4-nitrobenzoate
13515-1 3-Chloro-4'-fluoropropiophenone
33561-4 3-Chloropropiophenone
S88196-1 Benzyl-2-chloroacetate
S83340-1 3-Chloropropyl-2,4-dichlorophenyl ether
953571-0 3-Chloropropyl-4-fluorophenyl ether
12640-3 2,5-Dimethylbenzyl chloride
C6810-5 1-Chloro-3-phenylpropane
S80872-5 2,5-Dimethoxybenzyl chloride
D15060-6 3,4-Dimethylbenzyl chloride
S56939-9 3-Chloropropyl-4-nitrophenyl ether
S79921-1 3-Chloropropyl-phenyl sulfide
S79298-5 3-Chloropropyl-phenyl ether
S83280-4 2-Chloroethyl-p-tolyl sulfide
S63793-9 4-Chlorobenzyl-2-chloroethyl sulfide
33026-4 3,5-Dimethoxybenzyl chloride
S37787-2 N-(2-Chloroethyl)benzylamine HCl
36344-8 4-Chlorobutyrophinone
S55923-7 7-Chloro-p-cymene
S66335-2 2,4,5-Trimethylbenzyl chloride
S56937-2 1-(2-(2-Chloroethoxy)-ethoxy)-4-nitrobenzene
P1530-7 4-Phenoxybutyl chloride
S40755-0 4,6-Bis(chloromethyl)-m-xylene
13698-0 Alpha-2-chloroisodurene
24650-6 1-Chloro-2-methyl-2-phenylpropane
S34433-8 4-Chloro-4'-methylbutyrophenone
S95372-5 4-Bromophenyl-3-chloro-2,2-dimethylpropionate
39086-0 4-Chlorobutylbenzoate
S79927-0 3-Chloro-1-methylpropylphenyl sulfide
S34430-3 4-Chloro-4'-methoxybutyrophenone
S79928-9 3-Chloropropyl-m-toluyl sulfide
S42717-9 N-(2-Chloroethyl)-N-methylbenzylamine hydrochloride
S52026-8 4-tert-Butyl-1-chloromethyl-2-nitrobenzene
D6560-7 2,4-Bis(chloromethyl)-1,3,5-trimethylbenzene
19153-1 4-(tert-Butyl)benzyl chloride
S62686-4 2,3,5,6-Tetramethylbenzyl chloride
S87624-0 (+)-1-Chloro-3-methyl-2-phenylbutane
S35320-5 4-(2-Methylphenoxy)butyl chloride
S37684-1 N-(2-chloroethyl)-N-ethylbenzylamine HCl
S36329-4 3-Methoxy-3-(4-tolyl)-propyl chloride
S42735-7 N-(3-chloropropyl)-N-methylbenzylamine HCl
S34414-1 4-Chloro-3',4'-dimethylbutyrophenone
S36370-7 4-(3-Methylphenoxy)butyl chloride
S66008-6 N-(2-Chloroethyl)-N-ethyl-m-toluidine
34420-6 4-Chloro-4'-ethylbutyrophenone
S36371-5 4-(4-methylphenoxy)butyl chloride
S34409-5 4-Chloro-2',4'-dimethoxybutyrophenone
S79934-3 5-Chloropentylphenyl sulfide
S52555-3 5-Chloro-2-(o-tolyl)-valeronitrile
S52133-7 Alpha-chloro-4-(tert-pentyl)-toluene
S87628-3 (+)-1-Chloro-3,3-dimethyl-2-phenylbutane
35168-7 3-Isopropoxy-3-phenylpropyl chloride
10086-2 3,6-Bis(chloromethyl)durene
S37754-6 1-Chloro-3-mesityloxy-2-propanol 66289-5 Alpha,alpha-3-dichlorohexamethylbenzene
86989-9 1,2-Bis(chloromethyl)-3,4,5,6-tetramethylbenzene
86009-3 1,4-Bis(chloromethyl)-2,5-diethoxybenzene
S52500-6 2-Chloromethyl-4-nitrophenylheptyl ether
54873-1 2-(2-Chloroethyl)-2-phenylpentanenitrile
S36287-5 3-Isopropoxy-3-(p-toluyl)propyl chloride
B9140-4 4'-tert-Butyl-4-chlorobutyrophenone
C8,121-7 cinnamyl bromide
18,706-2 3-bromobenzylbromide
15,791-0 methyl bromoacetate
24,248-9 bromoacetonitrile
30,127-2 bromoacetamide
36,242-5 2-chloro-N-methoxy-N-methylacetamide
17568 3-bromomethylbenzonitrile (Fluka)

EXAMPLE 99

Synthesis of Libraries having the structure 2-(N—$L_a$)(N—$L_b$)aminomethylene-4-(N—$L_c$)(N—$L_d$)3-aminopropoxy-6-[(N—$L_e$)(N1-methylene-1-yl)-N2-(N—$L_f$)1-propanol-3-yl]-1,2-diaminoethane] pyridine using various selected aldehydes Using the procedure of Examples 79–97, libraries are prepared that are derivatized with one, two, three, four or more of the following aldehydes available from Aldrich Chemical Company, Inc., Milwaukee, Wis. The Aldrich catalog number is given in the left hand column and the compound name is given in the right hand column: Synthesis of libraries from cyclophanes and aldehydes using various selected aldehydes 10793-5 Phenylacetaldehyde
D20425 Diphenylacetaldehyde
24582-8 Hydrocinnamaldehyde
24136-9 Phenylpropionaldehyde
28902-7 (+/−)-3-Phenylbutyraldehyde
28899-3 Alpha-amylcinnamaldehyde
16116-0 Alpha-bromocinnamaldehyde
26813-5 4-Stilbenecarboxaldehyde
B133-4 Benzaldehyde
11755-2 o-Tolualdehyde
25069-4 Alpha.alpha.alpha-trifluoro-o-tolualdehyde
F480-7 2-Fluorobenzaldehyde
12497-4 2-Chlorobenzaldehyde
B5700-1 2-Bromobenzaldehyde
10962-2 o-Anisaldehyde
15372-9 2-Ethoxybenzaldehyde
N1080-2 2-Nitrobenzaldehyde
T3550-5 m-Tolualdehyde
19687-8 Alpha.alpha.alpha-trifluoro-m-tolualdehyde
F500-5 3-Fluorobenzaldehyde
C2340-3 3-Chlorobenzaldehyde
B5720-6 3-Chlorobenzaldehyde
AS12965-8 m-Anisaldehyde
34648-9 3-(Trifluoromethoxy)-benzaldehyde
34199-1 3-(1,1,2,2-Tetrafluoroethoxy)-benzaldehyde
H1980-8 3-Hydroxybenzaldehyde
N1084-5 3-Nitrobenzaldehyde
11528-2 Isophthaldehyde
T3560-2 p-Tolualdehyde
23363-3 4-Ethylbenzaldehyde
13517-8 4-Isopropylbenzaldehyde
22494-4 Alpha.alpha.alpha-trifluoro-p-tolualdehyde
12837-6 4-Fluorobenzaldehyde
1
1221-6 4-Chlorobenzaldehyde
5740-0 4-Bromobenzaldehyde
A8810-7 p-Anisaldehyde
17360-6 4-Ethoxybenzaldehyde
33363-8 4-Propoxybenzaldehyde
23808-2 4-Butoxybenzaldehyde
37060-6 4-(Trifluoromethoxy)-benzaldehyde
27486-0 Terephthaldehyde mono-(diethyl acetal)
14408-8 4-Hydroxybenzaldehyde
22277-1 4-(Methylthio)benzaldehyde
10976-2 4-(Dimethylamino)benzaldehyde
D8625-6 4-(Dimethylamino)benzaldehyde
33851-6 4-(Dibutylamino)benzaldehyde
29355-5 4-(3-Dimethylaminopropoxy)benzaldehyde
13017-6 4-Nitrobenzaldehyde
T220-7 Terephthaldicarboxaldehyde
34252-1 3-Fluoro-2-methylbenzaldehyde
34649-7 2-Fluoro-3-(trifluoromethyl)-benzaldehyde
26514-4 2,3-Difluorobenzaldehyde
26515-2 2,6-Difluorobenzaldehyde
14124-0 2-Chloro-6-fluorobenzaldehyde
D5650-0 2,6-Dichlorobenzaldehyde
25483-5 2,3-Dichlorobenzaldehyde
D13020-6 2,3-Dimethoxybenzaldehyde
29250-8 2,6-Dimethoxybenzaldehyde
31980-5 3-Fluorosalicylaldehyde
12080-4 o-Vanillin
18983-9 2,3-Dihydroxybenzaldehyde
10604-6 2-Chloro-6-nitrobenzaldehyde
16382-1 3-methoxy-2-nitrobenzaldehyde
11750-1 2,6-Dinitrobenzaldehyde
15104-1 2,4-Ditnethylbenzaldehyde
15106-8 2,5-Dimethylbenzaldehyde
37682-5 2-Chloro-5-(trifluoromethyl)benzaldehyde
26516-0 3,4-Difluorobenzaldehyde
26517-9 2,4-Difluorobenzaldehyde
26518-7 2, 5-Difluorobenzaldehyde
30600-2 3-Chloro-4-fluorobenzaldehyde
34807-4 2-Chloro-4-fluorobenzaldehyde
33954-7 3-Bromo-3-fluorobenzaldehyde
D5660-8 3,4-Dichlorobenzaldehyde
14675-7 2,4-Dichlorobenzaldehyde
15212-9 3-Methyl-p-anisaldehyde
15558-6 3-Fluoro-p-anisaldehyde
15429-6 5-Bromo-o-anisaldehyde
D13040-0 2,4-Dimethoxybenzaldehyde
D13060-5 2,5-Dimethoxybenzaldehyde
14375-8 3,4-Dimethoxybenzaldehyde
25275-1 3-Ethoxy-4-methoxybenzaldehyde
P4910-4 Piperonal 26459-8 1,4-Benzodioxan-6-carboxaldehyde
31691-1 4-Hydroxy-3-methylbenzaldehyde
34606-3 2-Chloro-4-hydroxybenzaldehyde
25975-6 5-Chlorosalicylaldehyde
13728-6 5-Bromosalicylaldehyde
14686-2 2-Hydroxy-5-methoxybenzaldehyde
16069-5 2-Hydroxy-4-methoxybenzaldehyde
14368-5 3-Hydroxy-4-methoxybenzaldehyde
V110-4 Vanillin
12809-0 3-Ethoxy-4-hydroxybenzaldehyde
34215-7 5-(Trifluoromethoxy)salicylaldehyde
D10840-5 3,4-Dihydroxybenzaldehyde
D10820-0 2,5-Dihydroxybenzaldehyde
16863-7 2,4-Dihydroxybenzaldehyde
22568-1 4-(Diethylamino)salicylaldehyde
$C_{5880}$-0 5-Chloro-2-nitrobenzaldehyde
13903-3 2-Chloro-5-nitrobenzaldehyde
$C_{5870}$-3 4-Chloro-3-nitrobenzaldehyde
14432-0 4-Hydroxy-3-nitrobenzaldehyde
15616-7 3-Hydroxy-4-nitrobenzaldehyde
27535-2 2-Hydroxy-5-nitrobenzaldehyde
$H_{4810}$-7 5-Hydroxy-2-nitrobenzaldehyde
D19360-7 2,4-Nitrobenzaldehyde
29013-0 3,5-Bis(trifluoromethyl)benzaldehyde
29017-3 3,5-Difluorobenzaldehyde
13940-8 3,5-Dichlorobenzaldehyde
36811-3 3,5-Dihydroxybenzaldehyde
12269-2 3,5-Dimethoxybenzaldehyde
36810-5 3,5-Dibenzyloxybenzaldehyde
M680-8 Mesitaldehyde
29233-8 2,3,5-Trichlorobenzaldehyde
13061-3 5-Bromoveratraldehyde
13871-1 2,4,6-Trimethoxybenzaldehyde
T6840-3 3,4,5-Trimethoxybenzaldehyde
14039-2 3,5-Dimethyl-4-hydroxybenzaldehyde
35768-5 2,6-Dimethyl-4-hydroxybenzaldehyde
14040-6 3,5-Di-tert-butyl-4-hydroxybenzaldehyde hemihydrate
26181-5 3,5-Dichlorosalicylaldehyde
12213-0 3,5-Dibromosalicylaldehyde
28344-4 3,5-Diiodosalicylaldehyde
13060-5 5-Bromovanillin
12948-8 5-odovanillin
13879-7 4,6-Dimethoxysalicylaldehyde
25871-7 5-Nitrovanillin
S760-2 3,5-Dinitrosalicylaldehyde
25959-4 2,5-Dimethyl-p-anisaldehyde
T6540-4 5-Bromo-2,4-dimethoxybenzaldehyde
N2800-0 4-Nitrovanillin
27680-4 3,5-Dinitrosalicylaldehyde
15205-6 2,5-Dimethyl-p-anisaldehyde
29251-6 5-Bromo-2,4-dimethoxybenzaldehyde
15557-8 6-Bromoveratraldehyde
13215-2 2,4,5-Trimethoxybenzaldehyde
27960-9 6-Nitroveratraldehyde
13765-0 6-Nitropiperonal
27679-0 2,5-Dichloroterephthaldehyde
33066-3 2,3,4-Trifluorobenzaldehyde
29231-1 2,3,6-Trichlorobenzaldehyde
15201-3 2,3-Dimethyl-p-anisaldehyde
29627-9 2,4-Dimethoxy-3-methylbenzaldehyde
15209-9 2,3,4-Trimethoxybenzaldehyde
26084-3 2,3,4-Trihydroxybenzaldehyde
32893-6 Tetrafluorobenzaldehyde
10374-8 Pentafluorobenzaldehyde
B3468-0 4-Biphenylcarboxaldehyde
19175-2 3-Phenoxybenzaldehyde
B2700-5 3-Benzloxybenzaldehyde
19540-5 3-(4-Methylphenoxy)benzaldehyde
19592-8 3-(4-tert-Butylphenoxy)benzaldehyde
19539-1 3-[3-(Trifluoromethyl)phenoxy]benzaldehyde
19530-8 3-(4-Chlorophenoxy)benzaldehyde
19590-1 3-(3, 4-Dichlorophenoxy)benzaldehyde
19774-2 3-(3,5-Dichlorophenoxy)benzaldehyde
19589-8 3-(4-Methoxyphonoxy)benzaldehyde
21126-5 4-Phenoxybenzaldehyde
12371-4 4-Benzyloxybenzaldehyde
16361-9 4-Benzyloxy-3-methoxybenzaldehyde
16395-3 3-Benzyloxy-4-methoxybenzaldehyde
34603-9 3-Methoxy-4-(4-nitrobenzyloxy)benzaldehyde
D3600-3 3,4-Dibenzyloxybenzaldehyde
N1o-9 1-Naphthaldehyde
N20-6 2-Naphthaldehyde
15134-3 2-Methoxy-1-naphthaldehyde
10324-1 4-Methoxy-1-naphthaldehyde
$H_{4535}$-3 2-Hydroxy-1-naphthaldehyde
27208-6 4-Dimethylamino-1-naphthaldehyde
38201-9 2,3-Naphthalendicarboxaldehyde
15014-2 2-Fluorenecarboxaldehyde
27868-8 9-Anthraldehyde
M2965-7 10-Methylanthracene-9-carboxaldehyde
15211-0 10-Chloro-9-anthraldehyde
P1160-3 Phenanthrene-9-carboxaldehyde
14403-7 1-Pyrenecarboxaldehyde
Aliphatic aldehydes
25254-9 Fromaldehylde
11007-8 Acetaldehyde
P5145-1 Propionaldehyde
24078-8 Isobutyraldehyde
T7150-1 Trimethylacetaldehyde
B10328-4 Butyraldehyde
M3347-6 2-Methylbutyraldehyde
11009-4 2-Ethylbutyraldehyde
14645-5 Isovaleraldehyde
35990-4 3,3-Dimethylbutyraldehyde
11013-2 Valeraldehyde
25856-3 2-Methylvaleraldehyde
D19050-0 2,4-Dimethylvaleraldehyde
11560-6 Hexanal
E2910-9 2-Ethylhexanal
30355-0 3,5,5-Trimethylhexanal
$H_{212}$-0 Heptaldehyde
0560-8 octyl aldehyde
N3080-3 Nonyl aldehyde 12577-6 Decyl aldehyde
U220-2 Undecylic aldehyde
M8675-8 2-Methylundecanal
D22200-3 Dodecyl aldehyde
26923-9 Tridecanal
T1000-6 Tetradecy aldehyde
11022-1 Acrolein
13303-5 Methacrolein
25614-5 2-Ethylacrolein
25613-7 2-Butylacrolein
13298-5 Crotonaldehyde
19261-9 trans-2-Methyl-2-butenal
29468-3 2-Ethyl-trans-2-butenal
30407-7 3-Methyl-2-butenal
26925-5 trans-2-pentenal
29466-7 2-Methyl-2-pentenal
29097-1 2,2-Dimethyl-4-pentenal
13265-9 trans-2-Hexenal
25176-3 trans-2-Heptenal
30796-3 2,6-Dimethyl-5-heptenal
26995-6 trans-2-Octenal
34364-1 (R)-(+)-Citronellal
37375-3 (S)-(−)-Citronellal
25565-3 trans-2-Nonenal
37562-4 cis-4-Decenal
36733-8 trans-4-Decenal
13227-6 Undecylenic aldehyde
24911-4 dis-9-hexadecenal
27221-3 Cyclopropanecarboxaldehyde
10846-4 Cyclohexanecarboxaldehyde
10933-9 Cyclooctanecarboxaldehyde
30441-7 3-Cyclohexylpropionaldehyde
T1220-3 Tetrahydrobenzaldehyde
21829-4 (S)-(−)-Perillaldehyde
26467-9 2,6,6-Trimethyl-1-cyclohexene-1-acetaldehyde
10937-1 5-Norbornen-2-carboxaldehyde
21824-3 (1R)-(−)-Myrtenal
37531-4 Glyoxal-1,1-dimethyl acetal
21877-4 7-Methoxy-3,7-dimethyloctanal
23254-8 3-Ethoxymethacrolein
27525-5 2,5-Dimethoxy-3-tetrahydrofurancarboxaldehyde
26918-2 2,2-Dimethyl-3-hydroxypropionaldehyde
G480-2 DL-Glyceraldehyde
G478-0 D-Glyceraldehyde
21665-8 L-Glyceraldehyde
34140-1 3-(Methylthio)propionaldehyde
30583-9 3-(Dimethylamino)acrolein
36549-9 3-(Dimethylamino)-2-methyl-2-propenal
17733-4 Pyrubic aldehyde
27706-1 (S)-(−)-2-(Methoxymethyl)-1-pyrrolidinecarboxaldehyde
29211-7 2-Methoxy-1-pyrrolidinecarboxaldehyde
29210-9 2-Methoxy-1-piperidinecarboxaldehyde

EXAMPLE 100

N1-Hydroxypropyl-N2-(o-nitrophenyloulfonyl)-diaminoethane

A solution of 2-nitrobenzenesulfonyl chloride (Aldrich, 5.32 g, 24 mmol, 2.4 eq) in dichloromethane (30 mL) is added dropwise to a stirred solution of N-hydroxypropyl diaminoethane (TCI) (10 mmol) and triethylamine (8 mL) in dichloromethane (30 mL) at 0° C. The resulting reaction mixture is allowed to warm to room temperature and further stirred for 1 hour. The mixture is diluted with chloroform and washed with water and brine. The organic phase is dried ($Na_2SO_4$) and the solvent is evaporated under reduced pressure. The residue is purified by flash chromatography on a silica gel column (20 cm×3 cm) to give the title compound.

EXAMPLE 101

N1-Hydroxypropyl(T-boc)-N2-(o-nitrophenylsulfonyl)-diaminoethane

N1-Hydroxypropyl-N2-(o-nitrophenylsulfonyl)-diaminoethane (8.14 mmol) and triethylamine were added to dichloromethane (40 mL). Di-tert-butyl-dicarbonate (16.28 mmol) is added in one portion. The reaction is stirred at room temperature for 4 hours and is monitored by TLC. The reaction mixture is washed 3× with water and once with brine, dried over $MgSO_4$, filtered, and concentrated. The residue is purified by silica gel flash column chromatography to give the title compound.

EXAMPLE 102 m-phthalimidomethyl-α-Bromo-xylene

α,α'-Dibromo-m-xylene is refluxed with potassium phthalimide (1.0 equivalent) in acetonitrile to give the title compound.

EXAMPLE 103

3-Phthalimidamethyl-1-[N1-(o-nitrophenylsulfonyl)(methylene-1-yl)-N2-(3-hydroxypropyl)(t-boc)diaminoethane]benzene N1-Hydroxypropyl(T-boc)-N2-(o-nitrophenylsulfonyl)-diaminoethane and m-phthalimidomethyl-α-Bromo-xylene are dissolved in DMF and $K_2CO_3$ is added. The mixture is stirred at room temperature for 16 hours and concentrated. The residue is purified by silica gel flash column chromatography to give the title compound.

EXAMPLE 104

3-(aminomethylene-1yl)-1-[N1-(o-nitrophenylsulfonyl)(methylene-1-yl)-N2-(3-hydroxypropyl) (t-boc) diaminoethane]benzene 3-Phthalimidomethyl-1-[N1-(o-nitrophenylsulfonyl)-(methylene-1-yl)-N2-(3-hydroxypropyl)(t-boc)diaminoethanelbenzene is treated with hydrazine as per the procedure of Example 6 to give the title compound.

EXAMPLE 105

Preparation of Library 51

Figure 10:
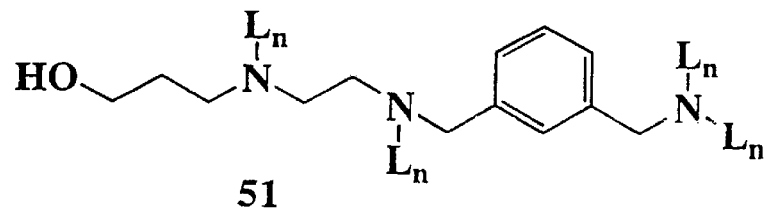
FIG. 10 shows representative libraries according to the invention.
Figure 10:
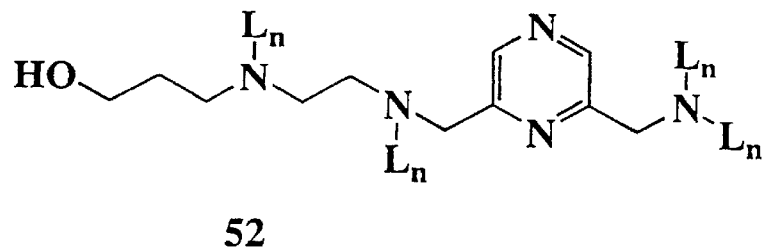
Figure 10:
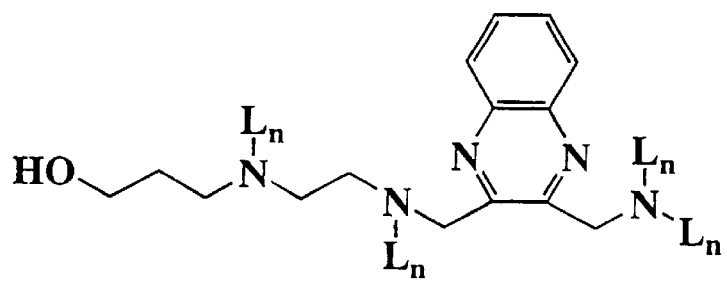
Figure 10:
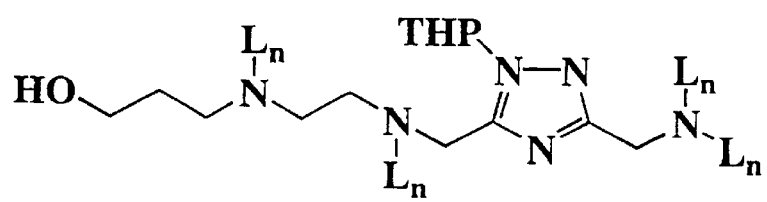
Figure 10:
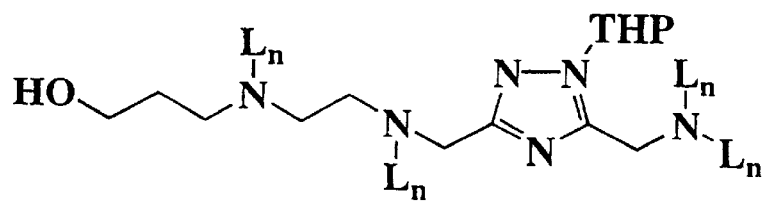

3-(N—$L_n$)(N—$L_n$)aminomethylene-1-[(N—$L_n$)(N1-methylene-1-yl)-N2-[(N—$L_n$)1-propanol-3-yl]-1,2-diaminoethane]benzene (FIGS. 8–10)

Following the procedures of Examples 60–68 the above library is prepared wherein $L_n$ is a combinatorial distribution of from 2 to about 6 letters.

EXAMPLE 106

3-(N—$L_a$)(N—$L_b$)aminomethylene-1-[(N—$L_c$)(N1-methylene-1-yl)-N2-[(N—$L_d$)1-propanol-3-yl]-1,2-diaminoethane]benzene Following the procedures of Examples 60–68 the above compound is prepared wherein $L_a$, $L_b$, $L_c$, and $L_d$ are each a single letter.

EXAMPLE 107

α,α'-Dichloro-2,6-dimethylpyrazine

A stirred mixture of 2,6-dimethylpyrazine (55 mmol), N-chlorosuccinimide (110 mmol) and benzoylperoxide (1.0 mmol) in carbon tetrachloride (150 mL) is heated to reflux under nitrogen for 30 hours. Additional N-chlorosuccinimide (140 mmol) and benzoylperoxide (2.3 mmol) are added at 6 hours. The cooled reaction mixture is filtered and the filtrate washed with sodium carbonate (saturated aqueous solution) and dried. Evaporation of the solvent gives the title compound.

EXAMPLE 108

Preparation of Library 52

3-(N—$L_n$)(N—$L_n$)aminomethylene-1-[(N—$L_n$)(N1-methylene-1-yl)-N2[L(N—$L_n$)1-propanol-3-yl]-1,2-diaminoethane]pyrazine (FIG. 10)

Starting with α,α'-dichloro-2,6-dimethylpyrazine and following the procedures of Examples 102–106 the title library wherein $L_n$ is a combinatorial mixture of from 2 to about 6 letters is prepared.

EXAMPLE 109

3-(N—$L_a$)(N—$L_b$)aminomethylene-1-[(N—$L_c$)(N1-methylene-1-yl)-N2-(N—$L_d$)1-propanol-3-yl-1,2-diaminoethane] pyrazine Starting with α,α'-dichloro-2,6-dimethylpyrazine and following the procedures of Examples 102–106 the title compound is prepared wherein $L_a$, $L_b$, $L_c$, and $L_d$ are each a single letter.

EXAMPLE 110

Preparation of Library 53

2-(N—$L_n$)(N—$L_n$)aminamethylene-3-[(N—$L_n$)(N1-methylene-1-yl)-N2-[(N—$L_n$)1-propanol-3-yl]-1,2-diaminoethane]quinoxaline (FIG. 10)

Starting with 2,3-bis(bromomethyl)quinoxaline and following the procedures of Examples 102–106 the title library wherein Ln is a combinatorial mixture of from 2 to about 6 letters is prepared.

EXAMPLE 111

2-(N—$L_a$)(N—$L_b$)aminomethylene-3-[(N—$L_c$)(N1-methylene-1-yl)-N2-[(N—$L_d$)1-propanol-3-yl]-1,2-diaminoethane]quinoxaline Starting with 2,3-bis(bromomethyl)quinoxaline and following the procedures of Examples 102–106 the title compound is prepared wherein Law $L_a$, $L_b$, $L_c$, and $L_d$ are each a single letter.

EXAMPLE 112

Preparation of Libraries 54 and 55

1-Tetrahydropyranyl-3-(N—$L_n$)(N—$L_n$) aminomethylene-5-[(N—$L_n$)(N1-methylene-1-yl)-N2-[(N—$L_n$)1-propanol-3-yl]-1,2-diaminoethane]1,2,4-triazole Library 48, 1-Tetrahydropyranyl- 5-(N—$L_n$)(N—$L_n$)aminomethylene-3-[(N—$L_n$)(N1-methylene-1-yl)-N2-[(N—$L_n$) 1-propanol-3-yl]-1,2-diaminoethane]1,2,4-triazole Library 49 (FIG. 10)

Starting with 1-tetrahydropyranyl-3,5-bis-chloromethyl-1,2,4-triazole(prepared as per the procedure of J. S. Bradshaw, et al., *J. Heterocycl. Chem.*, 1986, 23, 361–368) and following the procedures of Examples 102–106 the title libraries wherein Is is a combinatorial mixture of from 2 to about 6 letters is prepared. In the first step of synthesis, the 1-tetrahydropyranyl-3,-bis-chloromethyl-1,2,4-triazole is reacted with N-hydroxyphthalimide as per Example 102. This step will yield 2 compounds after purification due to the asymmetry of the reacting heterocycle. The tetrahydropyranyl group is removed by treatment with HCl.

EXAMPLE 113

1-Tetrahydropyranyl-3-(N—$L_a$)(N—$L_b$) aminomethylene-5-[(N—$L_c$)(N1-methylene-1-yl)-N2-[(N—$L_d$)1-propanol-3-yl]-1,2-diaminoethane]1,2,4-triazole, 1-Tetrahydropyranyl-5-(N—$L_n$)(N—$L_b$)aminomethylene-3-[(N—$L_c$)(N1-methylene-1-yl)-N2-[(N—$L_d$)1-propanol-3-yl]-1,2-diaminoethane]1,2,4-triazole Starting with 1-tetrahydropyranyl-bis-3,5-chloromethyl-1,2,4-triazole (prepared as per the procedure of J. S. Bradshaw, et al., *J. Heterocycl. Chem.*, 1986, 23, 361–368) and following the procedures of Examples 102–106 the title compound is prepared wherein $L_a$, $L_b$, $L_c$, and $L_d$ are each a single letter. In the first step of synthesis, the 1-tetrahydropyranyl-3,5-bis-chloromethyl-1,2,4-triazole is reacted with N-hydroxyphthalimide as per Example 102. This step will yield 2 compounds after purification due to the asymmetry of the reacting heterocycle. The tetrahydropyranyl group is removed by treatment with Hcl.

EXAMPLE 114

Preparation of Library 56

2-(N—$L_n$)(N—$L_n$)aminomethylene-5-[(N—$L_n$)(N1-methylene-1-yl)-N2-[(N—$L_n$)1-propanol-3-yl]-1,2-diaminoethane]furan Starting with 2,5-furandimethanol and following the procedures of Examples 102–106 the title library is prepared wherein $L_a$, $L_b$, $L_c$, and $L_d$ are each a single letter.

EXAMPLE 115

2-(N—$L_a$)(N—$L_b$)aminomethylene-5-[(N—$L_c$)(N1-methylene-1-yl)-N2-[(N—$L_d$)1-propanol-3-yl]-1,2-diaminoethane]furan Starting with 2,5-furandimethanol and following the procedures of Examples 102–106 the title compound is prepared wherein $L_a$, $L_b$, $L_c$, and $L_d$ are each a single letter.

EXAMPLE 116

3-(N-Acridinyl)-aminobenzyl alcohol

A solution of 3-aminobenzyl alcohol (Aldrich) (2.0 g, 16.2 mmol) and N,N'-bis(tert-butoxycarbonyl)-1H-carboxamidine (prepared as per the procedure of Bernatowicz, M. S., *Tetrahedron Lett.*, 1993, 34, 3389–3392) (4.53 g, 14.62 mmol) in mL of dry THF was stirred at room temperature for 2 days. The solvent was evaporated, and the residue was dissolved in CHCl$_3$. The solution was washed with water and brine, dried (Na$_2$SO$_4$) and concentrated. The residue was purified by flash chromatography on a silica gel column. Elution with 200:1 CH$_2$Cl$_2$—MeOH and then 4:1 hexanes-EtOAc gave the title compound as a white foam, yield 4.95 g (91.0%).

$^1$H NMR δ1.51 (s, 9H), 1.54 (s, 9H), 4.68 (s, 2H), 7.12 (d, 1H, J=7.8 Hz), 7.34 (t, 1H, J=7.8 Hz), 7.58 (d, 2H, J=7.8 Hz), 10.36 (S, 1H), 11.61 (s, 1H). $^{13}$C NMR δ25.5, 27.9, 28.2, 28.6, 64.0, 79.6, 83.6, 120.6, 120.9, 121.0, 123.2, 123.5, 128.6, 128.9, 136.4, 142.3, 153.2, 153.7, 163.3. HRMS (FAB) m/z 366.201 (M+H)$^+$ ($C_{19}H_{28}N_4O_5$ requires 366.202).

EXAMPLE 117

3-(N-Acridinyl)-aminobromobenzene

To a solution of 3-(N-acridinyl)-aminobenzyl alcohol (1.45 g, 3.97 mmol) in 15 mL of $CH_2Cl_2$ were added N-bromosuccinimide (NBS) (0.78 g, 4.4 mmol) and $PPh_3$ (1.25 g, 4.76 mmol). The resulting solution was stirred at room temperature for 2 h and the solvent was evaporated. The residue was purified by flash chromatography on a silica gel column. Elution with 50:1 hexanes-EtOAc gave the title compound as a white foam: yield 1.21 g (71.6%).

$^1$H NMR δ1.51 (s, 9H), 1.54 (s, 9H), 4.47 (s, 2H), 7.14 (d, 1H, J=7.6 Hz), 7.32 (t, 1H, J==7.9 Hz), 7.58–7.64 (m, 2H), 10.37 (s, 1H), 11.63 (s, 1H). HRMS (FAB) m/z 428.117 (M+H)$^+$ ($C_{18}H_{27}BrN_3O_4$ requires 428.118). Anal. Calcd. for $C_{18}H_{26}BrN_3O_4$: C, 50.57; H, 6.14; N, 9.84. Found: C, 50.55; H, 6.12; N, 9.99.

EXAMPLE 118

3-(N-t-Boc)-aminobenzyl alcohol

A solution of 3-aminobenzyl alcohol (0.62 g, 5.0 mmol), di-tert-butyl dicarbonate (1.09 g, 5.0 mmol) and triethylamine (1.5 g, 15 mmol) in 20 mL of dry THF was stirred at room temperature for two days. The solvent was evaporated under vacuum. The residue was dissolved in a mixture of $CHCl_3$ and $H_2O$. The layers were separated and the aqueous phase was extracted with $CHCl_3$. The combined organic phase was washed with brine, dried ($Na_2SO_4$) and concentrated. The residue was purified by flash chromatography on a silica gel column. Elution with 200:1 $CH_2Cl_2$—MeOH gave the title compound as oil: yield 0.88 g (79.3%).

$^1$H NMR δ1.48 (s, 9H), 3.69 (t, 1H, J=5.0 Hz, ex $D_2O$), 4.49 (d, 2H, J=5.5 Hz), 6.92 (d, 1H, J=7.0 Hz), 7.10–7.26 (m, 3H). $^{13}$C NMR δ28.3, 64.6, 80.5, 117.1, 117.5, 121.3, 128.9, 138.6, 142.0, 153.3. HRMS (FAB) m/z 223.129 (M+H)$^+$ ($CL_2Ha_8NO_3$ requires 223.128). Anal. Calcd. for $C_{12}H_{17}NO_3$: C, 64.54; H, 7.68; N, 6.28. Found: C, 64.31; H, 7.59; N, 6.37.

EXAMPLE 119

3-(N-t-Boc)-aminobromobenzene

To a solution of 3-(N-t-Boc)-aminobenzyl alcohol (8.25 g, 37 mmol) in 145 mL of $CH_2Cl_2$ were added $PPh_3$ (11.64 g, 44.4 mmol) and NBS (7.24 g, 41 mmol). The resulting solution was stirred at room temperature for two h. The solvent was evaporated under vacuum. The residue was purified by flash chromatography on a silica gel column. Elution with 50:1 hexanes-EtOAc gave compound the title compound as a white solid: yield 6.8 g (64.5%).

$^1$H NMR δ1.52 (s, 9H), 4.42 (s, 2H), 6.77 (s, 1H), 7.04–7.07 (m, 1H), 7.20–7.25 (m, 2H), 7.51(s, 1H). $^{13}$C NMR δ28.4, 33.5, 80.8, 118.9, 123.9, 129.7, 138.7, 152.8; HRMS (FAs) m/z 308.027 (M+Na)$^+$($C_{12}HL_6BrNo_2Na$ requires 308.026). Anal. Calcd. for $C_{12}H_{16}BrNO_2$: C, 50.52; H, 5.66; N, 4.91. Found: C, 50.30; H, 5.49; N, 4.74.

EXAMPLE 120

Bis-Boc-guanidinyl piperazine

A mixture of piperazine (34.46 g, 0.4 mol), 1,3-bis(tert-butoxy carbonyl)-2-methyl-2-thiopseudourea (Aldrich) (29.0 g, 0.1 mol) in 260 mL of DMF was stirred at 50–60° C. for 2 h. The solvent was evaporated to dryness and the residue was dissolved in water-chloroform. The organic phase was separated and the aqueous phase was extracted with chloroform. The combined organic phase was washed with brine, dried ($Na_2SO_4$) and concentrated. The residue was purified by flash chromatography on silica gel using 1:2 hexanes-EtOAc, and then 1:1 EtOAc—MeOH as eluents to afford 27.2 g (83%) of the title compound as a white solid; silica gel TLC $R_f$ 0.34 (100% MeOH).

$^1$H NMR δ1.42 (s, 18H), 2.78–2.91 {m, 4H), 3.40–3.66 (m, 4H). HRMS (FAB) m/z 329.218 (M+H)$^+$($C_{15}H_{29}N_4O_4$ requires 329.218). Anal. Calcd. for $C_{15}H_{28}N_4O_4$: C, 54.86; H, 8.58; N, 17.06. Found: C, 54.87; H, 8.48; N, 17.20.

EXAMPLE 121

N—Bromoacetyl-N(bis-Boc-guanidinyl)piperazine

A solution of bromoacetyl bromide (2.06 g, 10.2 mmol) in 20 mL of THF was added dropwise to a stirred solution of bis-Boc-guanidinyl piperazine (3.28 g, 10 mmol) and diisopropylethylamine (2.1 mL, 1.56 g, 12 mmol) in 50 mL of THF at −30° C. The cooling bath was removed and the reaction mixture was stirred for 1.5 h. After the solvent was evaporated, the residue was dissolved in chloroform. This solution was washed with water, brine, dried ($Na_2SO_4$) and concentrated. The residue was purified by flash chromatography on silica gel column. Elution with 5:1, 2:1 and then 1:1 hexanes-EtOAc afforded 3.5 g (78%) of the title compound as a white solid.

Silica gel TLC Rf 0.45 (1:2 hexanes-EtOAc). $^1$H NMR δ1.46 (sg 18H), 3.48–3.75 (m, 8H), 3.85 (s, 2H); HRMS (FAB) m/z 449.141 (M+H)$^+$($CL_{17}H_{30}BrN_4O_5$ requires 449.140). Anal. Calcd. for $C_{17}H_{29}BrN_4O_5$: C, 45.44; H, 6.49; N, 12.46. Found: C,45.54; H, 6.25; N, 12.66.

EXAMPLE 122

N-(4Chloromethylbenzoyl)-N(bis-Boc-guanidinyl) piperazine

A solution of chloroacetyl chloride (1.77 g, 15.6 mmol) in 20 mL of THF was added to a stirred solution of compound bis-Boc-guanidinyl piperazine (4.93 g, 15 mmol) and diisopropylethyl amine (3.2 mL, 2.34 g, 18 mmol) in 80 mL of THF at 0° C. The resulted reaction mixture was allowed to warmed to rt and stirred for 2 h. The solvent was evaporated and the residue was dissolved in chloroform. The chloroform solution was washed with water, dried ($Na_2SO_4$), and concentrated. The residue was purified by flash chromatography on a silica gel column. Elution with 5:1, 2:1 and then 1:1 hexanes-EtOAc afforded 5.76 g of the title compound as a white solid, yield 95%.

Silica gel TLC $R_f$ 0.48 (1:2 hexanes-EtOAc); $^1$H NMR δ1.38 (s, 18H), 3.40–3.66 (m, 8H), 4.00 (s, 2H), 10.00 (br, 1H). HRMS (FAB) m/z 537.086 (M+Cs)$^+$ ($C_{17}H_{29}ClN_4O_5Cs$ requires 537.088). Anal. Calcd. for $C_{17}H_{29}ClN_4O_5$: C, 50.43; H, 7.21; N, 13.83. Found: C, 50.56; H, 7.12; N, 14.00.

EXAMPLE 123

N-(3-chloromethylbenzoyl)-N(bis-Boc-guanidinyl) piperazine

The title compound was prepared as described above for compound N-(4-chloromethylbenzoyl)-N(bis-Boc-guanidinyl)piperazine from bis-Boc-guanidinyl piperazine (3.28 g, 10 mmol), 3-(chloromethyl)benzyl chloride (1.94 g, 10.26 mmol), and diisopropylethyl amine (2.1 mL, 1.56 g, 12 mmol) in 70 mL of THF. Flash chromatographic purification afforded 4.33 g of the title compound as a white solid, yield 90%

Silica gel TLC $R_f$ 0.42 (1:1 hexanes-EtOAc). $^1$H NMR $\delta$1.37 (s, 18H), 3.28–3.85 (m, 8H), 4.48 (s, 2H), 7.20–7.40 (m, 4H), 10.10 (s, 1H). MS (FAB) m/z 503 (M+Na)$^+$. HRMS (FAB) m/z 481.222 (M+H)$^+$ ($C_{23}H_{34}ClN_4O$. requires 481.221). Anal. Calcd. for $C_{23}H_{33}ClN_4O_5$: C, 57.43; H, 6.90; N, 11.64. Found: C, 57.33; H, 6.72; N, 11.86.

EXAMPLE 124

N-(4-chloromethylbenzoyl)-N(bis-Boc-guanidinyl) piperazine

The title compound was prepared as described above for compound N-(4-Chloromethylbenzoyl)-N(bis-Boc-guanidinyl)piperazine 63B from bis-Boc-guanidinyl piperazine (6.56 g, 20 mmol), 4-(chloromethyl)benzyl chloride (3.88 g, 20 mmol), and diisopropylethyl amine (4.2 mL, 3.1 g, 24 mmol) in 150 mL of THF. Flash chromatographic purification afforded 9.5 g of the title compound as a white solid, yield 98%.

Silica gel TLC $R_f$ 0.38 (1:1 hexanes-EtOAc). $^1$H NMR $\delta$1.36 (s, 18H), 3.25–3.80 (m, 8H), 4.48 (s, 2H), 7.25–7.37 (m, 4H), 10.05 (br, 1H). MS (FAB) m/z 503 (M+Na)$^+$. HRMS (FAB) m/z 481.220 (M+H)$^+$ ($C_{23}H_{34}ClN_4O_5$ requires 481.221). Anal. Calcd. for $C_{23}H_{33}ClN_4O_5$: C, 57.43; H, 6.90; N, 11.64. Found: C, 57.30; H, 7.08; N, 11.40.

EXAMPLE 125

N-Boc-N-bromoacetyl-piperazine

The title compound was prepared as described above for N-bromoacetyl-N(bis-Boc-guanidinyl)piperazine from N-Boc-piperazine (prepared as per the procedure of Carpino, L.A., et al., *J. Org. Chem.*, 1983, 48, 661–665) (23.0 g, 123 mmol), bromoacetyl bromide (25.0 g, 123 mmol), and diisopropyletyhl amine (21 mL, 156 g, 120 mmol) in 240 mL of $CH_2Cl_2$. Flash chromatographic purification afforded 25.0 g of the title compound as pale yellow crystals, yield 66%.

Silica gel TLC $R_f$ 0.34 (1:1 hexanes-EtOAc). $^1$H NMR $\delta$1.37 (s, 9H), 3.30–3.56 (m, 8H), 3.80 (s, 2H). $^{13}$C NMR $\delta$25.8, 28.2, 28.5, 41.9, 43.2, 46.5, 80.3, 154.4, 165.4. MS (FAB) m/z 331 (M+Na)$^+$. HRMS (FAB) m/z 307.066 (M+H)$^+$ ($C_{11}H_{20}BrN_2O_3$ requires 307.065). Anal. Calcd. for C:LHlgBrN$_2$O$_3$: C, 43.01; H, 6.22; N, 9.12. Found: C, 43.24; H, 6.22; N, 9.37.

EXAMPLE 126

N-Boc-N-chloroacetyl-piperazine

The title compound was prepared as described above for compound N-(4-chloromethylbenzoyl)-N(bis-Boc-guanidinyl)piperazine from N-Boc-piperazine (prepared as per the procedure of Carpino, L. A., ibid.) (9.32 g, 50 mmol), chloroacetyl chloride (5.67 g, 50.2 mmol), and diisopropylethyl amine (10.5 mL, 7.79 g, 60 mmol) in 200 mL of THF. Flash chromatographic purification afforded 12.14 g of the title compound as a white solid, yield 92%.

Silica gel TLC $R_f$ 0.50 (1:2 hexanes-EtOAc). $^1$H NMR $\delta$1.39 (s, 9H), 3.30–3.56 (m, 8H), 4.02 (s, 2H). $^{13}$C NMR $\delta$28.3, 40.8, 41.9, 43.1, 43.4, 46.1, 80.4, 154.4, 165.3. MS (FAB) m/z 263 (M+H)$^+$. HRMS (FAB) m/z 285.098 (M+Na)$^+$ ($C_{21}H_{19}ClN_2O_3Na$ requires 285.098). Anal. Calcd. for $C_{119}ClN_2O_3$: C, 50.29; H, 7.28; N, 10.66. Found: C, 50.10; H, 7.21; N, 10.90.

EXAMPLE 127

N-Boc-N-(3-chloromethyl-phenylcarbony)-piperazine

The title compound was prepared as described above for N-(4-chloromethylbenzoyl)-N(bis-Boc-guanidinyl)piperazine from N-Boc-piperazine (prepared as per the procedure of Carpino, L. A., ibid.) (3.82 g, 20.5 mmol), 4-(chloromethyl)benzyl chloride (3.88 g, 20 mmol), and diisopropylethyl amine (3.92 mL, 2.91 g, 22.5 mmol) in 60 ML of THF. Flash chromatographic purification afforded 6.4 g of the title compound as a white solid, yield 94%.

Silica gel TLC $R_f$ 0.45 (1:1 hexanes-EtOAc). $^1$H NMR $\delta$1.44 (s, 18H), 3.25–3.70 (m, 8H), 4.57 (s, 2H), 7.30–7.48 (m, 4H); MS (FAB) m/z 361 (M+Na)$^+$. HRMS (FAB) m/z 339.146 (M+H)$^+$ ($C_{37}H_{24}ClN_2O_3$ requires 339.147). Anal. Calcd. for $C_{17}H_{23}ClN_2O_3$: C, 60.26; H, 6.83; N, 8.26. Found: C, 60.10; H, 6.88; N, 7.99.

EXAMPLE 128

N'-(tert-Butoxycarbonyl)-N"-($\alpha$-chloro)acetamide

A solution of chloroacetylchloride (2.82 g, 25 mmol) in 50 mL of dry THF was added dropwise to the solution of mono-(tert-butoxy carbonyl)ethylenediamine (prepared as per the procedure of Demonchaux, P., et al., *Eur. J. Med. Chem.*, 1991, 26, 915–920) (4.0 g, 25 mmol) and diisopropylethyl amine (3.15 g, 27.5 mmol) in 100 mL of dry THF at $-10°$ C. The resulting solution was stirred at $-10°$ C. for 30 min, and the solvent was evaporated under vacuum. The residue was dissolved in a mixture of $CHCl_3$ and $H_2O$. The phases were separated and the aqueous phase was extracted with $CHCl_3$. The combined organic phase was washed with brine, dried ($Na_2SO_4$), concentrated. The residue was recrystallized from 1:3 EtOAc-hexanes to give the title compound as white crystals: yield 5.47 g (92.7%).

$^1$H NMR $\delta$1.44 (s, 9H), 3.29–3.44 (m, 4H), 4.03 (s, 2H), 4.92 (b, 1H), 7.21 (br, 1H). $^{13}$C NMR $\delta$28.5, 39.7, 41.0, 42.5, 79.7, 156.8, 166.9. HRMS (FAB) m/z 237.101 (M+H)$^+$ ($C_9H_{18}ClN_2O_3$ requires 237.100). Anal. Calcd. for $C_9H_{17}ClN_2O_3$: C, 45.75; H, 7.26; N, 11.86. Found: C, 46.00; H, 7.32; N, 12.04.

EXAMPLE 129

2-Bromomethyl Pyridine-6-methanol

To a solution of 2,6-pyridinedimethanol (4.17 g, 30 mmol) were added $PPh_3$ (S.24 g, 20 mmol) and NBS (3.56 g, 20 mmol). The resulting solution was stirred at room temperature for 1 h. The solvent was evaporated, and the residue was purified by flash chromatography on a silica gel column. Elution with 2:1 hexanes-EtOAc gave product 72 which was further purified by recrystallization from 1:5 CHCl$_3$-hexanes to give white crystals: yield 1.61 g (40%).

$^1$H NMR spectrum is consistent with that reported. (Newcomb, M.; Gokel, G. w.; Cram, D. J. J. Am. Chem. Soc. 1974, 96, 6810).

EXAMPLE 130

N'-(tert-Butoxy carbonyl)-N"-p-(chloromethyl) benzoyl ethylene diamine

The title compound was synthesized as above for N-Boc-N-(3-chloromethyl-phenylcarbony)-piperazine from mono- (tert-butoxy carbonyl)ethylenediamine (4.1 g 25.7 mmol), 4-(chloromethyl)benzoyl chloride (5.0 g, 25.7 mmol) and diisopropylethyl amine (9.96 g, 77.1 mmol). The crude material was purified by flash chromatography on a silica gel column to give the title compound as a white solid: yield 7.52 g (93.5%).

$^1$H NMR δ1.43 (s, 9H), 3.34–3.42 (m, 2H), 3.49-3.56 (m, 2H), 4.58 (s, 2H), 5.19(br, 1H), 7.38–7.42 (m, 3H), 7.78–7.82 (m, 2H). $^{13}$C NMR b 27.9, 28.2, 28.5, 28.8, 40.0, 42.0, 45.5, 79.9, 127.6, 128.5, 128.76, 134.2, 140.7, 157.6, 167.4. HRMS (FAB) m/z 313.133 (M+H)$^+$ ($C_{15}H_{22}ClN_2O_3$ requires 313.131). Anal. Calcd. for $C_{15}H_{21}ClN_2O_3$: C, 57.67; H, 6.78; N, 8.97. Found: C, 57.47; H, 6.74; N, 8.93.

EXAMPLE 131

N-Boc-N-(4-chloromethyl-phenylcarbony)-piperazine

The title compound was prepared as described above for compound N-(4-chloromethylbenzoyl)-N(bis-Boc-guanidinyl)piperazine from N-Boc-piperazine (prepared as per the procedure of Carpino, L. A., ibid.) (3.15 g, 16.9 mmol), 3-(chloromethyl)benzoyl chloride (3.1 g, 16.3 mmol), and diisopropylethyl amine (4 mL, 2.96 g, 22.9 mmol) in 60 mL of THF. Flash chromatographic purification afforded 5.5 g (99%) of the title compound as a white solid.

Silica gel TLC Rf 0.47 (1:1 hexanes-EtOAc). $^1$H NMR δ1.40 (s, 9H), 3.25–3.70 (m, 8H), 4.52 (s, 2H), 7.24– 7.41 (m, 4H). MS (FAB) m/z 361 (M+Na)$^+$. HRMS (FAB) m/z 339.148 (M+H)$^+$ ($C_{17}H_{24}ClN_2O_3$ requires 339.147). Anal. Calcd. for $C_{17}H_{24}ClN_2O_3$: C, 60.26; H, 6.83; N, 8.26. Found: C, 60.12; H, 6.66; N, 8.37.

EXAMPLE 132

N-Boc-N"-chloromethylphenylcarbonyl-1,2-diaminoethane

A solution of mono-(tert-butoxy carbonyl) ethylenediamine (prepared as per the procedure of Demonchaux, P., et al., *Eur. J. Med. Chem.*, 1991, 26, 915–920) (1.6 g, 10 mmol) in 15 mL of dry THF was added dropwise to a solution of 3-(chloromethyl)benzoyl chloride (1.89 g, 10 mmol) and diisopropylethyl amine in 35 mL of dry THF at 0° C. The resulting solution was stirred at 0° C. for 20 min, and the solvent was evaporated under vacuum. The residue was dissolved in $CHCl_3$. The solution was washed with $H_2O$, dried ($Na_2SO_4$), and concentrated. The residue was purified by flash chromatography on a silica gel column. Elution with 100:1 $CH_2Cl2$-MeOH gave the title compound as a white solid: yield 1.55 g (49.5%).

$^1$H NMR ($CDCl_3$) δ1.41 (s, 9H), 3.34–3.41 (m, 2H), 3.49–3.54 (m, 2H), 4.56 (s, 2H), 5.21 (br, 1H), 7.37–7.41 (m, 1H), 7.47–7.51 (m, 2H), 7.73–7.77 (m, 1H), 7.83 (s, 1H). $^{13}$C NMR ($CDCl_3$) δ28.2, 28.5, 39.9, 42.1, 45.7, 80.0, 127.1, 127.4, 129.2, 131.4, 134.7, 137.9, 157.7, 167.4. HRMS (FAB) m/z 313.131 (M+H)$^+$ ($C_{15}H_{22}ClN_2O_3$requires 313.131). Anal. Calcd. for $C_{15}H_{21}ClN_2O_3$: C, 57.67; H, 6.78; N, 8.97. Found: C, 57.68; H, 6.89; N, 9.01.

EXAMPLE 133

Preparation of Libraries 57, 58 and 59

A solution of six functional groups selected having bromide and chloride functionalities (0.68 mmol each, in a total of 4.08 mmol, 4.08 equiv, 1.02 equiv per reactive site) in 30 mL of anhydrous acetonitrile was added to a stirred mixture of compound 7 FIG. 2 (238 mg, 1.0 mmol) and anhydrous potassium carbonate (3.0 g) in 4 mL of DMF and 10 mL of acetonitrile. The resulting reaction mixture was stirred at room temperature for 2 h (at 50–60 ° C./8 h for library 59), and aminomethylated polystyrene resin (0.5 g, 0.49 mmol) was added. After stirring for 1 h, the solvent was evaporated, and the residue was dissolved in a mixture of chloroform-water. The organic phase was separated, and the aqueous phase was extracted with chloroform. The combined organic phase was washed with brine, dried ($Na_2SO_4$), and concentrated. The residue was passed through a short silica gel column using 1:2 hexanes-EtOAc, 100w EtOAc, and then 100%. MeOH as eluents. The library thus obtained, after evaporation of the solvent, was dissolved in 8 mL of chloroform and treated with TFA (12 mL) at room temperature for 3 h. The reaction mixture was concentrated, and the residue was dissolved in HCl(g) saturated methanol. The solution was concentrated under vacuum to give hydrochloride salt of libraries as pale yellow oils, yields, 87–92%. Library 57 was prepared from: 3-(N-acridinyl) aminobromobenzene, Example 117; N-Boc-N-bromoacetyl-piperazine, Example 125; 2-Bromomethyl Pyridine-6-methanol, Example 129; 1,3-propanesulfone (Aldrich); methyl-2-chloro-4-trifluoromethyl pyrimidine-5-carboxylate (Maybridge); t-butylbromoacetate (Aldrich).

Library 58 was prepared from: N-bromoacetyl-N(bis-Boc-guanidinyl)piperazine, Example 121; 3-(N-t-Boc)-aminobromobenzene, Example 119; p-trifluoromethyl benzylbromide (Aldrich); 4-bromomethyl-3-nitrobenzoic acid (Aldrich); ethyl-6-chloro-5-cyano-2-trifluoromethyl-pyridine-3-carboxylate (Maybridge); 2-Bromo-N-(2'-ethyl-N'-tert-butoxycarbonylamino)-acetamide, Example 145.

Library 59 was prepared from: N-(3-chloro-methylbenzoyl)-N(bis-Boc-guanidinyl)piperazine, Example 123; N'-Boc-N"-(α-chloro)acetamide, Example 128; 1-Boc-2-chloromethylbenzimidazole, Example 143; 2-chloropyrimidine (Aldrich); diethyl chloromethyl-phosphonate; 3-chloromethyl-1,2,3-oxadiazole (Maybridge).

Library 57 was assayed in procedures to determine the minimum inhibitory concentration. The activity in the *S. pyogenes* procedure was 42 μM (94% inhibition).

The activity of Library 58 in the S. pyogenes procedure was 42 μM (95% inhibition). The activity in the E. coli procedure was 20 μM (86% inhibition). The activity in the Tat/tar assay was 100 μM (138% inhibition).

EXAMPLE 134

2-[(N-o-nitrosulfonyl-N-acetamide)-aminomethyl]-6-{[N1-methyl-N1-o-nitrosulfonyl)-N2-(Boc)-N2-1-propanol]-1,2-diaminoethane}pyridine A mixture of triprotected 2-[(N-o-nitrosulfonyl)-aminometyhl]-6-{[N1-methyl-N1-o-nitrosulfonyl)-N2-(Boc)1-propanol]-1,2-diaminoethane}pyridine (1.06 g, 1.5 mmol), bromoacetamide (227 mg, 1.65 mmol, 1.1 equiv), and potassium carbonate (1.5 g) in 20 mL of acetonitrile was stirred at room temperature overnight. The solvent was evaporated and the residue was dissolved in water-chloroform. The layers were separated, and the aqueous phase was extracted with chloroform. The combined organic phase was washed with brine, dried ($Na_2SO_4$) and concentrated. The residue was purified by flash chromatography on a silica gel column. Elution with 100% EtOAc and then 3:1 EtOAc—MeOH gave 0.93 g (81%) of the title compound as a white foam.

Silica gel TLC $R_f$ 0.51 (10:1 EtOAc—MeOH). $^1$H NMR (CDCl$_3$) δ1.38 (s, 9H), 1.48–1.72 (m, 2H), 3.08–3.27 (m, 4H), 3.40–3.62 (m, 4H), 4.14 (s, 2H), 4.56 (s, 2H), 4.61 (s, 2H), 7.10–7.30 (m, 3H), 7.58–7.78 (m, 6H), 7.90–8.06 (m, 2H). HRMS (FAB) m/z 898.117 (M+Cs)$_+$ (C$_{31}$H$_{39}$N$_7$S$_2$O$_{12}$Cs requires 898.115).

EXAMPLE 135

2-(N-acetamide-aninomethyl)-6-{[N1-methyl)-N2-(Boc)-N2-1-propanol]-1,2-diaminoethane}pyridine A mixture of compound 2-[(N-o-nitrosulfonyl-N-acetamide)-aminomethyl]-6-{[N1-methyl-N1-o-nitrosulfonyl)-N2-(Boc)-N2-1-propanol]-1,2-diaminoethane}pyridine (0.90 g, 1.17 mmol), potassium carbonate (1.5 g) and thiophenol (290 μL, 311 mg, 2.82 mmol) in 30 mL of DMF was stirred at room temperature overnight. The solvent was evaporated, and the residue was dissolved in water-chloroform. The layers were separated, and the aqueous phase was extracted with chloroform. The combined organic phase was washed with brine, dried (Na$_2$SO$_4$), and concentrated. The residue was purified by flash chromatography on a silica gel column. Elution with 100% EtOAc, 100:1 and then 20:1 MeOH-30% NH$_4$OH gave 123 mg (27%) of the title compound as a pale yellow oil.

Silica gel TLC $R_f$ 0.49 (100:1 MeOH-30% NH$_4$OH). $^1$H NMR (CDCl$_3$) δ1.38 (s, 9H), 1.56–1.75 (m, 2H), 2.72–2.88 (m, 2H), 3.20–3.60 (m, 8H), 3.84 (s, 2H), 3.87 (s, 2H), 6.45 (br, 2H), 7.02 –7.20 (m, 2H), 7.55 (t, 1H, J=7.7 Hz). MS (FAB) m/z 396 (M+H )$^+$. HRMS (FAB) m/z 418.244 (M+Na)$^+$ (C$_{19}$H$_{33}$NSO$_3$Na requires 418.243).

EXAMPLE 136

2-t(N-m-trifluoromethylbenzyl-N-acetamide)-aminomethyl]-6-{[N1-methyl-N1-m-trifluoromethylbenzyl)-N2-(Boc)-N2-1-propanol]-1,2-diaminoethane}pyridine The title compound was prepared as described above for 2-[(N-o-nitrosulfonyl-N-acetamide)-aminomethyl]-6-{[N1-methyl-N1-o-nitrosulfonyl)-N2-(Boc)-N2-1-propanol]-1,2-diaminoethane}pyridine from 2-(N-acetamide-aminomethyl)-6-{[N1-methyl)-N2-(Boc)-N2-1-propanol]-1,2-diaminoethane}pyridine (120 mg, 0.303 mmol), potassium carbonate (1.0 g) and α,α,α,-trifluoro-α'-bromo-m-xylene (112 μL, 173 mg, 0.72 mmol, 2.39 equiv) in 5 mL of acetonitrile. Flash chromatographic purification using 1:1 hexanes-EtOAc and then 5:1 EtOAc—MeOH as eluents afforded 199 mg (92%) of the title compound as a pale yellow oil.

Silica gel TLC $R_f$ 0.53 (5:1 EtOAc—MeOH). $^1$H NMR (CDCl$_3$) δ1.25 (s, 9H), 1.40–1.70 (m, 2H), 2.56–2.72 (m, 2H), 3.10–3.35 (m, 6H), 3.40–3.55 (m, 2H), 3.69 (s, 4H), 3.75 (s, 2H), 3.78 (s, 2H), 6.48 (br, 1H), 6.99 –7.10 (m, 1H), 7.30–7.68 (m, 9H), 8.20–8.45 (m, 1H). MS (FAB) m/z 712 (M+H )$^+$. HRMS (FAB) m/z 844.228 (M+Cs)4 (C$_{35}$H$_{43}$N$_5$O$_4$F$_6$Cs requires 844.227).

EXAMPLE 137

2-[(N-n-trifluoromethylbenzyl-N-acetamide)-aminomethyl]-6-{[N1-methyl-N1-m-trifluoromaethylbenzyl)-N2-1-propanol]-1,2-diaminoethane}pyridine TFA (5 mL) was added to a solution of compound 2-[(N-m-trifluoromethylbenzyl-N-acetamide)-aminomethyl]-6-{[N1-methyl-N1-m-trifluoromethylbenzyl)-N2-(Boc)-N2-1-propanol]-1,2-diaminoethane}pyridine (190 mg, 0.267 mmol) in 1 mL of chloroform at 0° C. The mixture was stirred at room temperature for 4 h, concentrated, and dissolved in aqueous potassium carbonate solution-chloroform. The layers were separated, and the aqueous phase was extracted with chloroform. The combined organic phase was washed with brine, dried (Na$_2$SO$_4$), and concentrated. Preparative thin layer chromatographic purification using 150:1 MeOH-30% NH$_4$OH as developing agent gave 80 mg (53%) of the title compound as a pale yellow oil.

Silica gel TLC $R_f$ 0.56 (50:1 MeOH-30% NH$_4$OH). $^1$H NMR (CDCl$_3$) δ1.50–1.75 (m, 2H), 2.60–2.85 (m, 6H), 3.23 (s, 2H), 3.55–3.82 (m, 8H), 3.95–4.20 (m, 2H), 6.38 (br, 2H), 6.99–7.65 (m, 1H), 8.25 (br, 1H). $^{13}$C NMR (CDCl$_3$) δ30.4, 46.8, 48.9, 53.2, 57.6, 58.6, 58.8, 60.3, 60.4, 62.9, 121.7, 122.0, 124.0, 124.2, 125.4, 128.2, 128.9, 130.4, 131.0, 132.1, 137.2, 139.2, 140.2, 157.4, 159.2, 174.4. MS (FAB) m/z 744 (M+Cs)$^+$. HRMS (FAB) m/z 612.274 (M+H)$^+$ (C$_3$OH$_{36}$N$_5$O$_2$F$_6$ requires 612.277).

The title compound was assayed in the *S. pyogenes* procedure and the activity was: 100 μM, 95% inhibition. The activity found in the E. coli procedure was: 100 μM, 87% inhibition.

EXAMPLE 138

2-(bio-Boc-guanidinyl)methyl-6-{[N1-methyl-N1-o-nitrosulfonyl-N2-Boc-N2-1-propanol]-1,2-diaminoethane}pyridine A solution of 2-aminomethyl-6-{[N1-methyl-N1-o-nitrosulfonyl-N2-Boc-N2-1-propanol]-1,2-diaminoethane}-pyridine (1.35 g, 2.57 mmol) and 1,3-bis(t-butoxycarbonyl)-2-methyl-2-thiopseudourea (1.53 g, 5.26 mmol, 2.0 equiv) in 20 mL of DMF was stirred at 50–60° C. for 3 h, and room temperature overnight. The solvent was evaporated, and the residue was dissolved in water-chloroform. The layers were separated, and the aqueous phase was extracted with chloroform. The combined organic phase was washed with brine, dried (Na$_2$SO$_4$), and concentrated. The residue was purified by flash chromatography on a silica gel column. Elution with 10:1, 1:1 and then 0:1 hexanes-EtOAc afforded 0.98 g (50%) of the title compound as a white foam.

Silica gel TLC $R_f$ 0.51 (1:4 hexanes-EtOAc). $^1$H NMR (CDCl$_3$) δ1.30–1.75 (m, 29H), 3.20–3.70 (m, 8H), 4.60, 4.62 (s, 2H), 4.69 (s, 2H), 7.10–7.30 (m, 3H), 7.47–7.70 (m, 3H), 7.90 (d, 1H, J=7.2 Hz), 9.20 (br, 1H), 11.52 (br, 1H). $^{13}$C NMR (CDCl$_3$) δ28.1, 28.3, 30.4, 42.9, 45.4, 45.7, 46.9, 53.1, 58.2, 79.5, 80.7, 83.1, 120.8, 121.4, 124.0, 125.3, 128.2, 129.0, 130.7, 131.5, 133.5, 137.7, 148.0, 153.0, 155.4, 155.6, 156.0, 156.6, 163.5. HRMS (FAB) m/z 898.243 (M+Cs)$^+$ (C$_{34}$H$_{51}$N$_7$O$_{11}$SCs requires 898.242). Anal. Calcd. for C$_{34}$H$_{51}$,N$_7$O,S: C, 53.32; H, 6.70; N, 12.80. Found: C, 53.42; H, 6.66; N, 12.57.

EXAMPLE 139

2-(bis-Boc-guanidinyl)methyl-6-{[N1-methyl-N2-Boc-N2-1-propanol]-1,2-diaminoethane}pyridine The title compound was prepared as described above for 2-(N-acetamide-aminomethyl)-6-{[N1-methyl)-N2-(Boc)-N2-1-propanol]-1,2-diaminoethane}pyridine from 2-aminomethyl-6-{[N1-methyl-N1-o-nitrosulfonyl-N2-Boc-N2-1-propanol]1,2-diaminoethane}pyridine (0.87 g, 1.13 mmol), potassium carbonate (1.5 g), and thiophenol (200 µL, 215 mg, 1.9 mmol, 1.7 equiv) in 20 mL of DMF. Flash chromatographic purification using 100% EtOAc, 10:1 and then 5:1 EtOAc—MeOH as eluents afforded 655 mg (99w) of product 12 as a light yellow oil.

Silica gel TLC $R_f$ 0.50 (2:1 EtOAc—MeOH. $^1$H NMR (CDCl$_3$) δ1.37 (s, 9H), 1.48 (s, 18H), 1.55–1.70 (m, 2H), 2.70–2.88 (m, 2H), 3.15–3.60 (m, 6H), 3.89 (s, 2H), 4.68 (s, 1H), 4.70 (s, 1H), 7.07 (t, 2H, J=7.8 Hz), 7.57 (m, 1H, J=7.8 Hz), 9.70 (br, 1H), 11.49 (br, 1H). $^{13}$C NMR (CDCl$_3$) δ28.1, 28.3, 30.7, 43.6, 45.6, 47.6, 47.9, 54.1, 58.3, 79.3, 79.9, 82.9, 119.8, 120.7, 137.2, 153.1, 154.6, 155.7, 158.4, 163.5. MS (FAB) m/z 581 (M+H)$^+$. HRMS (FAB) m/z 713.262 (M+Cs)$^+$ (C$_{28}$H$_{48}$N$_6$O$_7$Cs requires 713.263). Anal. Calcd. for C$_{28}$H$_{48}$N6O$_7$: C, 57.91; H, 8.32; N, 14.47. Found: C, 57.67; H, 7.99; N, 14.61.

EXAMPLE 140

2-(bis-Boc-guanidinyl)methyl-6-{[N1-methyl-N2-Boc-N2-1-propanol]-1,2-diaminoethane}pyridine The title compound was prepared as described above for 2-[(N-m-trifluoromethylbenzyl-N-acetamide)-aminomethyl]-6-{[N1-methyl-N1-m-trifluoromethylbenzyl)-N2-1-propanol]-1,2-diaminoethane}pyridine from 2-(bis-Boc-guanidinyl)methyl-6-{[N1-methyl-N2-Boc-N2-1-propanol]-1,2-diaminoethane}pyridine (110 mg, 0.189 mmol) and 5 mL of TFA. The solvent was evaporated under reduced pressure, and the residue was dissolved in HCl (g) saturated methanol. The solution was concentrated under vacuum to afford 85 mg (97%) hydrochloride salt of the title compound as a white solid.

$^1$H NMR (D$_2$O) δ1.90–2.10 (m, 2H), 3.20–3.37 (m, 4H), 3.65 (s, 1H), 3.60–3.78 (m, 4H), 4.58 (s, 2H), 4.66 (s, 2H), 7.50 (t, 2H, J=7.8 Hz), 7.96 (t, 1H, J=7.8 Hz). MS (FAB) m/z 303 (M+Na)$^+$. HRMS (FAB) m/z 281.209 (M+H)$^+$ (C$_{13}$H$_{25}$N$_6$O requires 281.209).

EXAMPLE 141

2-(bia-Boc-guanidinyl)methyl-6-{[N1-methyl-N1-m-trifluoromethylbenzyl-N2-Boc-N2-1-propanol]-1,2-diaminoethane}pyridine The title compound was prepared as described above for 2-[(N-m-trifluoromethylbenzyl-N-acetamide)aminomethyl]-6-{[N-methyl-N1-m-trifluoromethylbenzyl]-N2-(Boc)-N2-1-propanol)-1,2-diaminoethane}pyridine from 2-(bis-Boc-guanidinyl)methyl-6-{[N1-methyl-N2-Boc-N2-1-propanol]-1,2-diaminoethane}pyridine (0.53 g, 0.91 mmol), potassium carbonate (1.5 g), and α,α,α,-trifluoro-α'-bromo-m-xylene (155 µL, 240 mg, 1.0 mmol, 1.1 equiv) in 10 mL of acetonitrile. Flash chromatographic purification using 5:1 and then 1:2 hexanes-EtOAc as eluents afforded 580 mg (86%) of the title compound as a colorless oil.

Silica gel TLC $R_f$ 0.30 (1:1 hexanes-EtOAc). $^1$H NMR (CDCl$_3$) δ1.19 (s, 9H), 1.37 (s, 9H), 1.40 (s, 9H), 1.40–1.60 (m, 2H), 2.50–2.65 (m, 2H), 3.00–3.48 (m, 6H), 3.69 (s, 2H), 3.75 (s, 2H), 4.62 (s, 1H), 4.64 (s, 1H), 6.98–7.02 (m, 1H), 7.20–7.60 (m, 6H), 9.38 (br, 1H), 11.46 (br, 1H). $^{13}$C NMR (CDCl$_3$) δ27.9, 28.2, 30.5, 43.2, 45.0, 45.8, 51.9, 58.2, 58.7, 60.0, 79.1, 79.8, 82.7, 119.9, 121.5, 123.8, 125.2, 126.9, 128.7, 130.2, 130.8, 131.9, 137.1, 140.6, 152.8, 154.8, 155.9, 156.6, 158.6, 163.5. MS (FAB) m/z 739 (M+H)$^+$. HRMS (FAB) m/z 871.296 (M+Cs)$^+$ (C$_{36}$H$_{53}$N$_6$O$_7$F$_3$Cs requires 871.298). Anal. Calcd. for C$_{36}$H$_{53}$N$_6$O$_7$F$_3$: C, 58.52; H, 7.22; N, 11.37. Found: C, 58.52; H, 6.93; N, 11.15.

EXAMPLE 142

2-(bis-Boc-guanidinyl)methyl-6-{[N1-methyl-N1-m-trifluoromethylbenzyl-N2-1-propanol]-1,2-diaminoethane}pyridine The title compound was prepared as described above for compound 2-[(N-m-trifluoromethylbenzyl-N-acetamide)-aminometyhl]-6-{[N1-methyl-N1-m-trifluoromethylbenzyl)-N2-1-propanol]-1,2-diaminoethane}-pyridine from 2-(bis-Boc-guanidinyl)methyl-6-{[N1-methyl-N1-m-trifluoromethylbenzyl-N2-Boc-N2-1-propanol]-1,2-diaminoethane}pyridine (540 mg, 0.73 mmol) and 8 mL of TFA. Flash chromatographic purification using 50:1 MeOH-30% NH$_4$OH as eluent afforded 150 mg (47%) of the title compound as a pale yellow oil.

Silica gel TLC $R_f$ 0.49 (50:1 MeOH-30% NH$_4$OH). $^1$H NMR (CDCl$_3$) δ1.45–1.70 (m, 2H), 2.54–2.78 (m, 6H), 3.58–3.82 (m, 6H), 4.25–4.70 (m, 2H), 7.00–7.70 (m, 7H). HRMS (FAB) m/z 439.244 (M+H)$^+$ (C$_{21}$H$_3$N6OF$_6$ requires 439.243).

The title compound was assayed in the below procedure for *S. pyogenes* and was found to have activity at 100 µM(95% inhibition).

EXAMPLE 143

1-Boc -2-chloramethylbenzimbidazole

A solution of di-t-butyldicarbonate (6.6 g, 30.0 mmol) in THF (50 mL) was added slowly to a stirred solution of 2-(chloromethyl)benzimidazole (5.0 g, 30 mmol) and triethylamine (5.0 mL, 36 mmol) in THF (150 mL) at 0° C. The reaction mixture was stirred at rt overnight. The solvent was evaporated, and the residue w as treated with CH$_2$Cl$_2$H$_2$O. The layers were separated and the aqueous phase was extracted with CH$_2$Cl$_2$. The combined organic phase was washed with brine, dried (Na and concentrated under high vacuum. The residue was purified by flash chromatography on silica gel using 3:8 and then 4:6 EtOAc-Hexanes to give 1.8 g (25%) of the title compound as a pale oil.

$^1$H NMR (CDCl$_3$) δ1.81 (s, 9H), 5.05 (s, 2H), 7.30–7.41 (m, 2H), 7.70–7.78 (m, 1H), 7.91–8.00 (m, 1H). $^{13}$C NMR δ24.0, 39.9, 86.4, 115.5, 120.2, 124.4, 125.9, 133.5, 142.0, 148.0, 150.1. HRS (FAB) m/z 267.090 (M+H)$^+$ (C$_{13}$H$_{16}$N$_2$O$_2$Cl requires 267.190).

EXAMPLE 144

N'-ethylenediamine-(bis-N-tert-butoxycarbonyl)-1-carboxamidine 1,3-Bis(tert-butoxycarbonyl)-2-methyl-2-thiopseudourea (11.62 g, 40.0 mmol) was dissolved in THF and added dropwise over 30 m in to a stirred solution of ethylenediamine (26.74 mL, 400 mmol) in 2% water (5 mL) and THF (255 mL) which was preequilibrated and maintained at 50° C. The reaction mixture was stirred at 50° C. for an additional 10 min until the absence of thiopseudourea by TLC. Prolonged reaction times resulted in degradation of the product. The solvent was evaporated in vacuo to give an oil which was dissolved in CHCl$_3$ and washed with saturated NaHCO$_3$ (×3). The organic layer was separated, dried with MgSO$_4$, and the solvent was evaporated in vacuo to give an oil. The oil was purified by flash chromatography using hexane:CH$_2$Cl$_2$:NEt$_3$ (20:80:1, v/v/v) to afford the title compound as a white solid (9.30 g, 77%).

$^1$H NMR (CDCl$_3$): δ11.5 (br, 1H), 8.66 (br, 1H), 3.62 (m, 2H), 3.48 (m, 2H), 2.90 (m, 2H), 1.50 (s, 18H). $^{13}$C NMR (CDCl$_3$): δ163.4, 156.2, 153.0, 82.9, 79.0, 43.2, 40.8, 28.3, 28.1. HRMS (ES+): M+H, calcd 303.2032, found 303.2039. Anal. Calcd. for C$_{13}$H$_{26}$N$_4$O$_4$: C, 51.64, H, 8.67, N, 18.53. Found: C, 51.44, H, 8.63, N, 18.13.

EXAMPLE 145

2-Bromo-N'-(2'-ethyl-bis-N-tert-butoxycarbonylguanidino)-acetamide

N'-ethylenediamine-(bis-N-tert-butoxycarbonyl)-1-carboxamidine (8.55 g, 28.3 mmol) was dissolved in CH$_2$Cl$_2$ (140 mL) and THF (140 mL) was added to give a solution. Pulverized NaHCO$_3$ (23.8 g, 283 mmol) was added to the mixture which was stirred for 5 min at ambient temperature then cooled to −500. Bromoacetylbromide (2.71 mL, 31.1 mmol) was added dropwise and the the reaction mixture was allowed to slowly warm to ambient temperature over several hours. The solvent was evaporated in vacuo to give a solid which was suspended in CH$_2$Cl$_1$. The suspension was washed with water (×3). The organic layer was separated, dried with MgSO$_4$, and the solvent evaporated in vacuo to give an oil. The oil was purified by flash chromatography using hexane:EtOAc (30:70, v/v) to give the title compound as a white foam (7.84 g, 65%).

$^1$H NMR (CDCl$_3$): δ11.45 (br, 1H), 8.65 (br, 1H), 8.20 (br, 1H), 3.85 (s, 2H), 3.60 (m, 2H), 3.45 (m, 2H), 1.50 (s, 18H). $^{13}$C NMR (CDCl$_3$): δ166.1, 162.6, 157.2, 152.7, 83.2, 79.2, 77.6, 77.0, 76.3, 41.7, 39.4, 28.5, 28.2, 27.8, 27.6. HRMS (ES+): M+Cs, calcd 555.0219/557, found 555.0231/557. M+H, calcd 423/425, found 423/425. Anal. Calcd for C$_{15}$H$_{27}$BrN$_4$O$_5$: C, 42.56; H, 6.43; N, 13.24. Found: C, 43.12, H, 6.24, N, 12.88.

EXAMPLE 146

2-Bromo-N-(2'-ethyl-N'-tert-butoxycarbonylamino)-acetamide

The title compound was synthesized as per the procedure of Arimoto, M., et al., J. Antibiot., 1986, 39, 1243–56. N-tert-butoxycarbonylethylenediamine (9.61 g, 60.0 mmol) was dissolved in CH$_2$Cl$_2$ (600 mL), diethylisopropylamine (12.54 mL, 72.0 mmol) was added, the reaction mixture was cooled to −50°, and bromoacetylbromide (5.75 mL, 66.0 mmol) was added slowly to give a dark solution which was allowed to slowly warm to ambient temperature. Water (100 mL) was added to the reaction mixture, and it was stirred for 10 min. The organic layer was separated, washed with water twice and brine, and the organic layer was separated, dried with MgSO$_4$, and the solvent was evaporated in vacuo to give an oil. The crude product was purified by flash chromatography using hexane:EtOAc (20:80, v/v) to afford a beige solid (7.13 g, 42%).

$^1$H NMR (CDCl$_3$): δ7.1 (br, 1H), 4.86 (br, 1H), 3.86 (s, 2H), 3.36 (m, 4H), 1.44 (s, 9H). $^{13}$C NMR (CDCl$_3$): δ166.4, 156.7, 79.6, 41.2, 39.6, 28.7, 28.2. HRMS (ES+): M+H, calcd 281.0501/283, found, 281.0509/283. Anal. Calcd for C$_9$HL$_{17}$BrN$_2$O$_3$: C, 38.45; H, 6.09; N, 9.96. Found: C, 38.78, H, 5.60, N, 9.82.

Procedure 1
Antimicrobial Assays
Tier I

A. *Streptococcus pyogenes*

*S. pyogenes* [American Type Culture Collection (ATCC) #14289] is used in this bacterial growth assay. To initiate the exponential phase of bacterial growth prior to the assay, a sample of bacteria is grown for 6 hours in Todd Hewitt Broth (Difco 0492-17-6) at 37° C. then re-inoculated into fresh media and grown overnight at 37° C. The bacterial cells are collected by centrifugation for 10 minutes at 3200 rpm, diluted and absorbance read at 595 nm. Bacteria diluted in 233 Todd-Hewitt Broth (75 ML) are added to the compound mixtures (75 μL) for a total volume of 150 μL. The assays are performed in 96-well microplates with approximately 1×10$^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic controls are concurrently tested in each screening assay.

Compounds are assayed in duplicate at a single dose. Compounds which show inhibitory activity are re-tested in duplicate at multiple doses to determine minimum inhibitory concentration (MIC).

B. *E. coli* imp−

The strain *E. coli* imp− obtained from Spencer Benson (Sampson, B. A., Misra, R. & Benson, S. A., *Genetics*, 1989, 122, 491–501, Identification and characterization of a new gene of *Escherichia coli* K-12 involved in outer membrane permeability) is used in this bacterial growth assay. To initiate the exponential phase of bacterial growth prior to the assay, a sample of bacteria is grown for 6 hours in Mueller Hinton II Broth (BBL 12322) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2×Mueller Hinton II Broth (75 μL) are added to the compound mixtures (75μL) for a total volume of 150 μL. The assays are performed in 96-well microplates with approximately 1×10$^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic controls are concurrently tested in each screening assay.

Compounds are assayed in duplicate at a single dose. Compounds which show inhibitory activity are re-tested in duplicate at multiple doses to determine minimum inhibitory concentration (MIC).

Tier II
Gram Positive

The following gram positive strains are used to test compounds which showed activity in at least one of the Tier I organisms: *Staphylococcus aureus* (ATCC #13709), *Entercoccus hirae* (ATCC #10541), *Streptococcus pyogenes* (ATCC #49399). To initiate the exponential phase of bacterial growth prior to the assay, a sample of bacteria is grown for 6 hours in Todd Hewitt Broth (Difco 0492–17–6) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2×Todd Hewitt Broth (75 μL) are added to the compound mixtures (75μL) for a total volume of 150 μL. The assays are performed in 96-well microplates with approximately 1×10$^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic controls are concurrently tested in each screening assay.

Compounds are assayed in duplicate at multiple doses to determine minimum inhibitory concentration (MIC).

Gram Negative

The following gram negative strains are used to test compounds which showed activity in at least one of the Tier I organisms: *Escherichia coli* (ATCC #25922), *Klebsiella pneumoniae* (ATCC #10031), *Proteus vulgaris* (ATCC #13315), and *Pseudomonas aeruginosa* (ATCC #9027). To initiate the "exponential" phase of bacterial growth prior to the assay, a sample of bacteria is grown for 6 hours in Mueller Hinton II Broth (BBL 12322) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2×Mueller Hinton II Broth (75 µL) are added to the compound mixtures (75µL) for a total volume of 150 µL. The assays are performed in 96-well microplates go .with approximately 1×10$^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin, tetracycline and ciprofloxacin antibiotic controls are concurrently tested in each screening assay.

Compounds are assayed in duplicate at multiple doses to determine minimum inhibitory concentration (MIC).

Libraries in accordance with the present invention have been tested for antibacterial activity utilizing assays that determine the minimum inhibitory concentration (MIC). The antibacterial assays utilize *Streptococcus pyogenes* and *Escherichia coli* imp–. Activity has been detected in a number of libraries of the present invention.

Procedure 2

Antifungal Assay

*C. albicans*

The strain *C. albicans* (ATCC #10231) is used. To initiate the exponential phase of yeast growth prior to the assay, a sample of yeast is grown overnight at 25° C. in YM Broth (Difco 0711-17-1). The yeast cells are collected by centrifugation for 10 minutes at 3200 rpm, diluted and absorbance read at 595 nm. Yeast diluted in 2×YM Broth (75 µL) are added to the compound mixtures (75 µL) for a total volume of 150 µL. The assays are performed in 96-well microplates with approximately 1×10$^4$ cells per well. The plates are incubated at 25° C. and growth monitored at 48 hours by visual inspection of yeast growth. Amphotericin B antifungal control is concurrently tested in each screening assay.

Compounds are assayed in duplicate at multiple doses to determine minimum inhibitory concentration (MIC).

Procedure 3

Red Blood Cell Lysis Assay

Compounds are tested for hemolysis of mammalian red blood cells. Horse red blood cells (Colorado Serum Co. #CS0004) are diluted 1:5 in 133 phosphate buffered saline (PBS). 50 µL diluted RBC's are added to 50 µL of test compound in 1×PBS (total volume=100 µL) in a round bottom 96-well microplate, mixed gently, and incubated 1 hour at 37° C. The microplate is then centrifuged for 5 minutes at 1000 rpm. The supernatant is diluted 1:5 (20 µL supernatant+80 µL 1×PBS) into a clean flat bottom 96-well microplate. Absorbance at 540 nm is read using a BioRad model 3550 UV microplate reader.

Compounds are tested in duplicate at multiple doses to determine the minimum hemolytic concentration (MHC).

Procedure 4

RNA Binding Assay

The Effect of Libraries on tat/TAR Interactions SPA Method (Scintillation Proximity Assay)

A fast assay targeting tat/TAR interactions was developed for high through-put screening. The assay is used to rapidly identify compounds which are capable of disrupting the interaction of HIV-1 tat protein with the TAR RNA stem/loop structure.

Material

A 39 residue tat peptide (aa 48–86 of HIV-1 tat protein). This is the C terminal basic binding domain of the tat protein. This peptide was synthesized by a contract lab and further labeled with $^{125}$I (specific activity 100 µCi/mL) at Amersham Life Sciences.

A 30 base RNA oligonucleotide (TAR oligonucleotide) consisting of the bulge and stem/loop structure of HIV TAR which has also been Biotin conjugated at the 3' end. This RNA oligonucleotide was synthesized in house.

PRB buffer: 50 mM Tris-HCl (pH 8.0), 0.01% NP-40, 10% glycerol, 1.5 mM $MgCl_2$, and 50 mM KCl.

Streptavidin coated SPA beads(Amersham Life Sciences).

Opaque 96 well plates.

Methods

Streptavidin coated SPA beads are incubated for 20 minutes at room temperature in a PRB buffer with 0.1 µCi of the labeled peptide and 100 nM of the biotin conjugated RNA oligonucleotide. Incubations are performed in the presence or absence of test samples in a volume of 50 µl in an opaque 96 well plate. Following the incubation the plates are spun at 1000 rpm for 5 minutes to settle the SPA beads. The biotintylated TAR oligonucleotide binds the steptavidin coated SPA bead. The labeled tat peptide associated with the biotintylated TAR oligonucleotide excites the scintillant in the SPA bead, resulting in a quantifiable signal which can be read in the TopCount 96 well scintillation counter. Compounds that interfere with the tat/TAR interaction result in $^{125}$I tat floating free in buffer where excited electrons are quenched before transferring energy to scintillant in the SPA bead. This is observed as a decrease in signal.

Procedure 5

Antimicrobial Mechanistic Assay

Bacterial DNA Gyrase

DNA gyrase is a bacterial enzyme which can introduce negative supercoils into DNA utilizing the energy derived from ATP hydrolysis. This activity is critical during DNA replication and is a well characterized target for antibiotic inhibition of bacterial growth. In this assay, libraries of compounds are screened for inhibition of DNA gyrase. The assay measures the supercoiling of a relaxed plasmid by DNA gyrase as an electrophoretic shift on an agarose gel. Initially all library pools are screened for inhibitory activity at 30 µM and then a dose response analysis is effected with active subsets. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The $IC_{50}$ was determined to be 8 nM, sufficient to identify the activity of a single active species of comparable activity in a library having 30 µMconcentration.

Procedure 6
Using Libraries for Identifying Metal Chelators and Imaging Agents

This procedure is used to identify compounds of the invention from libraries of compounds constructed to include a ring that contains an ultraviolet chromophore. Further the chemical functional groups attached to the compounds of the invention are selected from metal binders, coordinating groups such as amine, hydroxyl and carbonyl groups, and other groups having lone pairs of electrons, such that the compounds of the invention can form coordination complexes with heavy metals and imaging agents. The procedure is used to identify compounds of the invention useful for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the pool under assay. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library pool being assayed.

Procedure 7
Assay of Combinatorial Library for $PLA_2$ Inhibitors

A preferred target for assay of combinatorially generated pools of compounds is the phospholipase $A_2$ family. Phospholipases $A_2$ ($PLA_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P. D., ed., Academic Press, New York, 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. PLAS is regulated by pro-inflammatory cytokines and, thus, occupies a central position in the inflammatory cascade (Dennis, ibid.; Glaser et al., *TiPs Reviews* 1992, 14, 92; and Pruzanski et al., *Inflammation* 1992, 16, 451). All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath et al., *Inflammation* 1988, 12, 549) or into the articular space of rabbits (Bomalaski et al., *J. Immunol.* 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott et al., *Science* 1990, 250, 1541). Recently, the crystal structure of $PLA_2$ from human synovial fluid has been determined (Wery et al., *Nature* 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain diad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., *Cold Spring Harbor Symp. Quant. Biol.* 1987, 52, 441; Cho et al., *J. Biol. Chem.* 1988, 263, 11237; Yang et al., *Biochem. J.* 1989, 262, 855; and Noel et al., *J. Am. Chem. Soc.* 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in $PLA_2$ activity occur concurrently with changes in the fluorescence of a membrane probe (Burack et al., *Biochemistry* 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., *FEBS Lett.* 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (Yuan et al., *J. Am. Chem. Soc.* 1987, 109, 8071; Lombardo et al., *J. Biol. Chem.* 1985, 260, 7234; Washburn et al., *J. Biol. Chem.* 1991, 266, 5042; Campbell et al., *J. Chem. Soc., Chem. Commun.* 1988, 1560; and Davidson et al., *Biochem. Biophys. Res. Commun.* 1986, 137, 587), reports describing in vivo activity are limited (Miyake et al., *J. Pharmacol. Exp. Ther.* 1992, 263, 1302).

In one preferred embodiment, compounds of the invention are selected for their potential to interact with, and preferably inhibit, the enzyme $PLA_2$. Thus, compounds of the invention can be used for topical and/or systemic treatment of inflammatory diseases including atopic dermatitis and inflammatory bowel disease. In selecting the functional groups, advantage can be taken of $PLA_2$'s preference for anionic vesicles over zwitterionic vesicles. Preferred compounds of the invention for assay for $PLA_2$ include those having aromatic diversity groups to facilitate binding to the cleft of the $PLA_2$ enzyme (Oinuma et al., *J. Med. Chem.* 1991, 34, 2260; Marki et al., *Agents Actions* 1993, 38, 202; and Tanaka et al., *J. Antibiotics* 1992, 45, 1071). Benzyl and 4-hexylbenzyl groups are preferred aromatic diversity groups. $PLA_2$-directed compounds of the invention can further include hydrophobic functional groups such as tetraethylene glycol groups. Since the $PLA_2$ enzyme has a hydrophobic channel, hydrophobicity is believed to be an important property of inhibitors of the enzyme.

After each round of synthesis as described in the above examples, the resulting libraries or pools of compounds are screened for inhibition of human type II $PLA_2$ enzymatic activity. The assay is effected at the conclusion of each round of synthesis to identify the wining pool from that round of synthesis. Concurrently, the libraries additionally can be screened in other in vitro assays to determine further mechanisms of inhibition.

The pools of the libraries are screened for inhibition of $PLA_2$ in the assay using *E. coli* labeled with $^3H$-oleic acid (Franson et al., *J. Lipid Res.* 1974, 15, 380; and Davidson et al., *J. Biol. Chem.* 1987, 262, 1698) as the substrate. Type II $PLA_2$ (originally isolated from synovial fluid), expressed in a baculovirus system and partially purified, serves as a source of the enzyme. A series of dilutions of each of the library pools is done in water: 10 Al of each pool is incubated for 5 minutes at room temperature with a mixture of 10 $\mu$l $PLA_2$, 20 $\mu$l 5×$PLA_2$ Buffer (500 mM Tris 7.0–7.5, 5 mM $CaCl_2$), and 50 $\mu$l water. Samples of each pool are run in duplicate. At this point, $\mu$l of $^3H$ *E. coli* cells is added. This mixture is incubated at 37° C. for 15 minutes. The enzymatic reaction is stopped with the addition of 50 $\mu$L 2M HCl and 50 $\mu$L fatty-acid-free BSA (20 mg/mL PBS), vortexed for 5 seconds, and centrifuged at high speed for 5 minutes. 165 $\mu$L of each supernate is then put into a scintillation vial containing 6 ml of scintillant (ScintiVerse) and cpms are measured in a Beckman Liquid Scintillation Counter. As a control, a reaction without the combinatorial pool is run alongside the other reactions as well as a baseline reaction containing no compounds of the invention as well as no $PLA_2$ enzyme. CPMs are corrected for by subtracting the baseline from each reaction data point.

Confirmation of the "winners" is made to confirm that a compound of the invention binds to enzyme rather than substrate and that the inhibition by a compound of the invention that is selected is specific for type II $PLA_2$. An assay using $^{14}C$-phosphatidyl ethanolamine ($^{14}C$-PE) as substrate, rather than *E. coli* membrane, is used to insure enzyme rather than substrate specificity. Micelles of $^{14}C$-PE and deoxycholate are incubated with the enzyme and a compound of the invention. $^{14}C$-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

Procedure 8

Probes for the Detection of Specific Proteins and mRNA in Biological Samples

For the reliable, rapid, simultaneous quantification of multiple varieties of proteins or mRNA in a biological sample without the need to purify the protein or mRNA from other cellular components, a protein or mRNA of interest from a suitable biological sample, i.e., a blood borne virus, a bacterial pathogen product in stool, urine and other like biological samples, is identified using standard microbiological techniques. A probe comprising a compound of a combinatorial library of the invention is identified by a combinatorial search as noted in the above examples. Preferred for the protein probe are compounds synthesized to include chemical functional groups that act as hydrogen bond donors and acceptors, sulfhydryl groups, hydrophobic lipophilic moieties capable of hydrophobic interactions groups and groups capable of ionic interactions. The probe is immobilized on insoluble CPG solid support utilizing the procedure of Pon, R.T., Protocols for Oligonucleotides and Analogs, Agrawal, S., Ed., Humana Press, Totowa, N.J., 1993, p 465–496. A known aliquot of the biological sample under investigation is incubated with the insoluble CPG support having the probe thereon for a time sufficient to hybridize the protein or mRNA to the probe and thus form a linkage via the probe to the solid support. This immobilizes the protein or mRNA present in the sample to the CPG support. Other non-immobilized materials and components are then washed off the CPG with a wash media suitable for use with the bio-logical sample. The mRNA on the support is labeled with ethidium bromide, biotin or a commercial radionucleotide and the amount of label immobilized on the CPG support is measured to indicate the amount of mRNA present in the biological sample. In a similar assay a protein is also labeled and quantified.

Procedure 9

Leukotriene $B_4$ Assay

Leukotriene $B_4$ ($LTB_4$) has been implicated in a variety of human inflammatory diseases, and its pharmacological effects are mediated via its interaction with specific surface cell receptors. Library subsets are screened for competitive inhibition of radiolabeled $LTB_4$ binding to a receptor preparation.

A Nenquest™ Drug Discovery System Kit (NEN Research Products, Boston, Mass.) is used to select an inhibitor of the interaction of Leukotriene $B_4$ ($LTB_4$) with receptors on a preparation of guinea pig spleen membrane. [$^3H$] Leukotriene $B_4$ reagent is prepared by adding 5 mL of ligand diluent (phosphate buffer containing NaCl, $MgCl_2$, EDTA and Bacitracin, pH 7.2) to 0.25 mL of the radioligand. The receptor preparation is made by thawing the concentrate, adding 35 mL of ligand diluent and swirling gently in order to re-suspend the receptor homogeneously. Reagents are kept on ice during the course of the experiment, and the remaining portions are stored at −20° C.

Library subsets prepared as per general procedure of examples above are diluted to 5 μM, 50 μM and 500 μM in phosphate buffer (1×PBS, 0.1% azide and 0.1% BSA, pH 7.2), yielding final test concentrations of 0.5 μM, 5 μM and 50 LAM, respectively. Samples are assayed in duplicate. [$^3$H] LTB$_4$ (25 μL) is added to 25 μL of either appropriately diluted standard (unlabeled LTB,) or library subset. The receptor suspension (0.2 mL) is added to each tube. Samples are incubated at 4° C. for 2 hours. Controls include [$^3$H] LTB$_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total counts to determine the net cpm for each sample. The degree of inhibition of binding for each library subset is determined relative to the standard (sample of ligand and receptor without library molecules).

What is claimed is:

1. A compound having the formula:

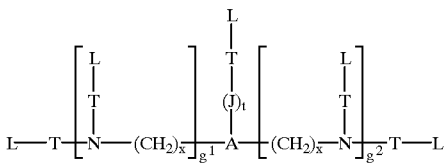

wherein:

$g^1$ is 1 to 4;

$g^2$ is 2 to 4;

A is an aromatic, heterocyclic, or alicyclic ring system;

each x is, independently, 1 to 8;

J is N, O, S, or a heterocyclic ring system having at least one nitrogen;

t is 0 or 1;

each T is, independently, a single bond, a methylene group or a group having the formula:

each $R^1$, $R^2$ and $R^3$ is, independently, H, alkyl or haloalkyl having 1 to 10 carbon atoms, alkenyl having 2 to 10 carbon atoms, alkynyl having 2 to 10 carbon atoms, or aryl having 6 to 14 carbon atoms;

each $R^5$ and E is, independently, a single bond; CH=CH; C≡C; O; S; $NR^3$; $SO_2$; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from hydroxyl (OH), alkoxy, alcohol, benzyl, phenyl, nitro ($NO_2$), thiol (SH), thioalkoxy, halogen, alkyl, aryl, alkenyl, and alkynyl groups;

each $R^6$ is =O, =S, =$NR^3$;

each m and n is, independently, zero to 5;

each p is, independently, zero or 1;

q is 1 to 10;

each L is, independently, H, $C_1$–$C_{10}$ alkyl, substituted alkyl; $C_2$–$C_{10}$ alkenyl; substituted alkenyl; $C_2$–$C_{10}$ alkynyl; substituted alkynyl; $C_4$–$C_7$ carbocyclic alkyl; substituted carbocyclic alkyl; alkenyl carbocyclic; substituted alkenyl carbocyclic; alkynyl carbocyclic; substituted alkynyl carbocyclic; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from alkyl, alkenyl, alkynyl, aryl, hydroxyl, alkoxy, alcohol, benzyl, nitro, thiol, thioalkyl, thioalkoxy, trifluoromethyl or halogen groups; or L is phthalimido, an ether having 2 to 10 carbon atoms and 1 to 4 oxygen or sulfur atoms, a metal coordination group, a conjugate group, halogen, hydroxyl, thiol, keto, carboxyl, $NR^1R^2$, $CONR^1$, amidine (C(=NH)$NR^2R^3$), guanidine (NHC(=NH)$NR^2R^3$), glutamyl ($R^1$OOCCH($NR^2R^3$)($CH_2$)$_2$C(=O), nitrate, nitro, nitrile, trifluoromethyl, trifluoromethoxy, NH-alkyl, N-dialkyl, O-aralkyl, S-aralkyl, NH-aralkyl, azido (N3), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a drug, or a group capable of hydrogen bonding;

with the proviso that when A is 2,6-disubstituted pyridine with $g^1$ equal to 2 and $g^2$ equal to 2, and having 6 of said L groups, then not more than 3 of said L groups are H or para-toluenesulfonyl;

with the further proviso that not more than one —T—L is H.

2. The compound of claim 1 wherein $g^1$ is not equal to $g^2$.

3. The compound of claim 1 wherein $g^1$ is 1 and $g^2$ is 2.

4. The compound of claim 1 wherein $g^1$ is 1 and $g^2$ is 3.

5. The compound of claim 1 wherein at least 3 of said L groups are different.

6. The compound of claim 1 wherein at least 4 of said L groups are different.

7. The compound of claim 1 wherein at least one of said L groups is phthalimido.

8. The compound of claim 1 wherein t is 1 and J is a heterocyclic ring system.

9. The compound of claim 8 wherein said heterocyclic ring system is piperazine.

10. The compound of claim 1 wherein A is benzene, naphthalene, anthracene, cyclohexane, cyclopentane or adamantane.

11. The compound of claim 1 wherein A comprises a nitrogen, oxygen or sulfur containing heterocycle.

12. The compound of claim 11 wherein said nitrogen, oxygen or sulfur containing heterocycle is furan, pyran thiophene, aziridine, azetine, pyridine, 1,3,5-triazine, a-triazine, as-triazine, cyanuric acid, pyrrole, pyrazole, 1,2, 3-triazole, imidazole, pyrimidine, purine, piperidine, pyrazole, pyrrolidine, piperazine, pyrazine, pyridazine, morpholine, oxazole, isoxazole, thiazole, or isothiazole.

13. The compound of claim 1 wherein the sum of $g^1$ added to $g^2$ is from 3 to 8.

14. The compound of claim 1 wherein the sum of $g^1$ added to $g^2$ is from 3 to 6.

15. The compound of claim 1 wherein the sum of $g^1$ added to $g^2$ is from 3 to 4.

16. The compound of claim 1 wherein the sum of $g^1$ added to $g^2$ is an odd number from 3 to 7.

17. A compound having the formula:

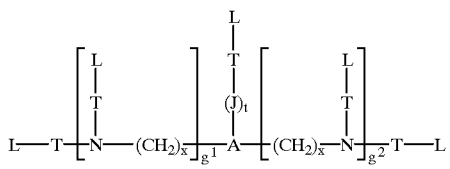

wherein:

$g^1$ is 1 to 4;
$g^2$ is 2 to 4;
A is a heterocyclic ring system;
each x is, independently, 1 to 8;
J is N, O, S, or a heterocyclic ring system having at least one nitrogen;
t is 0 or 1;
each T is, independently, a single bond, a methylene group or a group having the formula:

each $R^1$, $R^2$ and $R^3$ is, independently, H, alkyl or haloalkyl having 1 to 10 carbon atoms, alkenyl having 2 to 10 carbon atoms, alkynyl having 2 to 10 carbon atoms, or aryl having 6 to 14 carbon atoms;
each $R^5$ and E is, independently, a single bond; CH=CH; C≡C; O; S; $NR^3$; $SO_2$; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from hydroxyl (OH), alkoxy, alcohol, benzyl, phenyl, nitro ($NO_2$), thiol (SH), thioalkoxy, halogen, alkyl, aryl, alkenyl, and alkynyl groups;
each $R^6$ is =O, =S, =$NR^3$;
each m and n is, independently, zero to 5;
each p is, independently, zero or 1;
q is 1 to 10;
each L is, independently, H, $C_1$–$C_{10}$ alkyl, substituted alkyl; $C_2$–$C_{10}$ alkenyl; substituted alkenyl; $C_2$–$C_{10}$ alkynyl; substituted alkynyl; $C_4$–$C_7$ carbocyclic alkyl; substituted carbocyclic alkyl; alkenyl carbocyclic; substituted alkenyl carbocyclic; alkynyl carbocyclic; substituted alkynyl carbocyclic; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from alkyl, alkenyl, alkynyl, aryl, hydroxyl, alkoxy, alcohol, benzyl, nitro, thiol, thioalkyl, thioalkoxy, trifluoromethyl or halogen groups; or L is phthalimido, an ether having 2 to 10 carbon atoms and 1 to 4 oxygen or sulfur atoms, a metal coordination group, a conjugate group, halogen, hydroxyl, thiol, keto, carboxyl, $NR^1R^2$, $CONR^1$, amidine (C(=NH)$NR^2R^3$), guanidine (NHC(=NH)$NR^2R^3$), glutamyl ($R^1OOCCH(NR^2R^3)(CH_2)_2C$(=O)), nitrate, nitro, nitrile, trifluoromethyl, trifluoromethoxy, NH-alkyl, N-dialkyl, O-aralkyl, S-aralkyl, NH-aralkyl, azido ($N_3$), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a drug, or a group capable of hydrogen bonding;
with the proviso that when A is 2,6-disubstituted pyridine with $g^1$ equal to 2 and $g^2$ equal to 2, and having 6 of said L groups, then not more than 3 of said L groups are H or para-toluenesulfonyl;
with the further proviso that not more than one —T—L is H.

* * * * *

UNITED STATES PATENT AND TRADEMARK OFFICE
CERTIFICATE OF CORRECTION

PATENT NO. : 6,329,523 B1
DATED : December 11, 2001
INVENTOR(S) : Cook et al.

It is certified that error appears in the above-identified patent and that said Letters Patent is hereby corrected as shown below:

Column 2,
Line 22, please delete "oligonucleotides" and insert therefor -- oligonucleosides --;

Column 5,
Line 60, please delete "$R^1$" and insert therefor -- $R^5$ --;

Column 7,
Line 3, please delete "-(J)t-T-L;" and insert therefor -- $-(J)_t$-T-L; --;

Column 12,
Line 41, please delete the "30" after the word benzisoxazine;

Column 15,
Line 53, please delete "(PMOC)" and insert therefor -- (FMOC) -- ;

Column 16,
Line 7, please delete "T-BOC" and insert therefor -- t-BOC--;

Column 17,
Line 4, please delete "SURFʋ" and insert therefor -- SURF$^{TM}$ --;

Column 21,
Line 33, please delete "$R^1$" and insert therefor -- $R^6$ --;
Line 38, please delete "$C_2$-$C_1$ and insert therefor -- $C_2$-$C_{10}$ --;

Column 37,
Line 64, please delete "50" and insert therefor -- 5% --;

Column 41,
Line 37, please delete "2-(Aminamethyl)" and insert therefor
-- 2-(Aminomethyl) --;

Column 42,
Line 10, please delete "4-(p-Toluensaulfonylmethyl)" and insert therefor
-- 4-(p-Toluenesulfonylmethyl) --;
Line 24, please delete "4-(Azidamethyl)" and insert therefor
-- 4-(Azidomethyl) --;
Line 53, please delete "2-(Aninomethyl)-4-(azidamethyl)" and insert therefor
-- 2-(Aminomethyl)-4-(azidomethyl) --;

UNITED STATES PATENT AND TRADEMARK OFFICE
CERTIFICATE OF CORRECTION

PATENT NO. : 6,329,523 B1
DATED : December 11, 2001
INVENTOR(S) : Cook et al.

It is certified that error appears in the above-identified patent and that said Letters Patent is hereby corrected as shown below:

Column 44,
Line 53, please delete "2-N-(m-methoxyearbonylbenzyl)" and insert therefor
-- 2-N-(methoxycarbonylbenzyl) --;

Column 46,
Line 34, please delete "methanol-30aqueous" and insert therefor
-- methanol-30% aqueous --;
Line 51, please delete "-Aminamethylene" and insert therefor -- -Aminomethylene --;
Line 52, please delete "($L2_2$)" and insert there for -- ($L_{12}$) --;

Column 48,
Line 25, please delete "($L_8$-Br)," and insert therefor -- ($L_6$-Br), --;
Lines 27 & 28, please delete "($L_{17}$-Br), im-chlorobenzyl bromide ($L_8$-Br)"
and insert therefor -- ($L_{17}$-Br), m-chlorobenzyl bromide ($L_{18}$-Br) --;
Line 62, please delete "aminamethylene" and insert therefor -- aminomethylene --;

Column 49,
Line 4, please delete "($LI_6$-Br)," and insert therefor -- ($L_{16}$-Br), --;
Line 6, please delete "($L_{19}$-Br)" and insert therefor -- ($L_{l8}$-Br) --;
Line 6, please delete "($L_{19}$-Br)" and insert therefor -- ($L_{18}$-Br) --;
Line 14, please delete "[(N1-L)" and insert therefor -- [(N1-$L_N$) --;
Line 61, please delete "4-(Bis-N, N-L)" and insert therefor -- 4-Bis-N,N-$L_n$) --;

Column 50,
Line 5, please delete "($L_{18}$-Br)," and insert therefor -- ($L_{17}$-Br), --;
Lines 36 & 37, please delete "($L_{25}$-Br), m-cyanobenzyl bromide ($L_6$-Br)," and insert
therefor -- ($L_{15}$-Br), m-cyanobenzyl bromide ($L_{16}$-Br), --;
Line 43, please delete "aminamethylene" and insert therefor -- aminomethylene --;
Line 52, please delete "($L_{18}$-Br)," and insert therefor --( $L_8$-Br), --;

Column 51,
Line 21, please delete "F760-1 2-Fyluorobenzyl chloride" and insert therefor
-- F 760-1 2-Fluorobenzyl chloride --;
Line 67, please delete "$C_{4040}$-5" and insert therefor -- C4040-5 --;

UNITED STATES PATENT AND TRADEMARK OFFICE
CERTIFICATE OF CORRECTION

PATENT NO. : 6,329,523 B1
DATED : December 11, 2001
INVENTOR(S) : Cook et al.

It is certified that error appears in the above-identified patent and that said Letters Patent is hereby corrected as shown below:

Column 54,
Line 7, please delete the "1";
Line 8, please delete "1221-6" and insert therefor -- 11221-6 --;
Line 9, please delete "5740-0" and insert therefor -- B5740-0 --;
Line 46, please delete "15104-1 2, 4 - Dinethylbenzaldehyde" and insert therefor -- 15104-1 2,4-Dimethylbenzaldehyde --;

Column 55,
Line 20, please delete "$C_{5880}$-0" and insert therefor -- C5880-0 --;
Line 22, please delete "$C_{5870}$-3" and insert therefor -- C5870-3 --;
Line 26, please delete "$H_{4810}$-7" and insert therefor -- H4810-7 --;
Line 50, please delete "12948-8 5-odovanillin" and insert therefor --12948-8 5-Iodovanillin --;

Column 56,
Line 30, please delete "N1o-9" and insert therefor -- N10-9 --;
Line 65, please delete "$H_{212}$-0" and insert therefor -- H212-0 --;

Column 59,
Line 43, please delete "Ln" and insert therefor -- $L_n$ --;

Column 60,
Line 5, please delete "3, -bis-chloromethyl-" and insert therefor -- 3,5 -bis-chloromethyl- --;
Line 16, please delete "-5-(N-$L_n$)" and insert therefor -- -5-(N-$L_a$ --;

Column 61,
Line 43, please delete "($CL_2Ha_8NO_3$" and insert therefor -- ($C_{12}H_{18}NO_3$ --;
Line 60, please delete "($C_{12}HL_6BrNo_2Na$" and insert therefor -- ($C_{12}H_{16}BrNO_2Na$ --;

Column 62,
Line 32, please delete "TLC Rf" and insert therefor -- TLC $R_f$ --;
Line 33, please delete "(sg 18H)," and insert therefor -- (s,18H), --;

UNITED STATES PATENT AND TRADEMARK OFFICE
CERTIFICATE OF CORRECTION

PATENT NO.    : 6,329,523 B1
DATED         : December 11, 2001
INVENTOR(S)   : Cook et al.

It is certified that error appears in the above-identified patent and that said Letters Patent is hereby corrected as shown below:

Column 63,
Line 50, please delete "C:HlgBrN$_2$O$_3$:" and insert therefor -- C$_{11}$H$_{19}$BrN$_2$O$_3$: --;

Column 64,
Line 2, please delete "(C$_{21}$H$_{19}$ClN$_2$O$_3$Na" and insert therefor
--(C$_{11}$H$_{19}$ClN$_2$O$_3$Na --;
Line 22, please delete "(C$_{37}$H$_{24}$ClN$_2$O$_3$" and insert therefor -- (C$_{17}$H$_{24}$ClN$_2$O$_3$ --;
Line 52, please delete "(S.24g, 20mmo1)" and insert therefor
-- (5.24g, 20mmo1) --;

Column 66,
Line 12, please delete "100W EtOAc" and insert therefor -- 100% EtOAc --;

Column 67,
Line 6, please delete "(C$_{31}$H$_{39}$N$_{7s2}$O$_{12}$Cs" and insert therefor
-- (C$_{31}$H$_{39}$N$_7$S$_2$O$_{12}$Cs --;

Column 67,
Line 32, please delete "(C$_{19}$H$_{33}$NSO$_3$Na" and insert therefor -- (C$_{19}$H$_{33}$N$_5$O$_3$Na --;
Line 57, please delete "(M+Cs)4" and insert therefor -- (M+Cs)$^+$ --;

Column 68,
Line 16, please delete "(m,1H)," and insert therefor -- (m,11 H), --;
Line 21, please delete "(C$_3$OH$_{36}$N$_5$O$_2$F$_6$" and insert therefor -- (C$_{30}$H$_{36}$N$_5$O$_2$F$_6$ --;
Line 55, please delete "C$_{34}$H$_{51}$,N$_7$O,S:" and insert therefor -- C$_{34}$H$_{51}$N$_7$O$_{11}$S: --;

Column 69,
Line 14, please delete "C$_{28}$H$_{48}$N6O$_7$:" and insert therefor -- C$_{28}$H$_{48}$N$_6$O$_7$:; --;

Column 70,
Line 23, please delete "(C$_{21}$H$_3$N6OF$_6$" and insert therefor -- (C$_{21}$H$_3$N$_6$OF$_6$ --;

UNITED STATES PATENT AND TRADEMARK OFFICE
CERTIFICATE OF CORRECTION

PATENT NO. : 6,329,523 B1
DATED : December 11, 2001
INVENTOR(S) : Cook et al.

It is certified that error appears in the above-identified patent and that said Letters Patent is hereby corrected as shown below:

Column 70,
Line 41, please delete "(Na" and insert therefor -- ($Na_2SO_4$), --;

Column 71,
Line 22, please delete "-500" and insert therefor -- -50° --;
Line 66, please delete "$C_9HL_{17}BrN_2O_3$:" and insert therefor -- $C_9H_{17}BrN_2O_3$:; --;

Column 72,
Line 13, please delete "233 Todd-Hewitt Broth (75ML)" and insert therefor
-- 2x Todd-Hewitt Broth (75µL) --;

Column 75,
Line 44, please delete "PLAS" and insert therefor -- $PLA_2$ --;

Column 77,
Line 45, please delete "10Al" and insert therefor --10µl --;

Column 79,
Line 61, please delete "2to" and insert therefor -- 2 to --;

Signed and Sealed this

Twelfth Day of November, 2002

Attest:

JAMES E. ROGAN
Attesting Officer          Director of the United States Patent and Trademark Office